US010557167B2

(12) United States Patent
Kawai et al.

(10) Patent No.: US 10,557,167 B2
(45) Date of Patent: *Feb. 11, 2020

(54) BIOMOLECULE SEQUENCING DEVICES, SYSTEMS AND METHODS

(71) Applicant: Quantum Biosystems Inc., Tokyo (JP)

(72) Inventors: Tomoji Kawai, Osaka (JP); Masateru Taniguchi, Osaka (JP); Takahito Ohshiro, Osaka (JP); Mark Oldham, Emerald Hills, CA (US); Eric Nordman, Palo Alto, CA (US)

(73) Assignee: QUANTUM BIOSYSTEMS INC., Tokyo (JP)

( * ) Notice: Subject to any disclaimer, the term of this patent is extended or adjusted under 35 U.S.C. 154(b) by 59 days.

This patent is subject to a terminal disclaimer.

(21) Appl. No.: 15/448,317

(22) Filed: Mar. 2, 2017

(65) Prior Publication Data

US 2018/0023132 A1    Jan. 25, 2018

Related U.S. Application Data

(63) Continuation of application No. 15/061,871, filed on Mar. 4, 2016, now Pat. No. 9,644,236, which is a
(Continued)

(30) Foreign Application Priority Data

Sep. 18, 2013 (JP) .................................. 2013-193498
Sep. 24, 2013 (JP) .................................. 2013-197443

(51) Int. Cl.
*C12Q 1/68* (2018.01)
*G06F 19/22* (2011.01)
(Continued)

(52) U.S. Cl.
CPC ........... *C12Q 1/6869* (2013.01); *G01N 27/04* (2013.01); *G16B 30/00* (2019.02)

(58) Field of Classification Search
None
See application file for complete search history.

(56) References Cited

U.S. PATENT DOCUMENTS 5,092,972 A    3/1992  Ghowsi
5,122,248 A    6/1992  Karger et al.
(Continued)

FOREIGN PATENT DOCUMENTS

CN    1828849 A    9/2006
CN    101046458 A    10/2007
(Continued)

OTHER PUBLICATIONS

Anima et al. Fabrications of insulator-protected nanometer-sized electrode gaps. Journal of Applied Physics 115:114310 (2014). 6 pages. doi: 10.1063/1.4869135.
(Continued)

*Primary Examiner* — Jermele M Hollington
(74) *Attorney, Agent, or Firm* — Wilson Sonsini Goodrich & Rosati

(57) ABSTRACT

Devices, systems and methods for sequencing protein samples are provided. In some examples, currents generated when a monomer passes through between electrodes of a nanogap electrode pair are measured for each of several different distances, so that monomers are identified when compared to a reference physical quantity of a known monomer, which may be obtained from a current measured with a similar inter-electrode distance(s) at which each of plural kinds of monomers are identifiable and ordered with predetermined accuracy and based on a detected physical quantity obtained from a tunneling current, which may be
(Continued)

further normalized by the use of one or more reference substances.

24 Claims, 28 Drawing Sheets

Related U.S. Application Data continuation of application No. PCT/US2014/056173, filed on Sep. 17, 2014.

(51) Int. Cl.
    *G01N 27/04*      (2006.01)
    *C12Q 1/6869*      (2018.01)
    *G16B 30/00*      (2019.01)

(56) References Cited

U.S. PATENT DOCUMENTS

| | | |
|---|---|---|
| 5,151,164 A | 9/1992 | Blanchard et al. |
| 5,262,031 A | 11/1993 | Lux et al. |
| 5,329,236 A | 7/1994 | Gemma et al. |
| 5,593,838 A | 1/1997 | Zanzucchi et al. |
| 5,906,723 A | 5/1999 | Mathies et al. |
| 6,159,353 A | 12/2000 | West et al. |
| 6,447,663 B1 | 9/2002 | Lee et al. |
| 6,491,805 B1 | 12/2002 | Gordon et al. |
| 6,613,513 B1 | 9/2003 | Parce et al. |
| 6,905,586 B2 | 6/2005 | Lee et al. |
| 7,033,476 B2 | 4/2006 | Lee et al. |
| 7,468,271 B2 | 12/2008 | Golovchenko et al. |
| 7,892,414 B1 | 2/2011 | Sumner |
| 7,918,979 B2 | 4/2011 | Han et al. |
| 8,105,471 B1 | 1/2012 | Han et al. |
| 8,236,595 B2 | 8/2012 | Agarwal et al. |
| 8,333,934 B2 | 12/2012 | Cao et al. |
| 8,652,779 B2 | 2/2014 | Turner et al. |
| 9,194,838 B2 | 11/2015 | Taniguchi et al. |
| 9,506,894 B2 | 11/2016 | Kawai et al. |
| 9,535,033 B2 | 1/2017 | Tomoji et al. |
| 9,644,236 B2 * | 5/2017 | Kawai .................. C12Q 1/6869 |
| 10,202,644 B2 | 2/2019 | Taniguchi et al. |
| 10,261,066 B2 | 4/2019 | Ikeda et al. |
| 10,413,903 B2 | 9/2019 | Taniguchi |
| 10,438,811 B1 | 10/2019 | Ikeda |
| 10,466,228 B2 | 11/2019 | Ikeda et al. |
| 2001/0046681 A1 | 11/2001 | Senapathy |
| 2002/0046953 A1 | 4/2002 | Lee et al. |
| 2002/0081744 A1 | 6/2002 | Chan et al. |
| 2002/0168671 A1 | 11/2002 | Burns et al. |
| 2002/0168810 A1 | 11/2002 | Jackson |
| 2003/0052006 A1 * | 3/2003 | Noca ................ G01N 27/44704 204/450 |
| 2003/0075445 A1 | 4/2003 | Woudenberg et al. |
| 2003/0085719 A1 | 5/2003 | Yoon et al. |
| 2003/0089606 A1 | 5/2003 | Parce et al. |
| 2003/0104428 A1 | 6/2003 | Branton et al. |
| 2003/0141189 A1 | 7/2003 | Lee et al. |
| 2003/0207326 A1 | 11/2003 | Su et al. |
| 2004/0124084 A1 | 7/2004 | Lee et al. |
| 2004/0144658 A1 | 7/2004 | Flory |
| 2004/0161708 A1 | 8/2004 | Nagase et al. |
| 2005/0048513 A1 | 3/2005 | Harwit et al. |
| 2005/0051768 A1 | 3/2005 | Kim et al. |
| 2005/0061669 A1 | 3/2005 | Woudenberg et al. |
| 2005/0084865 A1 | 4/2005 | Yu et al. |
| 2005/0112860 A1 | 5/2005 | Park et al. |
| 2005/0127035 A1 | 6/2005 | Ling et al. |
| 2005/0136419 A1 | 6/2005 | Lee |
| 2005/0202444 A1 | 9/2005 | Zhu |
| 2005/0202446 A1 | 9/2005 | Yang et al. |
| 2005/0227239 A1 | 10/2005 | Joyce |
| 2006/0011480 A1 | 1/2006 | Sano et al. |
| 2006/0057585 A1 | 3/2006 | McAllister |
| 2006/0071209 A1 | 4/2006 | Flory et al. |
| 2006/0154399 A1 | 7/2006 | Sauer et al. |
| 2006/0154400 A1 | 7/2006 | Choi et al. |
| 2006/0210995 A1 | 9/2006 | Joyce |
| 2006/0275911 A1 | 12/2006 | Wang et al. |
| 2007/0029911 A1 | 2/2007 | Hudspeth et al. |
| 2007/0042366 A1 | 2/2007 | Ling |
| 2007/0048745 A1 | 3/2007 | Joyce et al. |
| 2007/0171714 A1 | 7/2007 | Wu et al. |
| 2007/0183198 A1 | 8/2007 | Otsuka et al. |
| 2008/0077607 A1 | 3/2008 | Gatawood et al. |
| 2008/0119366 A1 * | 5/2008 | Sauer .................. C12Q 1/6874 506/7 |
| 2008/0171316 A1 | 7/2008 | Golovchenko et al. |
| 2008/0202931 A1 | 8/2008 | Petsev et al. |
| 2008/0215252 A1 | 9/2008 | Kawai et al. |
| 2008/0248561 A1 | 10/2008 | Golovchenko et al. |
| 2009/0023146 A1 | 1/2009 | Harnack et al. |
| 2009/0155917 A1 | 6/2009 | Umezawa et al. |
| 2009/0215156 A1 | 8/2009 | Chung et al. |
| 2009/0229854 A1 | 9/2009 | Fredenberg et al. |
| 2009/0242429 A1 | 10/2009 | Sitdikov et al. |
| 2009/0283412 A1 | 11/2009 | Sansinena et al. |
| 2009/0286936 A1 | 11/2009 | Ogata et al. |
| 2009/0305273 A1 | 12/2009 | Cao et al. |
| 2010/0025249 A1 | 2/2010 | Polonsky et al. |
| 2010/0066348 A1 | 3/2010 | Merz et al. |
| 2010/0084276 A1 | 4/2010 | Lindsay et al. |
| 2010/0184062 A1 | 7/2010 | Steinmueller-Nethl et al. |
| 2010/0188109 A1 | 7/2010 | Edel et al. |
| 2010/0243449 A1 | 9/2010 | Oliver |
| 2010/0267158 A1 | 10/2010 | Chou et al. |
| 2010/0292101 A1 | 11/2010 | So |
| 2010/0331194 A1 | 12/2010 | Turner et al. |
| 2011/0056845 A1 | 3/2011 | Stellacci et al. |
| 2011/0171634 A1 | 7/2011 | Xiao et al. |
| 2011/0179852 A1 | 7/2011 | Polonsky et al. |
| 2011/0181150 A1 | 7/2011 | Mahameed et al. |
| 2011/0193183 A1 | 8/2011 | Agarwal et al. |
| 2011/0236984 A1 | 9/2011 | Sun et al. |
| 2011/0250464 A1 | 10/2011 | Wilson et al. |
| 2011/0287956 A1 | 11/2011 | Iqbal et al. |
| 2012/0041727 A1 | 2/2012 | Mishra et al. |
| 2012/0097539 A1 | 4/2012 | Qian et al. |
| 2012/0132886 A1 | 5/2012 | Peng et al. |
| 2012/0184047 A1 | 7/2012 | Jonsson et al. |
| 2012/0193237 A1 * | 8/2012 | Afzali-Ardakani .... B82Y 15/00 204/627 |
| 2012/0199485 A1 | 8/2012 | Sauer et al. |
| 2012/0254715 A1 | 10/2012 | Schwartz et al. |
| 2012/0298511 A1 | 11/2012 | Yamamoto |
| 2012/0322055 A1 | 12/2012 | Royyuru |
| 2013/0001082 A1 | 1/2013 | Afzali-Ardakani et al. |
| 2013/0092547 A1 | 4/2013 | Li et al. |
| 2013/0157271 A1 | 6/2013 | Coursey et al. |
| 2013/0186758 A1 | 7/2013 | Saha et al. |
| 2013/0264207 A1 | 10/2013 | Ju et al. |
| 2013/0334047 A1 | 12/2013 | Jeong et al. |
| 2014/0000105 A1 | 1/2014 | Bielick et al. |
| 2014/0008225 A1 | 1/2014 | Jeon et al. |
| 2014/0031995 A1 | 1/2014 | Kawai et al. |
| 2014/0055150 A1 | 2/2014 | Kawai et al. |
| 2014/0103945 A1 | 4/2014 | Eid et al. |
| 2014/0183040 A1 | 7/2014 | Kawai et al. |
| 2014/0202857 A1 | 7/2014 | Valbusa et al. |
| 2014/0273186 A1 | 9/2014 | Oxenrider |
| 2014/0300339 A1 | 10/2014 | Taniguchi et al. |
| 2014/0302675 A1 | 10/2014 | Astier et al. |
| 2014/0364324 A1 | 12/2014 | Turner et al. |
| 2014/0374695 A1 | 12/2014 | Astier et al. |
| 2015/0107996 A1 | 4/2015 | Chen |
| 2015/0111759 A1 | 4/2015 | Ju et al. |
| 2015/0132756 A1 | 5/2015 | Peter et al. |
| 2015/0219593 A1 | 8/2015 | Kawai et al. |
| 2015/0310228 A1 | 10/2015 | Benz et al. |
| 2015/0323490 A1 | 11/2015 | Luan et al. |
| 2016/0048690 A1 | 2/2016 | Tanishima et al. |
| 2016/0049327 A1 | 2/2016 | Singh et al. |
| 2016/0138101 A1 | 5/2016 | Taniguchi et al. |

(56) References Cited

U.S. PATENT DOCUMENTS

| | | |
|---|---|---|
| 2016/0245789 A1 | 8/2016 | Ikeda et al. |
| 2016/0245790 A1 | 8/2016 | Kawai et al. |
| 2016/0319342 A1 | 11/2016 | Kawai et al. |
| 2016/0320364 A1 | 11/2016 | Shuji et al. |
| 2016/0377591 A1* | 12/2016 | Kawai ............ G01N 33/48721 204/454 |
| 2017/0131237 A1 | 5/2017 | Ikeda |
| 2017/0144158 A1 | 5/2017 | Taniguchi |
| 2017/0146510 A1 | 5/2017 | Ikeda et al. |
| 2017/0146511 A1* | 5/2017 | Taniguchi ........ G01N 33/48721 |
| 2019/0242846 A1* | 8/2019 | Taniguchi ............. B82Y 40/00 |

FOREIGN PATENT DOCUMENTS

| | | |
|---|---|---|
| CN | 101920932 A | 12/2010 |
| CN | 102180440 A | 9/2011 |
| CN | 102753708 A | 10/2012 |
| CN | 102914395 A | 2/2013 |
| CN | 103203256 A | 7/2013 |
| CN | 103502795 A | 1/2014 |
| EP | 1419112 A1 | 5/2004 |
| EP | 2573554 A1 | 3/2013 |
| JP | 62-194673 A | 8/1987 |
| JP | 6437640 A | 2/1989 |
| JP | 04-302151 A | 10/1992 |
| JP | H04302151 A | 10/1992 |
| JP | H0774337 A | 3/1995 |
| JP | 10283230 A | 10/1998 |
| JP | 2003507026 A | 2/2003 |
| JP | 2003090815 A | 3/2003 |
| JP | 2003332555 A | 11/2003 |
| JP | 2003533676 A | 11/2003 |
| JP | 2004233356 A | 8/2004 |
| JP | 2004247203 A | 9/2004 |
| JP | 2004303162 A | 10/2004 |
| JP | 2005501234 A | 1/2005 |
| JP | 2005257687 A | 9/2005 |
| JP | 2006078491 A | 3/2006 |
| JP | 2006526777 A | 11/2006 |
| JP | 2007272212 A | 10/2007 |
| JP | 2008032529 A | 2/2008 |
| JP | 2008146538 A | 6/2008 |
| JP | 4128573 B2 | 7/2008 |
| JP | 2008186975 A | 8/2008 |
| JP | 2008536124 A | 9/2008 |
| JP | 4289938 B2 | 7/2009 |
| JP | 2009527817 A | 7/2009 |
| JP | 2009210272 A | 9/2009 |
| JP | 2009272432 A | 11/2009 |
| JP | 2010510476 A | 4/2010 |
| JP | 2010513853 A | 4/2010 |
| JP | 2010227735 A | 10/2010 |
| JP | 2011500025 A | 1/2011 |
| JP | 2011054631 A | 3/2011 |
| JP | 2011516050 A | 5/2011 |
| JP | 4719906 B2 | 7/2011 |
| JP | 2011163934 A | 8/2011 |
| JP | 2011211905 A | 10/2011 |
| JP | 2012110258 A | 6/2012 |
| JP | 2012118709 A | 6/2012 |
| JP | 2013036865 A | 2/2013 |
| JP | 2013090576 A | 5/2013 |
| JP | 2013518283 A | 5/2013 |
| JP | 2013519074 A | 5/2013 |
| JP | 2013215725 A | 10/2013 |
| JP | 2014074599 A | 4/2014 |
| JP | 2014173936 A | 9/2014 |
| JP | 2015059824 A | 3/2015 |
| JP | 2015077652 A | 4/2015 |
| KR | 1020140031559 | 3/2014 |
| TW | 200619614 A | 6/2006 |
| TW | 200637916 A | 11/2006 |
| TW | 200907068 A | 2/2009 |
| TW | 201013179 A | 4/2010 |
| TW | 201100796 A | 1/2011 |
| WO | WO-0113088 A1 | 2/2001 |
| WO | WO-0181896 A1 | 11/2001 |
| WO | WO-0181908 A1 | 11/2001 |
| WO | WO-03018484 A1 | 3/2003 |
| WO | WO-03042396 A2 | 5/2003 |
| WO | WO-03106693 A2 | 12/2003 |
| WO | WO-2007013370 A1 | 2/2007 |
| WO | WO-2008071982 A2 | 6/2008 |
| WO | WO-2008071982 A3 | 7/2008 |
| WO | WO-2008079169 A2 | 7/2008 |
| WO | WO-2009045472 A1 | 4/2009 |
| WO | WO-2009093019 A2 | 7/2009 |
| WO | WO-2009120642 A1 | 10/2009 |
| WO | WO-2009149362 A2 | 12/2009 |
| WO | WO-2010111605 A2 | 9/2010 |
| WO | WO-2010116595 A1 | 10/2010 |
| WO | WO-2010111605 A3 | 11/2010 |
| WO | WO-2011082419 A2 | 7/2011 |
| WO | WO-2011097171 A1 | 8/2011 |
| WO | WO-2011108540 A1 | 9/2011 |
| WO | WO-2012009578 A2 | 1/2012 |
| WO | WO-2012009578 A3 | 4/2012 |
| WO | WO-2012164679 A1 | 12/2012 |
| WO | WO-2012170560 A1 | 12/2012 |
| WO | WO-2013016486 A1 | 1/2013 |
| WO | WO-2013066456 A2 | 5/2013 |
| WO | WO-2013074546 A1 | 5/2013 |
| WO | WO-2013076943 A1 | 5/2013 |
| WO | WO-2013066456 A3 | 7/2013 |
| WO | WO-2013100949 A1 | 7/2013 |
| WO | WO-2013115185 A1 | 8/2013 |
| WO | WO-2013116509 A1 | 8/2013 |
| WO | WO-2013147208 A1 | 10/2013 |
| WO | WO-2014027580 A1 | 2/2014 |
| WO | WO-2014084931 A1 | 6/2014 |
| WO | WO-2015028885 A2 | 3/2015 |
| WO | WO-2015028886 A2 | 3/2015 |
| WO | WO-2015042200 A1 | 3/2015 |
| WO | WO-2015028885 A3 | 4/2015 |
| WO | WO-2015057870 A1 | 4/2015 |
| WO | WO-2015028886 A3 | 5/2015 |
| WO | WO-2015111760 A1 | 7/2015 |
| WO | WO-2015125920 A1 | 8/2015 |
| WO | WO-2015167019 A1 | 11/2015 |
| WO | WO-2015170782 A1 | 11/2015 |
| WO | WO-2015170783 A1 | 11/2015 |
| WO | WO-2015170784 A1 | 11/2015 |
| WO | WO-2016206593 A1 | 12/2016 |
| WO | WO-2017061129 A1 | 4/2017 |
| WO | WO-2017179581 A1 | 10/2017 |
| WO | WO-2017189930 A1 | 11/2017 |
| WO | WO-2018025887 A1 | 2/2018 |
| WO | WO-2019065904 A1 | 4/2019 |

OTHER PUBLICATIONS

Co-pending U.S. Appl. No. 16/156,755, filed Oct. 10, 2018.
Co-pending U.S. Appl. No. 16/169,756, filed Oct. 24, 2018.
Co-pending U.S. Appl. No. 16/178,924, filed Nov. 2, 2018.
Co-pending U.S. Appl. No. 16/234,908, filed Dec. 28, 2018.
Ohshiro et al. Supplementary Information for Single-Molecule Electrical Random Resequencing of DNA and RNA. Scientific Reports 2, Article No. 501 (Jul. 10, 2012). 23 pages. doi:10.1038/srep00501.
Tsutsui et al. Electrical Detection of Single-Methylcytosines in a DNA Oligomer. J Am Chem Soc 133(23): 9124-9128 (May 11, 2011). DOI: 10.1021/ja203839e.
Tsutsui et al. Supplementary Information for Identifying Single Nucleotides by Tunneling Current. Nature Nanotechnology 5:286-290 (Mar. 21, 2010). doi: 10.1038/NNANO.2010.42.
Tsutsui et al. Supporting Information for Electrical Detection of Single-Methylcytosines in a DNA Oligomer. J Am Chem Soc 133(23): 9124-9128 (May 11, 2011). DOI: 10.1021/ja203839e.
Feng et al. "Nanopore-based Fourth-generation DNA Sequencing Technology" Genomics, Proteomics & Bioinformatics. 2015; 13(1):4-16, p. 5, col2, para 3.

(56) References Cited

OTHER PUBLICATIONS

Fuller et al. "Real-time single-molecule electronic DNA sequencing by synthesis using polymer-tagged nucleotides on a nanopore array" PNAS, Mar. 18, 2016 (Mar. 18, 2016); 113(19):5233-5238 (doi: 10.1073/pnas.1601782113) p. 5234, col. 1, para 1-3; p. 5235, col. 1, para 1; p. 5236, col. 1, para 1; Fig. 2.
Schreiber et al. "Error rates for nanopore discrimination among cytosine, methylcytosine, and hydroxymethylcytosine along individual DNA strands" PNAS, 2013; 11 0(47): 18910-18915, p. 18910, col. 2, para 3.
Armbrust et al. Clearing the clouds away from the true potential and obstacles posed by this computing capability. Communications of the ACM 53(4):50-58 (Apr. 2010).
EP14845728.6 Extended European Search Report dated Apr. 5, 2017.
Furuhashi et al. Denaturation of DNAs in a nanofluidic channel by micro-heating method. The 74th Annual Meeting of the Japan Society of Applied Physics Lecture Papers p. 12-295 (Aug. 2013).
Furuhashi et al. Denature of double-stranded DNAs by a micro-heating method. Proceedings of the 60th Spring Science Lecture Meeting of the Japan Society of Applied Physics, p. 12-356, (Mar. 2013).
Garcia-Lekue et al. Plane-wave-based electron tunneling through Au nanojunctions: Numerical calculations. Physical Review B 82:035410 (2010). 9 pages.
Healy et al. Fabrication and characterization of nanopores with insulated transverse nanoelectrodes for DNA sensing in salt solution. Electrophoresis 33(23) (Dec. 2012). doi: 10.1002/elps.201200350. 15 pages.
PCT/US2014/056173 International Preliminary Report on Patentability dated Mar. 22, 2016.
Chen, et al., A novel nanofabrication technique for the array of Nanogap electrodes, Japanese Journal of Applied Physics, Japan Society of Applied physics, JP, 2006, 45(6):5531-5534.
El-Ali, et al., Simulation and experimental validation of a SU-8 based PCR themorcycler chp with integrated heaters and temperature sensor, Sensors and Actuators A, 110, 2004, pp. 3-10.
Hashioka, et al, Metal nanogap devices fabricated by conventional photolithography and their application to deoxyribose nucleic acid analysis, Journal of Vacuum Science & Technology B: microelectronics; Materials, Processing and Phenomena, 2003, 21(6):2937-40.
Tsutsui, et al., Formation and self-breaking mechanism of stable atom-sized junctions, NANO Letters, 2008, 8(1):345-349.
Bagci, et al. Recognizing nucelotides by cross-tunneling currents for DNA sequencing. Physical Review E, vol. 84, Issue No. 1, Article No. 011917 (internal pp. 1-4) (2011).
Branton, et al. The potential and challenges of nanopore sequencing. Nature Biotechnology, vol. 26, No. 10, Oct. 2008, pp. 1146-1153.
Brown, et al. Nucleotide-Surface Interactions in DNA-Modified Au-Nanoparticle Conjugates: Sequence Effects on Reactivity and Hybridization. J. Phys. Chem. C, 2008, 112 (20), pp. 7517-7521.
Carter, et al. Voltammetric studies of the interaction of metal chelates with DNA. 2. Tris-chelated complexes of cobalt (III) and iron (II) with 1, 10-phenanthroline and 2, 2'-bipyridine. Journal of the American Chemical Society 111.24 (1989): 8901-8911.
Chang, et al. Tunnelling readout of hydrogen-bonding-based recognition. Nature Nantechnology, vol. 4, May 2009, pp. 297-301.
Cheng, et al. Development of an electrochemical membrane-based nanobiosensor for ultrasensitive detection of dengue virus. Anal Chim Acta. May 6, 2012;725:74-80. doi: 10.1016/j.aca.2012.03.017. Epub Mar. 17, 2012.
Clarke, et al. Continuous base identification for single-molecule nanopore DNA sequencing. Nat Nanotechnol. Apr. 2009;4(4):265-70. doi: 10.1038/nnano.2009.12. Epub Feb. 22, 2009.
Co-pending U.S. Appl. No. 14/883,494, filed Oct. 14, 2015.
Co-pending U.S. Appl. No. 15/242,221, filed Aug. 19, 2016.
Co-pending U.S. Appl. No. 15/336,515, filed Oct. 27, 2016.
Co-pending U.S. Appl. No. 15/340,584, filed Nov. 1, 2016.
Co-pending U.S. Appl. No. 15/344,184, filed Nov. 4, 2016.

Co-pending U.S. Appl. No. 15/344,199, filed Nov. 4, 2016.
Dekker, et al. Solid-state nanopores. Nature Nanotechnology, vol. 2, Apr. 2007, pp. 209-215.
European search report and opinion dated Apr. 8, 2016 for EP Application No. 13879507.5.
Fischbein, et al. Sub-10 nm Device Fabrication in a Transmission Electron Microscope. American Chemical Society, Nano Letters, 2007, vol. 7, No. 5, pp. 1329-1337.
Fologea, et al. Detecting Single Stranded DNA with a Solid State Nanopore. American Chemical Society, Nano Letters, 2005, vol. 5, No. 10, pp. 1905-1909.
Furuhashi, et al. High speed DNA denaturation using microheating devices. Appl. Phys. Lett., Jul. 11, 2013, 103, pp. 023112.
Gierhart, et al. Nanopore with transverse nanoelectrodes for electrical characterization and sequencing of DNA. Sens Actuators B Chem. Jun. 16, 2008;132(2):593-600.
Gonzalez, et al. Mass transport effect of mesoscopic domains in the amperometric response of an electroactive species: Modeling for its applications in biomolecule detection. Sensors and Actuators B: Chemical 144.2 (2010): 349-353.
He, et al. Controlling DNA translocation through gate modulation of nanopore wall surface charges. ACS Nano. Jul. 26, 2011;5(7):5509-18. doi: 10.1021/nn201883b. Epub Jun. 17, 2011.
He, et al. Gate manipulation of DNA capture into nanopores. ACS Nano. Oct. 25, 2011;5(10):8391-7. doi: 10.1021/nn203186c. Epub Sep. 26, 2011.
He, et al. Identification of DNA Basepairing via Tunnel-Current Decay. American Chemical Society, Nano Letters, 2007, vol. 7, No. 12, pp. 3854-3858.
He, et al. Thermophoretic manipulation of DNA translocation through nanopores. ACS Nano. Jan. 22, 2013;7(1):538-46. doi: 10.1021/nn304914j. Epub Dec. 10, 2012.
"Huang, et al. Identifying single bases in a DNA oligomer with electron tunnelling. Nat Nanotechnol. Dec. 2010;5(12):868-73. doi: 10.1038/nnano.2010.213. Epub Nov. 14, 2010."
International Preliminary Report on Patentability dated Jun. 25, 2013 for PCT Application No. JP2013/059645.
International search report and written opinion dated Jan. 26, 2015 for PCT Application No. US2014/060742.
International search report and written opinion dated May 19, 2015 for PCT/JP2015/054796.
International search report and written opinion dated Jun. 24, 2015 for PCT/JP2015/052601.
International search report and written opinion dated Aug. 11, 2015 for PCT/JP2015/063403.
International search report and written opinion dated Aug. 18, 2015 for PCT/JP2015/063963.
International search report and written opinion dated Aug. 18, 2015 for PCT/JP2015/063964.
International search report and written opinion dated Aug. 18, 2015 for PCT/JP2015/063965.
International search report and written opinion dated Oct. 29, 2013 for PCT Application No. PCT/JP2013/071059.
International search report and written opinion dated Dec. 19, 2014 for PCT Application No. PCT/US2014/056173.
International search report dated Feb. 17, 2015 for PCT Application No. PCT/IB2014/002143.
International search report dated Feb. 24, 2015 for PCT Application No. PCT/IB2014/002128.
International search report dated Jun. 25, 2013 for PCT Application No. PCT/JP2013/059645.
Ivanov, et al. DNA tunneling detector embedded in a nanopore. Nano Lett. Jan. 12, 2011;11(1):279-85. doi: 10.1021/nl103873a. Epub Dec. 6, 2010.
Kaji, et al. Separation of long DNA molecules by quartz nanopillar chips under a direct current electric field. Anal. Chem., Jan. 1, 2004, 76(1): pp. 15-22.
Keyser, et al. Direct force measurements on DNA in a solid-state nanopore. Nature Physics, vol. 2, Jul. 2006, pp. 473-477.
Lagerqvist, et al. "Fast DNA Sequencing via Transverse Electronic Transport", American Chemical Society, Nano Letters, 2006, vol. 6, No. 4, pp. 779-782.

(56) References Cited

OTHER PUBLICATIONS

Lagerqvist, et al. Influence of the Environment and Probes on Rapid DNA Sequencing via Transverse Electronic Transport. Biophysical Journel, vol. 93, Oct. 2007, pp. 2384-2390.

Lee, et al. Surface charge study on pollen with a simple microelectrophoresis instrumentation setup. Biomedical Engineering and Sciences (IECBES), 2010 IEEE EMBS Conference on. Kuala Lumpur, Malaysia, Nov. 30-Oct. 2, 2010, pp. 364-368.

Lesser-Rojas, et al. Tandem array of nanoelectronic readers embedded coplanar to a fluidic nanochannel for correlated single biopolymer analysis. Biomicrofluidics. Jan. 10, 2014;8(1):016501. doi: 10.1063/1.4861435. eCollection 2014. With Supplementary Materials.

Li, et al. Ion-beam sculpting at nanometer length scales. Nature, vol. 412, Jul. 2001, pp. 166-169.

Liang, et al. Nanogap Detector Inside nanofluidic Channel for Fast Real-Time Label-Free DNA Analysis. American Chemical Society, Nano Letters 2008, vol. 8, No. 5, pp. 1472-1476.

Maleki, et al. A nanofluidic channel with embedded transverse nanoelectrodes. Nanotechnology, 20, (2009) 105302, pp. 1-6.

Nadasan, et al. Design and fabrication of the microchannels for microfluidics applications. U.P.B. Sci. Bull., Series C, 2009, 71(4): pp. 125-134.

Nam, et al. Ionic field effect transistors with sub-10 nm multiple nanopores. Nano Lett. May 2009;9(5):2044-8. doi: 10.1021/nl900309s.

Notice of allowance dated Jul. 17, 2015 for U.S. Appl. No. 13/992,328.
Notice of allowance dated Jul. 21, 2016 for U.S. Appl. No. 13/975,610.
Notice of allowance dated Sep. 15, 2016 for U.S. Appl. No. 14/421,809.
Notice of allowance dated Oct. 8, 2015 for U.S. Appl. No. 13/992,328.
Notice of Allowance dated Dec. 6, 2016 for U.S. Appl. No. 15/061,871.
Office action dated Feb. 5, 2016 for U.S. Appl. No. 14/112,189.
Office action dated Feb. 19, 2016 for U.S. Appl. No. 13/975,610.
Office action dated Apr. 17, 2015 for U.S. Appl. No. 13/992,328.
Office action dated May 25, 2016 for U.S. Appl. No. 14/421,809.
Office action dated Jun. 23, 2016 for U.S. Appl. No. 14/111,352.
Office action dated Aug. 1, 2016 for U.S. Appl. No. 14/112,189.
Office action dated Sep. 1, 2015 for U.S. Appl. No. 14/112,189.
Office action dated Sep. 9, 2016 for U.S. Appl. No. 15/061,871.
Office action dated Oct. 6, 2016 for U.S. Appl. No. 14/883,494.

Ohshiro, et al. Single-molecule electrical random resequencing of DNA and RNA. Scientific Reports 2, Article No. 501 (Jul. 10, 2012) doi:10.1038/srep00501.

Oshiro, et al. Detection of post-translational modifications in single peptides using electron tunnelling currents. Nature Nanotechnology, vol. 9, pp. 835-840 (e-pub. Sep. 14, 2014).

Oshiro, et al. Single-molecule electrical random resequencing of DNA and RNA. Scientific Reports, vol. 2, Article No. 501 (internal pp. 1-7) (e-pub. Jul. 10, 2012) See abstract: p. 2; figures 1-4; and tables 1-3.

Pedone, et al. Data Analysis of Translocation Events in Nanopore Experiments. American Chemical Society, Anal. Chem. 2009, 81, pp. 9689.

Peng, et al. Reverse DNA translocation through a solid-state nanopore by magnetic tweezers. Nanotechnology. May 6, 2009;20(18):185101. doi: 10.1088/0957-4484/20/18/185101. Epub Apr. 14, 2009.

Qiu, et al. Detecting ssDNA at single-nucleotide resolution by sub-2-nanometer pore in monoatomic graphene: A molecular dynamics study. Applied Physics Letters 100.8 (2012): 083106. 4 pages.

Rothberg, J.M. et al., An integrated semiconductor device enabling non-optical genome sequencing, Nature. 2011. 475(7356). pp. 348-352.

Ruitenbeek, et al. Adjustable nanofabricated atomic size contacts. Rev. Sci. Instrum. 67, 108 (1996).

Simmons, et al. Generalized Formula for the Electric tunnele Effect between Similar Electrodes Separated by a Thin Insulating Film. J. Appl. Phys. 34, 1793 (1963).

Smith, et al. Electrophoretic distributions of human peripheral blood mononuclear white cells from normal subjects and from patients with acute lymphocytic leukemia. Proc Natl Acad Sci U S A. Jul. 1976;73(7):2388-91.

Stijin Van Dorp, et al. Origin of the electrophoretic force on DNA in solid-state nanopores. Nature Physics, vol. 5, May 2009, pp. 347-351.

Stoddart, et al. Single-nucleotide discrimination in immobolized DNA oligonucleotides with a biological nanopore. PNAS, May 12, 2009, vol. 106, No. 19, pp. 7702-7707.

Storm, et al. Fabrication of solid-state nanopores with single-nanometere precision. Nature Materials, vol. 2, Aug. 2003, pp. 537-540.

Taniguchi, et al. Denryu de Ichi Enki Bunshi o Shikibetsu suru. Chemistry, 2011, vol. 66, No. 8, pp. 42-46.

Taniguchi, et al. Development of Single-Molecule Bio-Nanodevies for Medical Applications. The Imaging Society of Japan, Feb. 10, 2013, vol. 52, No. 1, pp. 51-60.

Taniguchi, M. Ichibunshi Kaiseki Gijutsu ni yoru Jijisedai DNA Sequencer no Kaihatsu. Dai 69 Kai Hyomen Kagaku Kenkyukai Yoshishu. Mar. 9, 2011, pp. 23-26.

Trepagnier, et al. Controlling DNA Capture and Progagation through Artificial Nanopores. American Chemical Society, Nano Letters, 2007, vol. 7, No. 9, pp. 2824-2830.

"Troisi, et al. Molecular signatures in the transport properties of molecular wire junctions: what makes a junction "molecular"? Small. Feb. 2006;2(2):172-81."

Tsutsui, et al. Fabrication of 0.5 nm electrode gaps using self-breaking technique. Applied Physics Letters 93, 163115 (2008); DOI: 10.1063/1.3006063.

Tsutsui, et al. Formation and self-breaking mechanism of stable atom-sized junctions. Nano Lett. Jan. 2008;8(1):345-9. Epub Dec. 21, 2007.

Tsutsui, et al. Identifying single nucleotides by tunnelling current. Nature Nanotechnology, Letters, Published Online: Mar. 21, 2010; DOI: 10.1038/NNANO.2010.42, pp. 1-5.

Tsutsui, et al. Transverse electric field dragging of DNA in a nanochannel. Sci Rep. 2012;2:394. doi: 10.1038/srep00394. Epub May 3, 2012.

Tsutsui, et al. Transverse Field Effects on DNA-Sized Particle Dynamics. American Chemical Society, Nano Letters, 2009, vol. 9, No. 4, pp. 1659-1662.

Venkatesan, et al. Nanopore sensors for nucleic acid analysis. Nat Nanotechnol. Sep. 18, 2011;6(10):615-24. doi: 10.1038/nnano.2011.129.

Wang, et al. Mechanism of electron conduction in self-assembled alkanethiol monolayer devices. Phys. Rev. B 68, 035416—Published Jul. 17, 2003.

Woolley, et al. Capillary electrophoresis chips with integrated electrochemical detection.. Analytical Chemistry 70.4 (1998): 684-688.

Yen, et al. Gate effects on DNA translocation through silicon dioxide nanopore. Rev Sci Instrum. Mar. 2012;83(3):034301. doi: 10.1063/1.3692746.

Zhao, et al. Single-strand DNA molecule translocation through nanoelectrode gaps. Nanotechnology. Oct. 24, 2007;18(42):424018. doi: 10.1088/0957-4484/18/42/424018. Epub Sep. 19, 2007. 7 pages.

Zhou, et al. Microfabrication of a mechanically controllable break junction in silicon. Appl. Phys. Lett. 67, 1160 (1995).

Zwolak, et al. Colloquium: Physical approaches to DNA sequencing and detection. Reviews of Modern Physics, vol. 80, Jan.-Mar. 2008, pp. 141-165.

Zwolak, et al. Electronic Signature of DNA Nucleotides via Transverse Transport. American Chemical Society, Nano Letters, 2005, vol. 5, No. 3, pp. 421-424.

Co-pending U.S. Appl. No. 15/937,327, filed Mar. 27, 2018.

Suga et al. Influence of electrode size on resistance switching effect in nanogap junctions, Applied Physics Letter, 2010, 97(7):73118, 4 pages. Epub Aug. 20, 2010.

Axopatch 2008 Patch Clamp: Theory and Operation, Axon Instruments, Inc., Mar. 1999.

Chen, et al., Probing Single DNA Molecule Transport Using Fabricated Nanopores, Nano Letters, 2004, 4(11):2293-2298.

(56) References Cited

OTHER PUBLICATIONS

Taniguchi et al. Fabrication of the gating nanopore device. Applied Physics Letters 95:123701 (2009). 4 pages. DOI: https://doi.org/10.1063/1.3236769.

Co-pending U.S. Appl. No. 16/266,363, filed Feb. 4, 2019.

Ohshiro et al. Tunnel-Current based Single-Molecule Identification of DNA/RNA oligmer by using Nano-MCBJ. 2012 12th IEEE International Conference on Nanotechnology (IEEE-NANO), Birmingham, United Kingdom, (Aug. 20-23, 2012). 2 pages.

Tang et al. Sub-10-nm nanogap fabrication by silicidation. 2013 13th IEEE International Conference on Nanotechnology (IEEE-NANO 2013). (Aug. 5-8, 2013). 4 pages. DOI: 10.1109/NANO.2013.6720811.

EP19171865.9 Extended European Search Report dated Oct. 24, 2019.

\* cited by examiner

| Kind of monomolecule | Relative conductance |
|---|---|
| G | 0.5 |
| A | 0.3 |
| C | 0.2 |
| T | 0.1 |

| Distance between electrodes | Kind of monomolecule | Relative conductance |
|---|---|---|
| d1 | Trp | 0.5 |
| | Tyr | 0.3 |
| d2 | Thr | 0.5 |
| | His | 0.3 |
| d3 | Phe | 0.5 |
| | Pro | 0.3 |
| | Cys | 0.1 |

Fig. 13

BIOMOLECULE SEQUENCING DEVICES, SYSTEMS AND METHODS

CROSS-REFERENCE

This application is a continuation of U.S. patent application Ser. No. 15/061,871, filed Mar. 4, 2016, now U.S. Pat. No. 9,644,236, which is a continuation of International Patent Application No. PCT/US2014/056173, filed Sep. 17, 2014, which claims priority to Japanese Patent Application Serial No. JP 2013-193498, filed Sep. 18, 2013, and JP 2013-197443, filed Sep. 24, 2013, each of which is entirely incorporated herein by reference.

BACKGROUND

There are methods currently available to identify one or more monomers of a biomolecule. Monomers may comprise elements of biomolecules, such as amino acid monomers which are included in a protein, nucleotide monomers which are included in a nucleic acid, and monosaccharide monomers which are included in a sugar chain. As a monomer identifying method, there are identification methods using monomer measurement where light or electricity is used as a probe signal, for example. In a monomer identifying method using monomer measurement, a specific monomer can be detected by modifying a target sample with a fluorescent molecule or a probe molecule having electroactivity. For example, sequences for proteins have been determined by using various methods, such as high performance liquid chromatography (HPLC) based on enzymatic degradation, mass spectrometry, X-ray crystal structure analysis, and Edman degradation, for example.

However, the aforementioned methods for detecting a monomer by modifying the sample with a probe molecule have problems in that a chemical modification may be required and that the efficiency with any such modification may be insufficient. Moreover, the aforementioned methods can only detect specific chemical species and may not be applied to a biomolecule sequencing process conducted using a bio-sample containing various molecular species.

SUMMARY

In a monomer identifying method using a nano current measurement using nanogap electrode pairs, such as tunneling current measurement, since a measurement result may vary depending on measurement method and/or measuring conditions, it may be necessary to standardize measured signals. Thus, by applying a standardization method as described in, for example, JP2011-163934A and JP2008-32529A, which are entirely incorporated herein by reference, to a biomolecule sequencing system using tunneling current measurement, wherein a relative conductance utilizing a sample molecule itself to serve as an internal reference substance (or reference sample), indirect standardization of measured signals can be conducted.

However, in order to sufficiently measure the internal reference substance, a time for measurement is elongated. In addition, the above-described standardization may not be applied to a sample containing an unknown molecule. Thus, when a sample containing an unknown molecule is measured or detected, a separation step, refinement step or the like may be used. When a conventional standardization method is applied to a nano current measurement using a nanogap electrode device, samples and conditions may be limited.

The present disclosure provides methods, apparatuses and computer programs that may be useful for the identification of monomers in biomolecules (e.g., biomolecular polymers) and sequencing of biomolecules. Some embodiments include a method to provide standardized biomolecule sequencing, an apparatus and a computer program ("program") which are capable of, for a sample containing an unknown molecule, identifying a monomer utilizing a nano current measurement using nanogap electrodes, without needing a step such as a separation step, a refinement step or the like.

Devices, systems and methods provided herein are capable of identifying various kinds of monomer using highly sensitive measured signals, which may be standardized.

In some cases, a biomolecule sequencing method may include measuring signals corresponding to nano currents (e.g., tunneling currents) that flow when a reference substance and at least one or more kinds of monomer to be identified, which may be contained in a sample, may be respectively passed through between electrodes of a nanogap electrode pair. The sample may include a reference substance added thereto and one or more kinds of monomer to be identified, for which the magnitude of a signal of a reference substance, which corresponds to a nano current that flows between the electrodes of a nanogap electrode pair when a reference substance passes through between the electrodes of a nanogap electrode pair, is known, and a variation of the magnitude of the signal falls within a predetermined variation range; and identifying, by using as a reference a signal indicating a reference substance which may be included in a plurality of measured signals, a kind of monomer may be indicated by an additional signal included in a plurality of signals.

Thus, even in a case wherein a nano current measurement method using nanogap electrode pair(s) in which a measurement result may vary depending on measuring method and measuring conditions, a stable signal indicating a reference substance can be obtained. Thus, standardization can be conducted such that, for a sample containing an unknown molecule, biomolecule sequencing utilizing a nano current measurement using nanogap electrode pair(s) can be carried out without needing a step such as a separation step, a refinement step or the like.

In addition, a reference substance may have electric conductivity, a reference substance may not need to be combined with the monomer to be identified, and a reference substance may be composed of compounds of the same shape regardless of orientation. Thus, it is possible to obtain a signal indicating a reference substance, which can be easily differentiated from a signal indicating a monomer to be identified.

In addition, a reference substance may be composed of matters which have the same positional orientation with respect to a space between the electrodes of a nanogap electrode pair(s) when a reference substance is passed through between the electrodes of a nanogap electrode pair(s). Thus, the magnitudes of signals indicating reference substance(s) for different measurements can be made to appear uniform.

In addition, a reference substance may be composed of compounds with a spherical shape. Thus, regardless of the structure of the electrodes, magnitudes of signals indicating a reference substance for different measurements can be made to appear uniform.

In addition, a reference substance may comprise metal nanoparticles or fullerenes.

In addition, a concentration of the reference substance with respect to the sample may be optimized such that a rate of the signal indicating the reference substance with respect to the plurality of signals falls within a predetermined rate range. Thus, a signal indicating the reference substance can be stably detected, and the signal indicating the reference substance can be prevented from giving rise to a noise.

In addition, when identifying a kind of the monomer, a kind of the monomer indicated by the further signal may be identified based on relative values of the plurality of signals with respect to the signal indicating the reference substance, and a predetermined relationship between the kind of the monomer and the relative values of the signals.

In addition, when measuring signals corresponding to nano currents, signals corresponding to the nano currents may be measured for each of a plurality of conditions with different distances between electrodes of a nanogap electrode pair(s), for a sample containing a plurality of different reference substances which may be identifiable with a plurality of different distances between electrodes of nanogap electrode pair(s); and when identifying a kind of monomer, a signal indicating a reference substance corresponding to a relevant condition and an additional signal, which may be included in the plurality of measured signals, may be compared to each other for each condition, and the kind of monomer indicated by the additional signal may be identified based on a comparison resulting from each condition. Thus, a more precise identification can be carried out.

In addition, a biomolecule sequencing apparatus as described herein may include: a pair of electrodes of a nanogap electrode pair(s) located such that a nano current flows when a sample is passed through between the electrodes of a nanogap electrode pair(s), the sample may include a reference substance added thereto and may include at least one or more kinds of monomer to be identified, for which a magnitude of a signal associated with a reference substance, which corresponds to a nano current that may flow between the electrodes of a nanogap electrode pair(s) when a reference substance may be passed through between the electrodes of a nanogap electrode pair(s), is known, and a variation of a magnitude of a signal falls within a predetermined variation range; a measuring unit configured to measure signals corresponding to nano currents that flow when a reference substance and a monomer to be identified, which may be contained in a sample, may be respectively passed through between the electrodes of a nanogap electrode pair(s); and an identification unit configured to identify, using as a reference a signal indicating a reference substance which may be included in a plurality of measured signals measured by a measuring unit, a kind of the monomer indicated by an additional signal contained in a plurality of signals.

In addition, a biomolecule sequencing program may be executed by a computer to perform: measuring signals corresponding to nano currents that flow when a reference substance and at least one or more kinds of monomer to be identified, which may be contained in a sample, may be respectively passed through between electrodes of a nanogap electrode pair(s), a sample may include a reference substance added thereto and may include one or more kinds of monomer to be identified, for which magnitude of a signal of a reference substance, which corresponds to a nano current that flows between electrodes of a nanogap electrode pair(s) when a reference substance may be passed through between the electrodes of a nanogap electrode pair(s), is known, and a variation of magnitude of a signal falls within a predetermined variation range; and identifying, by using as a reference a signal indicating a reference substance which may be included in a plurality of measured signals, a kind of the monomer indicated by a further signal included in the plurality of signals.

In some embodiments, a biomolecule sequencing apparatus includes an electrode pair disposed such that a tunneling current may flow when a biomolecule comprising at least one or more kinds of monomers bound so as to form the biomolecule passes through between electrodes of an electrode pair; a measuring unit configured to measure a tunneling current generated when a biomolecule passes through between the electrodes of a nanogap electrode pair multiple times wherein different passages between the electrodes of an nanogap electrode pair may have different spacing(s) for the electrodes of the nanogap electrode pair; and an identification unit to identify at least one kind of monomer comprising a biomolecule based on a reference physical quantity of at least one known kind of monomer obtained from a tunneling current measured with an inter-electrode distance for which each of multiple kinds of monomers is identifiable with predetermined accuracy and based on a detected physical quantity obtained from a tunneling current measured by the measuring unit with an inter-electrode distance corresponding to a reference physical quantity.

In some embodiments, an electrode pair may be disposed such that a tunneling current may flow when a biomolecule comprising at least one or more kinds of monomers bound so as to form the biomolecule passes through between electrodes of a nanogap electrode pair. A measuring unit may measure a tunneling current generated when a biomolecule passes between the electrodes of an electrode pair wherein the nanogap pair may have multiple electrode gap spacings over time.

An identification unit may identify at least one kind of monomers comprising a biomolecule based on a reference physical quantity of at least one known kind of monomers obtained from a tunneling current measured with an inter-electrode distance for which multiple kinds of monomers may be identifiable with a predetermined accuracy based on a detected physical quantity obtained from a tunneling current measured by a measuring unit with an inter-electrode distance corresponding to the reference physical quantity.

As mentioned above, by measuring a tunneling current generated when a biomolecule passes multiple times between an electrode pair using multiple inter-electrode distances, and by using a reference physical quantity of at least one known kind of monomers obtained from a tunneling current measured using an inter-electrode distance for which each of multiple kinds of monomers may be identifiable with a predetermined accuracy, monomers comprising a biomolecule may be identified with a simple configuration and with high accuracy.

A biomolecule may include biopolymers such as proteins, peptides, nucleic acids, and sugar chains. Further, monomers comprising a biomolecule may include amino acids comprising proteins or peptides, nucleotides comprising nucleic acids, ribonucleotides comprising ribonucleic acids, and monosaccharides comprising sugar chains.

A biomolecule sequencing apparatus may further include a control unit configured to control an electrode pair such that by changing an inter-electrode distance of an electrode pair, a biomolecule may be detected better. Thus, by using a single electrode pair, tunneling currents using multiple different inter-electrode distances may be measured and utilized to characterize a biomolecule.

A biomolecule sequencing apparatus may utilize multiple electrode pairs each having a different inter-electrode distance. Thus, tunneling currents from different electrodes provide different information wherein each electrode may have a different inter-electrode distance, allowing measurement of different inter-electrode distances simultaneously.

In addition, an identification unit may identify, based on a detected physical quantity obtained from a tunneling current measured using an inter-electrode distance that is different from a predetermined inter-electrode distance, a kind of monomer(s) which could not be identified based on a detected physical quantity obtained from a tunneling current measured using a predetermined inter-electrode distance.

Regarding a detected physical quantity and a reference physical quantity, various values, such as current values and conductances of a tunneling current, may be used. If voltage applied to the electrode pair is constant, current values and the conductances associated with tunneling current may both be equally utilized.

A biomolecule sequencing method can include measuring a tunneling current generated when a biomolecule having at least one or more kinds of connected monomers passes through between electrodes of an electrode pair which is disposed such that the tunneling current may flow when a biomolecule passes through between the electrodes of an electrode pair multiple times, wherein at least some of the different times have a different inter-electrode distance for an electrode pair; and identifying at least one kind of monomers comprising a biomolecule based on a reference physical quantity for at least one known kind of monomers obtained from a tunneling current measured with an inter-electrode distance for which each of multiple kinds of monomers may be identifiable with a predetermined accuracy and based on a detected physical quantity obtained from a tunneling current measured by a measuring unit utilizing an inter-electrode distance corresponding to a reference physical quantity.

A biomolecule sequencing program may be executed by a computer to measure a tunneling current generated when a biomolecule having at least one or more kinds of connected monomers passes through between electrodes of an electrode pair which may be disposed such that tunneling current may flow when a biomolecule passes through between the electrodes of a nanogap electrode pair multiple times, wherein at least some of the different passages through between the nanogap electrode pairs occur while the nanogap electrode pair is set to have different inter-electrode distances for the electrode pair; and identifying at least one kind of monomers comprising a biomolecule based on a reference physical quantity of at least one known kind of monomers obtained from a tunneling current measured with an inter-electrode distance at which each of multiple kinds of monomers may be identifiable with a predetermined accuracy and based on a detected physical quantity obtained from a tunneling current measured by a measuring unit with an inter-electrode distance corresponding to a reference physical quantity.

In some embodiments, a biomolecule sequencing apparatus, method and computer program can be utilized to identify a monomer comprising a biomolecule utilizing a simple configuration and with high accuracy by measuring a tunneling current generated when a biomolecule passes through between electrodes of an electrode pair using multiple different inter-electrode distance, and by using a reference physical quantity of at least one known kind of monomers obtained from a tunneling current measured with an inter-electrode distance for which each of multiple kinds of monomers may be identifiable with a predetermined accuracy.

An aspect of the present disclosure provides a method for sequencing a biomolecule having a plurality of monomers, comprising (a) providing a channel including a plurality of sets of nanogap electrodes, wherein each set of the plurality of sets of nanogap electrodes includes two nanogap electrodes, and wherein at least a subset of the plurality of sets of nanogap electrodes has different inter-electrode distances; (b) directing the biomolecule through the channel; (c) measuring signals with the plurality of sets of nanogap electrodes that correspond to nanocurrents as the biomolecule is directed through the channel, which signals correspond to the plurality of monomers of the biomolecule; and (d) identifying with a computer processor the plurality of monomers by comparing the signals measured in (c) to one or more references.

In an embodiment, the identifying comprises using a given or predetermined relationship between a relative value of the signals and the one or more references. In another embodiment, the plurality of sets of nanogap electrodes comprises a first set of nanogap electrodes and a second set of nanogap electrodes having different inter-electrode gap distances. In another embodiment, the method forther comprises using an inter-electrode distance of a given set of nanogap electrodes to interpolate a nanocurrent for another inter-electrode distance. In another embodiment, the method further comprises generating a consensus sequence of the biomolecule using data from multiple measurements with the plurality of sets of nanogap electrodes using individual monomer quality calls. In another embodiment, the method further comprises measuring signals corresponding to nanocurrents for the plurality of sets of nanogap electrodes at different inter-electrode distances. In another, the method further comprises measuring signals from at most a subset of the plurality of sets of nanogap electrodes, and identifying a given monomer of the plurality of monomers with the signals measured with at most the subset of the plurality of sets of nanogap electrodes. In another embodiment, the nanocurrents include tunneling currents.

In an embodiment, the biomolecule is a peptide sample. In another embodiment, the method further comprises denaturing and/or cleaving the peptide sample prior to (b).

In an embodiment, each set of the sets of nanogap electrodes has an inter-electrode distance that is suitable to detect at most a subset of the plurality of monomers of the biomolecule. In another embodiment, the biomolecule is a nucleic acid molecule.

In another aspect of the present disclosure, a system for sequencing a biomolecule having a plurality of monomers comprises a channel including a plurality of sets of nanogap electrodes, wherein each set of the plurality of sets of nanogap electrodes includes two nanogap electrodes, and wherein at least a subset of the plurality of sets of nanogap electrodes has different inter-electrode distances; a fluid flow unit for directing the biomolecule through the channel; and a computer processor coupled to the nanogap electrodes and programmed to: (a) measure signals with the plurality of sets of nanogap electrodes that correspond to nanocurrents as the biomolecule is directed through the channel, which signals correspond to the plurality of monomers of the biomolecule; and (b) identify the plurality of monomers by comparing the signals measured in (a) to one or more references.

In an embodiment, the computer processor is programmed to identify the plurality of monomers using a predetermined relationship between a relative value of the signals and the one or more references. In another embodiment, the plurality of sets of nanogap electrodes comprises a first set of nanogap electrodes and a second set of nanogap electrodes having different inter-electrode gap distances. In another embodiment, the computer processor is programmed to use an inter-electrode distance of a given set of nanogap electrodes to interpolate a nanocurrent for another inter-electrode distance. In another embodiment, the computer processor is programmed to generate a consensus sequence of the biomolecule using data from multiple measurements with the plurality of sets of nanogap electrodes using individual monomer quality calls. In another embodiment, each set of the sets of nanogap electrodes has an inter-electrode distance that is suitable to detect at most a subset of the plurality of monomers of the biomolecule. In another embodiment, the computer processor is programmed to measure signals corresponding to nanocurrents for the plurality of sets of nanogap electrodes at different inter-electrode distances. In another embodiment, the computer processor is programmed to measure signals from at most a subset of the plurality of sets of nanogap electrodes, and identify a given monomer of the plurality of monomers with the signals measured with at most the subset of the plurality of sets of nanogap electrodes.

Another aspect of the present disclosure provides a method for sequencing a peptide sample having one or more monomers comprises (a) providing a channel including at least one set of nanogap electrodes having an inter-electrode distance that is variable; (b) directing the peptide sample and at least one reference sample through the channel, wherein the reference sample has a predetermined signal profile corresponding to a nanocurrent measured by the nanogap electrodes; (c) measuring signals with the nanogap electrodes at different inter-electrode distances that correspond to nanocurrents as the protein sample and reference sample are directed through the channel, which signals include reference signals associated with the reference sample; and (d) identifying with a computer processor the one or more monomers by comparing the signals measured in (c) to the reference signals.

In an embodiment, the reference sample is separate from the peptide sample. In another embodiment, the reference sample is a reference peptide sample with a predetermined sequence of one or more monomers. In another embodiment, the reference sample comprises subunits that have the same orientation with respect to a space between the nanogap electrodes when the reference sample is passed through between the nanogap electrodes. In another embodiment, the reference sample has a substantially spherical shape. In another embodiment, the reference sample comprises metal nanoparticles or fullerenes. In another embodiment, the identifying comprises using a predetermined relationship between a relative value of the signals and the reference signals.

In an embodiment, the channel comprises a plurality of sets of nanogap electrodes, each set comprising at least two nanogap electrodes. In another embodiment, the plurality of sets of nanogap electrodes comprises a first set of nanogap electrodes and a second set of nanogap electrodes having different inter-electrode gap distances.

In an embodiment, the method further comprises generating a consensus sequence of the peptide sample using data from multiple measurements with the nanogap electrodes using individual monomer quality calls. In another embodiment, the method further comprises providing a plurality of different reference samples corresponding to at least a subset of the plurality of different distances between the nanogap electrodes. In another embodiment, the method further comprises denaturing and/or cleaving the peptide sample prior to (b). In another embodiment, the reference sample is associated with a first pulse duration and the peptide sample is associated with a second pulse duration which is different from the first pulse duration.

In an embodiment, the signal profile comprises a magnitude of a signal. In another embodiment, the magnitude of the signal is a predetermined magnitude. In another embodiment, the peptide sample and the at least one reference sample are alternately and sequentially directed through the channel. In another embodiment, (c) further comprises (i) changing the inter-electrode distance of the nanogap electrodes and (ii) making separate measurements of the signals at the different inter-electrode distances. In another embodiment, the nanocurrents include tunneling currents.

In another aspect of the present disclosure, a system for sequencing a peptide sample having one or more monomers comprises a channel including at least one set of nanogap electrodes having an inter-electrode distance that is variable; a fluid flow unit for directing the peptide sample and at least one reference sample through the channel, wherein the reference sample has a predetermined signal profile corresponding to a nanocurrent measured by the nanogap electrodes; and a computer processor coupled to the nanogap electrodes and programmed to (i) measure signals with the nanogap electrodes at variable inter-electrode distances that correspond to nanocurrents as the peptide sample and reference sample are directed through the channel, and (ii) identify the one or more monomers by comparing the signals measured in (i) to the reference signals.

In an embodiment, the reference sample is a reference peptide sample with a predetermined sequence of one or more monomers. In another embodiment, the computer processor is programmed to identify the one or more monomers using a predetermined relationship between a relative value of the signals and the reference signals.

In an embodiment, the channel comprises a plurality of sets of nanogap electrodes, each set comprising at least two nanogap electrodes. In another embodiment, the plurality of sets of nanogap electrodes comprises a first set of nanogap electrodes and a second set of nanogap electrodes having different inter-electrode gap distances. In another embodiment, the computer processor is programmed to generate a consensus sequence of the peptide sample using data from multiple measurements with the nanogap electrodes using individual monomer quality calls. In another embodiment, the fluid flow system provides the reference sample at a first pulse duration and the protein sample at a second pulse duration which is different from the first pulse duration. In another embodiment, the computer processor is programmed to (i) change the inter-electrode distance of the nanogap electrodes and (ii) making separate measurements of the signals at the different inter-electrode distances.

Another aspect of the present disclosure provides a computer readable medium comprising machine-executable code that, upon execution by one or more computer processors, implements any of the methods above or elsewhere herein.

In some embodiments, a computer readable medium comprises machine executable code that, upon execution by one or more computer processors, implements a method for sequencing a protein sample having one or more amino acid monomers, the method comprising: (a) directing the biomolecule through a channel including a plurality of sets of nanogap electrodes, wherein each set of the plurality of sets of nanogap electrodes includes two nanogap electrodes, and wherein at least a subset of the plurality of sets of nanogap electrodes has different inter-electrode distances; (b) measuring signals with the plurality of sets of nanogap electrodes that correspond to nanocurrents as the biomolecule is directed through the channel, which signals correspond to the plurality of monomers of the biomolecule; and (c) identifying the plurality of monomers by comparing the signals measured in (b) to one or more references.

In some embodiments, a computer readable medium comprises machine executable code that, upon execution by one or more computer processors, implements a method for sequencing a protein sample having one or more amino acid monomers, the method comprising (a) directing the peptide sample and at least one reference sample through a channel including at least one set of nanogap electrodes having an inter-electrode distance that is variable, wherein the reference sample has a predetermined signal profile corresponding to a nanocurrent measured by the nanogap electrodes; (b) measuring signals with the nanogap electrodes at different inter-electrode distances that correspond to nanocurrents as the protein sample and reference sample are directed through the channel, which signals include reference signals associated with the reference sample; and (c) identifying the one or more monomers by comparing the signals measured in (b) to the reference signals.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 13 is a view showing an example of a relative conductance table;

DETAILED DESCRIPTION

Figure 1:
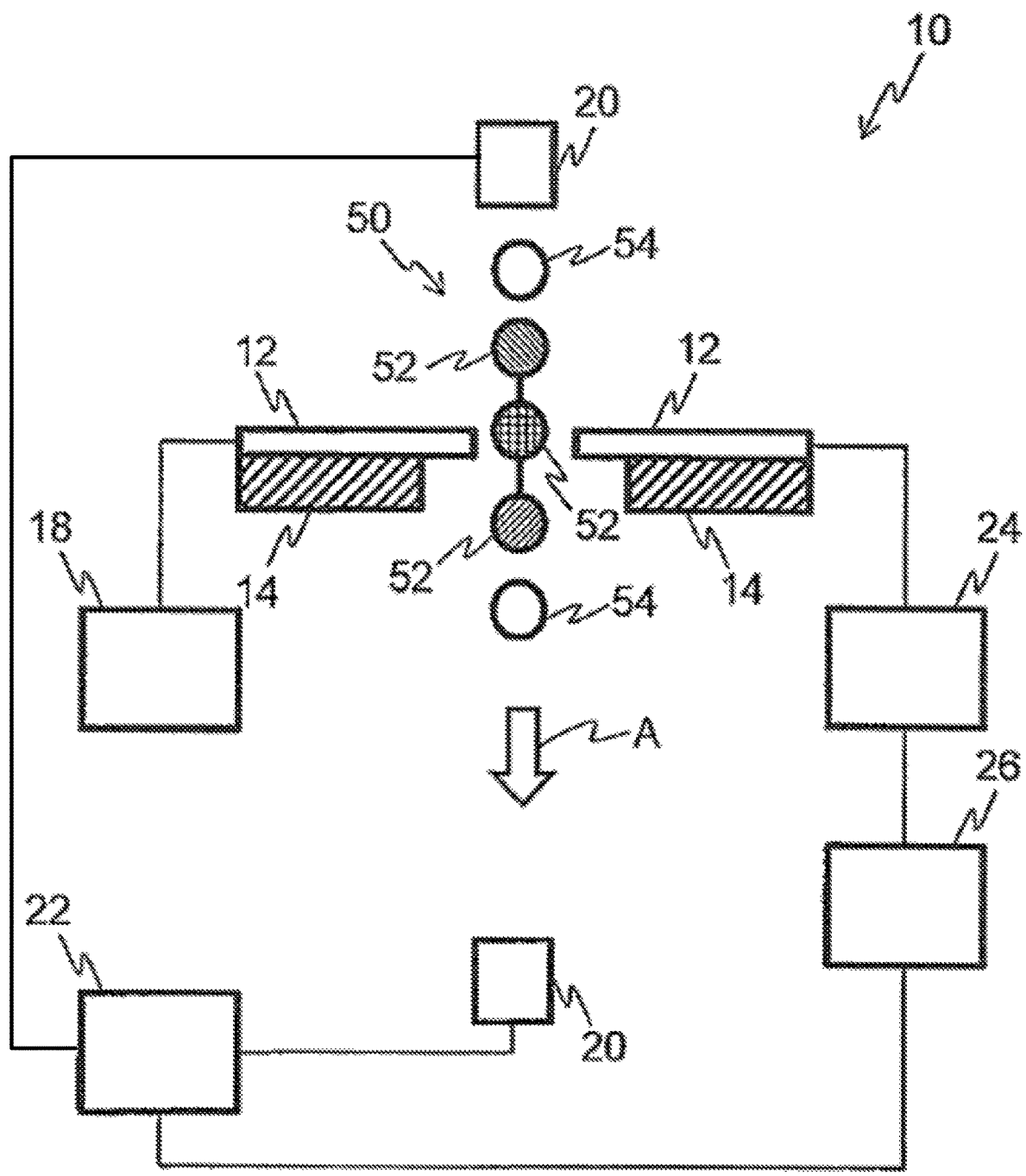
FIG. 1 is a schematic view showing a structure of a biomolecule sequencing apparatus.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "gap," as used herein, generally refers to a pore, channel or passage formed or otherwise provided in a material. The material may be a solid state material, such as a substrate. The gap may be disposed adjacent or in proximity to a sensing circuit or an electrode coupled to a sensing circuit. In some examples, a gap has a characteristic width or diameter on the order of 0.1 nanometers (nm) to about 1000 nm. A gap having a width on the order of nanometers may be referred to as a "nanogap" (also "nanochannel" herein). In some situations, a nanogap has a width that is from about 0.1 nanometers (nm) to 50 nm, 0.5 nm to 30 nm, or 0.5 nm or 10 nm, 0.5 nm to 5 nm, or 0.5 nm to 2 nm, or no greater than 2 nm, 1 nm, 0.9 nm, 0.8 nm, 0.7 nm, 0.6 nm, or 0.5 nm. In some cases, a nanogap has a width that is at least about 0.5 nm, 0.6 nm, 0.7 nm, 0.8 nm, 0.9 nm, 1 nm, 2 nm, 3 nm, 4 nm, or 5 nm. In some cases, the width of a nanogap can be less than a diameter of a biomolecule or a subunit (e.g., monomer) of the biomolecule.

The term "current," as used herein, generally refers to electrical current. Current that is on the order of micro or nano amperes may be referred to as a "nano current" (also "nanocurrent" herein). In some examples, current is or includes tunneling current.

The term "electrode," as used herein, generally refers to a material that can be used to measure electrical current. An electrode can be used to measure electrical current to or from another electrode. In some situations, electrodes can be disposed in a channel (e.g., nanogap) and be used to measure the current across the channel. The current can be a tunneling current. Such a current can be detected upon the flow of a biomolecule (e.g., protein) through the nanogap. In some cases, a sensing circuit coupled to electrodes provides an applied voltage across the electrodes to generate a current. As an alternative or in addition to, the electrodes can be used to measure and/or identify the electric conductance associated with a biomolecule (e.g., an amino acid subunit or monomer of a protein). In such a case, the tunneling current can be related to the electric conductance.

Electrodes situated in a nanogap may be referred to as "nanogap electrodes." Nanogap electrodes can include at least two electrodes, which may be electrically isolated from one another in the absence of an entity that electrically couples the electrodes together, such as, for example, a biomolecule or an electrical conductor (e.g., metal nanoparticle).

The term "protein," as used herein, generally refers to a biological molecule, or macromolecule, having one or more amino acid monomers, subunits or residues. A protein containing 50 or fewer amino acids, for example, may be referred to as a "peptide." The amino acid monomers can be selected from any naturally occurring and/or synthesized amino acid monomer, such as, for example, 20, 21, or 22 naturally occurring amino acids. In some cases, 20 amino acids are encoded in the genetic code of a subject. Some proteins may include amino acids selected from about 500 naturally and non-naturally occurring amino acids. In some situations, a protein can include one or more amino acids selected from isoleucine, leucine, lysine, methionine, phenylalanine, threonine, tryptophan and valine, arginine, histidine, alanine, asparagine, aspartic acid, cysteine, glutamine, glutamic acid, glycine, proline, serin and tyrosine.

The term "nucleic acid," as used herein, generally refers to a molecule comprising one or more nucleic acid subunits or monomers. A nucleic acid may include one or more subunits selected from adenosine (A), cytosine (C), guanine (G), thymine (T) and uracil (U), or variants thereof. A nucleotide can include A, C, G, T or U, or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a nucleic acid is deoxyribonucleic acid (DNA) or ribonucleic acid (RNA), or derivatives thereof. A nucleic acid may be single-stranded or double stranded.

The present disclosure provides devices, systems and methods for the identification of biomolecules, such as, for example, peptides, nucleic acid molecules, and sugars. Nucleic acid molecules can include deoxyribonucleic acid (DNA), ribonucleic acid (RNA), and variants thereof. Nucleic acid molecules may be single or double stranded. Biomolecules of the present disclosure can include monomers or individual subunits. Examples of monomers include amino acids and nucleotides.

In some embodiments, a tunneling current may flow when a monomer may pass through between electrodes and may be measured as a nano current. In some embodiments, constitute amino acids may be identified so as to determine the sequence of one or more peptides, wherein the amino acids may comprise the one or more peptides, which may result from degradation of one or more proteins.

As shown in FIG. 1, a biomolecule sequencing apparatus 10 according to a first embodiment may include a nanogap electrode pair 12, a measurement power source 18, electrophoresis electrode pair 20, an electrophoresis power source 22, an ammeter 24 and a control unit 26. These structures are described herein.

A nanogap electrode pair 12 may comprise two electrodes, each of which may be formed on a dielectric(s) 14. The two electrodes of a nanogap electrode pair may be spaced apart from each other such that a tunneling current may flow when a monomer 52 or a reference substance (or reference sample) 54 (described in detail elsewhere herein), which may be contained in a sample 50, may be passed through between the electrodes of a nanogap electrode pair. The method of manufacturing a nanogap electrode pair 12 is not particularly limited.

A measurement power source 18 may be configured to apply voltage to the electrodes of a nanogap electrode pair 12. Magnitude of a voltage which may be applied to the electrodes of nanogap electrode pair 12 by measurement power source 18 is not particularly limited, and may be between 0.1 V and 2 V, 0.1 V and 1.5 V, 0.1 V and 1.4 V, 0.1 V and 1.3 V, 0.1 V and 1.2 V, 0.1 V and 1.1 V, 0.25 and 1.1 V, 0.25 V and 1 V, 0.25 V and 0.75 V, or 0.6 V and 0.85 V. In some cases, the voltage may be at least about 0.1 V, 0.2 V, 0.3 V, 0.4 V, 0.5 V, 0.6 V, 0.7 V, 0.8 V, 0.9 V, 1 V, 1.1 V, 1.2 V, 1.3 V, 1.4 V, 1.5 V, or 2 V. As an alternative, the voltage may be less than or equal to about 2 V, 1.5 V, 1.4 V, 1.3 V, 1.2 V, 1.1 V, 1 V, 0.9 V, 0.8 V, 0.7 V, 0.6 V, 0.5 V, 0.4 V, 0.3 V, 0.2 V, or 0.1 V. A structure for measurement power source 18 is not particularly limited, and any known power source device may be suitably used.

Electrophoresis electrodes pair 20 may be located so as to form an electric field in a direction in which monomer 52 and the reference substance 54, which may be contained in sample 50, may move (shown by block arrow A in FIG. 1). When an electric field may be formed between a pair of electrophoresis electrodes 20, monomer 52 and/or reference substance 54 may be electrophoretically moved in the direction of the electric field, depending on the charge of monomer 52 and or reference substance 54; alternatively, depending on the charge of monomer 52 and or reference substance 54, monomer 52 and or reference substance may move oppositely to an electrophoretic filed generated by electrophoresis electrode pair. Monomer 52 and or reference substance 54 may be moved so as to pass through between the electrodes of nanogap electrode pair 12.

Electrophoresis power source 22 may be configured to apply voltage to electrophoresis electrode pair 20. The magnitude of voltage which may be applied to electrophoresis electrode pair 20 by electrophoresis power source 22 may not be particularly limited. It may be possible to suitably set a voltage for a speed whereby monomer 52 and or reference substance 54 may be pass through between the electrodes of nanogap electrode pair 12 may be controlled. The structure of electrophoresis power source 22 is not particularly limited, and any known power supply source device may be suitably used.

Ammeter 24 may be configured to measure a tunneling current that may be generated when monomer 52 and or reference substance 54 may pass through between the electrodes of nanogap electrode pair 12 to which voltage may be applied by measurement power source 18. The structure of ammeter 24 is not particularly limited, and any known current measuring device may be suitably used.

Control unit 26 may be configured to control the respective structures of biomolecule sequencing apparatus 10, and may be configured to identify a kind of monomer 52 based on a signal corresponding to a measured tunneling current.

Figure 2:
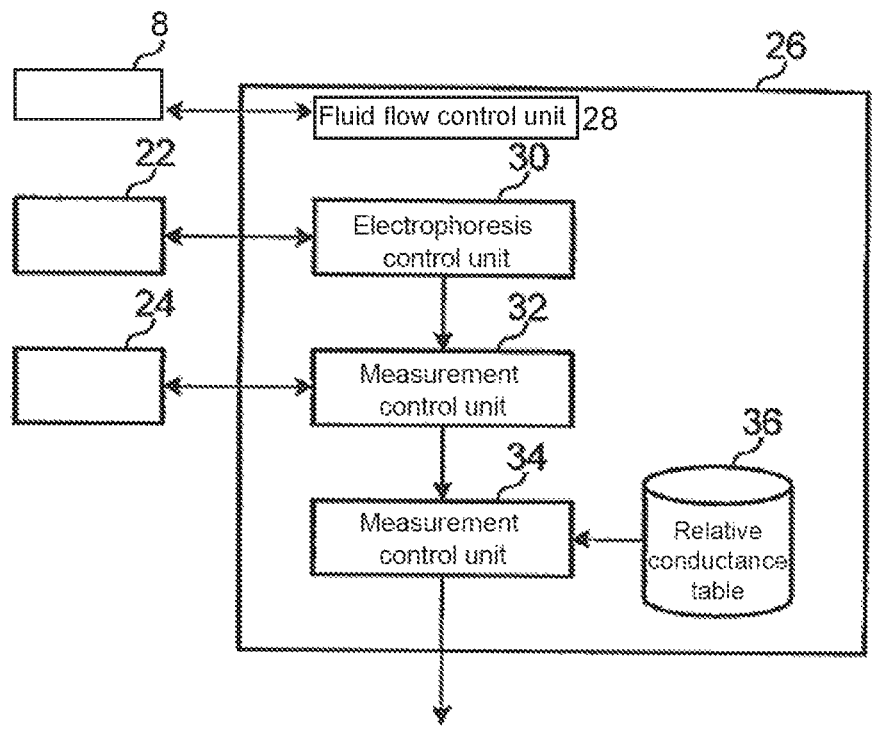
FIG. 2 is a block diagram showing a functional structure of a control unit.

Control unit 26 may comprise a computer including a central processing unit (CPU) and memory, such as random access memory (RAM) or read only memory (ROM), which may store a biomolecule sequencing program as described herein, and so on. As shown in FIG. 2, in terms of function, control unit 26 may include an electrophoresis control unit 30, a measurement control unit 32 and an identification unit 34. The respective units are described in detail below.

Electrophoresis control unit 30 may be configured to control voltage application by electrophoresis power source 22, such that monomer 52 and or reference substance 54 may be passed through between the electrodes of nanogap electrode pair 12.

Measurement control unit 32 may be configured to control ammeter 24 such that ammeter 24 may measure tunneling current that flows between the electrodes of nanogap electrode pair 12. Although a time utilized for measuring tunneling current is not limited, a time utilized may be less than 1 minute, 1 to 2 minutes, 2 to 4 minutes, 4 to 10 minutes, 10 to 20 minutes, 20 to 30 minutes, 30 to 40 minutes, 40 to 50 minutes or 50 minutes to 1 hour, 1 to 2 hours, 2 to 3 hours, 3 to 5 hours, 5 to 10 hours, or more than 10 hours for example. In some cases, the time may be at least about 1 second, 10 seconds, 30 seconds, 1 minute, 2 minutes, 3 minutes, 4 minutes, 5 minutes, 6 minutes, 7 minutes, 8 minutes, 9 minutes, 10 minutes, 30 minutes, 1 hour, 2 hours, 3 hours, 4 hours, 5 hours, 6 hours, or 12 hours. As an alternative, the time may be less than or equal to about 12 hours, 6 hours, 5 hours, 4 hours, 3 hours, 2 hours, 1 hour, 30 minutes, 20 minutes, 10 minutes, 9 minutes, 8 minutes, 7 minutes, 6 minutes, 5 minutes, 4 minutes, 3 minutes, 2 minutes, 1 minute, 30 seconds, 10 seconds, or 1 second. In addition, measurement control unit 32 may be configured to obtain current values of tunneling current measured by ammeter 24, and to determine a conductance from obtained current values so as to create a conductance-time profile. Conductance may be calculated by dividing current values of tunneling current by a voltage V which may have been applied to the electrodes of nanogap electrode pair 12 when tunneling current may have been measured. With the use of a conductance, even when a value of voltage to be applied between the electrodes of nanogap electrode pair 12 differs between measurements, profiles with a unified reference may be obtained. When a value of voltage to be applied between the electrodes of nanogap electrode pair 12 is unchanged between measurements, the current values of the tunneling current and the conductance can be equally handled.

Alternatively, measurement control unit 32 may amplify tunneling current measured by ammeter 24 by using a current amplifier and then obtain a measurement of an amplified current. Using of a current amplifier, a value of a tunneling nano current may be amplified, whereby tunneling current may be measured with high sensitivity. A commercially available variable high-speed current amplifier (manufactured by Femto GmbH, Catalog No. DHPCA-100) may be used as a current amplifier, for example.

Identification unit 34 may be configured to identify using as a reference a signal indicating reference substance 54 which may be included in a plurality of signals seen in a conductance-time profile created by measurement control unit 32, whereby a kind of monomer may be indicated by an additional signal.

Figure 3:
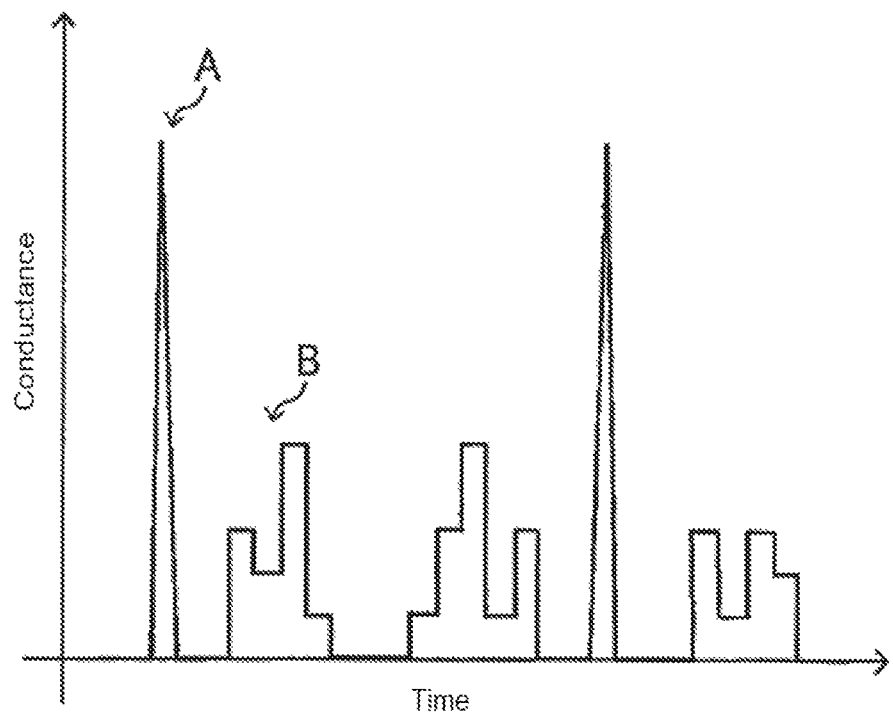
FIG. 3 is a view showing a schematic example of a conductance-time profile.

FIG. 3 shows a schematic example of a conductance-time profile. As shown in FIG. 3, a plurality of signals seen in a conductance-time profile may be time intervals having a peak value. Each peak, and each peak value may correspond to one signal. Thus, in the example shown in FIG. 3, there is one signal in a time interval pointed to by arrow "A", and there are four signals in a time interval pointed to by arrow "B".

In addition, in the example shown in FIG. 3, the signal of the time interval pointed to by arrow "A" may be a signal indicating a reference substance 54, and the respective signals included in a signal group of a time interval pointed to by arrow "B" may be signals indicating several different monomers 52. In some embodiments, when a conductance of signal indicating reference substance 54, and a relative conductance of each kind of the monomer 52 to be identified with respect to a conductance signal indicating reference substance 54 may be known, the kinds of monomers indicated by each signal may be identified.

Figures 4, 5:
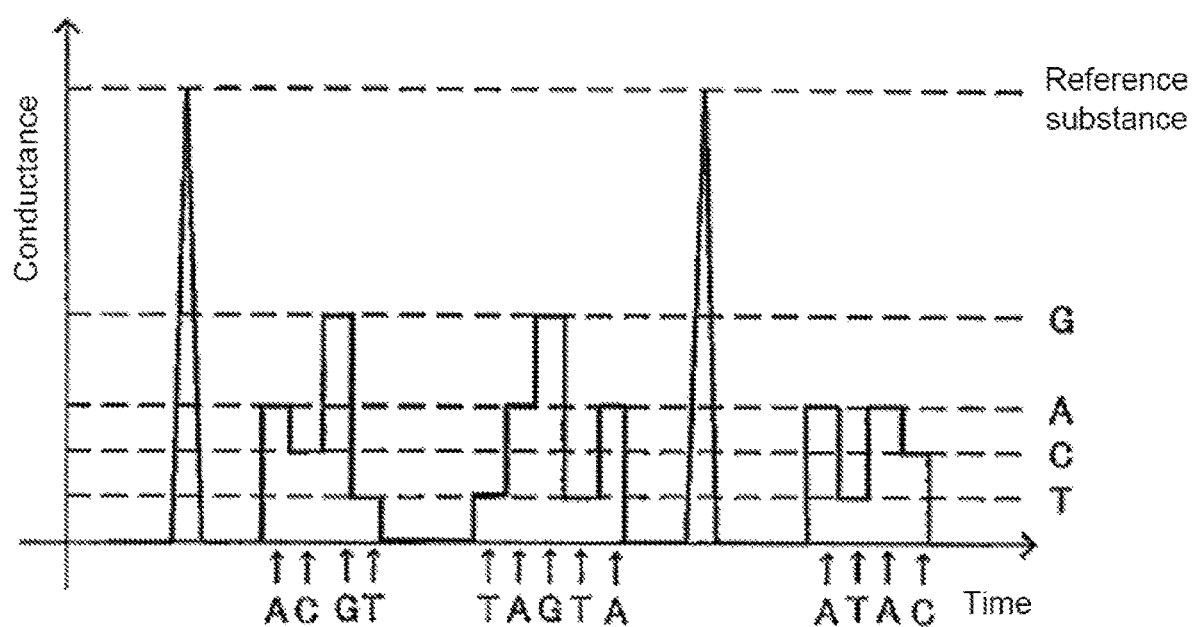
FIG. 4 is a view showing an example of a relative conductance table.
FIG. 5 is a view showing biomolecule sequencing.

To be specific, relative conductances of a monomer 52 to be identified with respect to a conductance specific to reference substance 54 may be stored in a relative conductance table 36 in advance. FIG. 4 shows an example of a relative conductance table 36. As shown in FIG. 5, identification unit 34 may compare conductances of signals other than a signal indicating reference substance 54, which may be seen in conductance-time profile, and the relative conductances of monomer 52 to be identified, which may be stored in relative conductance table 36, and identifies a kind of monomer having a relative conductance which coincides with a signal conductance, allowing identification of the kind of the monomer indicted by a signal. A relative conductance may be considered to coincide with a signal conductance both wherein a relative conductance and a signal conductance completely coincide with each other, but also wherein a difference therebetween is not more than a threshold value.

In order to identify a kind of monomer 52 indicated by a signal using relative conductance values, reference substance 54 preferably has the following properties.

Figure 6:
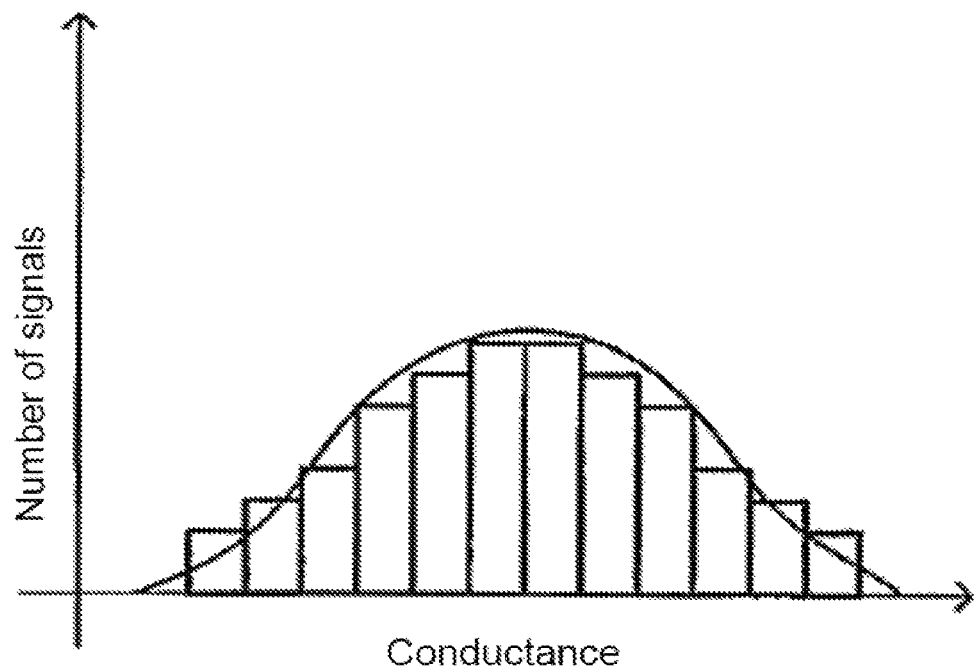
FIG. 6 is a view showing an example of a conductance histogram.
Figure 7:
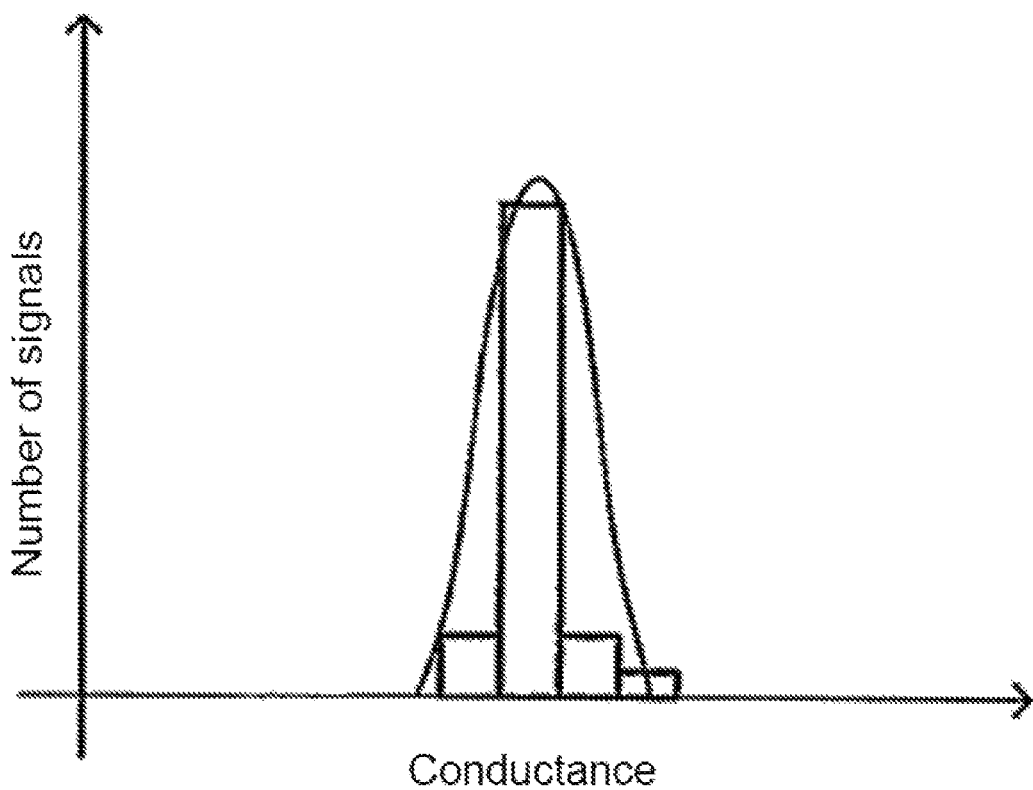
FIG. 7 is a view showing an example of a conductance histogram.

When a nano current such as a tunneling current may be measured using gap electrodes, a distance between an electrode and a molecule passing through between the electrodes of a nanogap electrode pair has an influence on a magnitude of a nano current to be measured. Thus, when a monomer changes its position relative to the electrodes of a nanogap electrode pair each time when it is passed through between the electrodes, measured conductance (e.g., magnitude of signal) may vary for each measurement. For example, as shown in FIG. 6, wherein a histogram of conductances obtained through a plurality of measurements is created, a substance having a large variance in the histogram is not suited for use as reference substance 54. Thus, a substance whose conductance does not so vary significantly for each measurement may be more effectively used as reference substance 54. As shown in FIG. 7, for example, a substance having a small variance in a histogram of conductances obtained through a plurality of measurements is suited to be used as reference substance 54.

In order to reduce variations in conductance between measurements, it may be desirable to utilize for reference substance 54, a composition wherein variation in the orientation of a reference substance has relatively little effect on measurements with respect to a space between the electrodes of a nanogap electrode pair for through which a reference substance 54 may be passed through between the electrodes. For example, compounds may be used wherein the orientation may be uniquely determined when the compound passes through between electrodes of a nanogap electrode pair because of a relationship between a space between the electrodes of a nanogap electrode pair and shapes of a compound wherein variant orientations of the compound between the electrodes of a nanogap electrode pair may be precluded; alternatively compounds may be utilized for reference substance 54 whose orientations may be electrophoretically controlled so as to be unchanged when they are passed through between the electrodes of a nanogap electrode pair. Moreover, when the shapes of a compound which may be utilized as a reference substance 54 which may be spherical or sufficiently spherical in shape that the orientation of a compound used as a reference substance 54 may not have a significant influence on measured conductances associated with the compound utilized as a reference substance 54, the orientation with respect to the electrodes of a nanogap electrode pair of the compounds utilized as a reference substance 54 may be effectively unchanged when they are passed through between the electrodes, without any need for considering a relationship between the compound utilized as a reference substance 54 and the electrodes.

In addition, since a signal indicating reference substance 54 may be used as a reference, it is preferable that the signal can be obviously differentiated from a signal indicating a monomer 52 to be identified. Thus, it is preferable that reference substance 54 have an electric conductivity, and may have a conductivity which may not be confused with a monomer to be identified. Further, in order to make stable a signal associated with reference substance 54 as a reference, reference substance which may be contained in sample 50 may preferably be composed of compounds with the same shape. In addition, as shown in FIG. 3, since it is preferable that a signal indicating reference substance differs significantly from a signal indicating monomer 52, reference substance preferably has a large conductance as compared with that of a monomer 52 to be identified.

In consideration of the above conditions, metal nanoparticles or fullerenes may be used as reference substances 54. Metal nanoparticles may, for example, be gold nanoparticles, silver nanoparticles, copper nanoparticles, aluminum nanoparticles and the like. When the size of a monomer 52 to be identified may be about 0.5 nm to 2 nm, fullerenes may suitably be used as reference substances 54. On the other hand, when the size of a monomer 52 to be identified is 2 nm or more, metal nanoparticles such as gold nanoparticles may suitably be used as reference substances 54.

Next, a monomer identifying method carried out by using the biomolecule sequencing apparatus 10 according to the first embodiment is described.

At least one or more kinds of monomer 52 may be dissolved in a solution. The solution is not particularly limited. For example, ultrapure water may be used. Ultrapure water may be manufactured, for example, using a Milli-Q Integral 3, Milli-Q Integral Catalog No. 3/5/10/15 manufactured by Millipore Co. A concentration of monomer 52 in solution is not particularly limited, and may be from about 0.01 µM to 1.0 µM, or 0.01 µM to 0.5 µM. In some cases, the concentration of monomer 52 in solution is less than about 5 µM, 4 µM, 3 µM, 2 µM, 1.5 µM, 1 µM, 0.5 µM, 0.1 µM, or 0.01 µM. As an alternative, the concentration of monomer 52 in solution is more than about 0.01 µM, 0.1 µM, 0.5 µM, 1 µM, 1.5 µM, 2 µM, 3 µM, 4 µM, or 5 µM.

Figure 8:
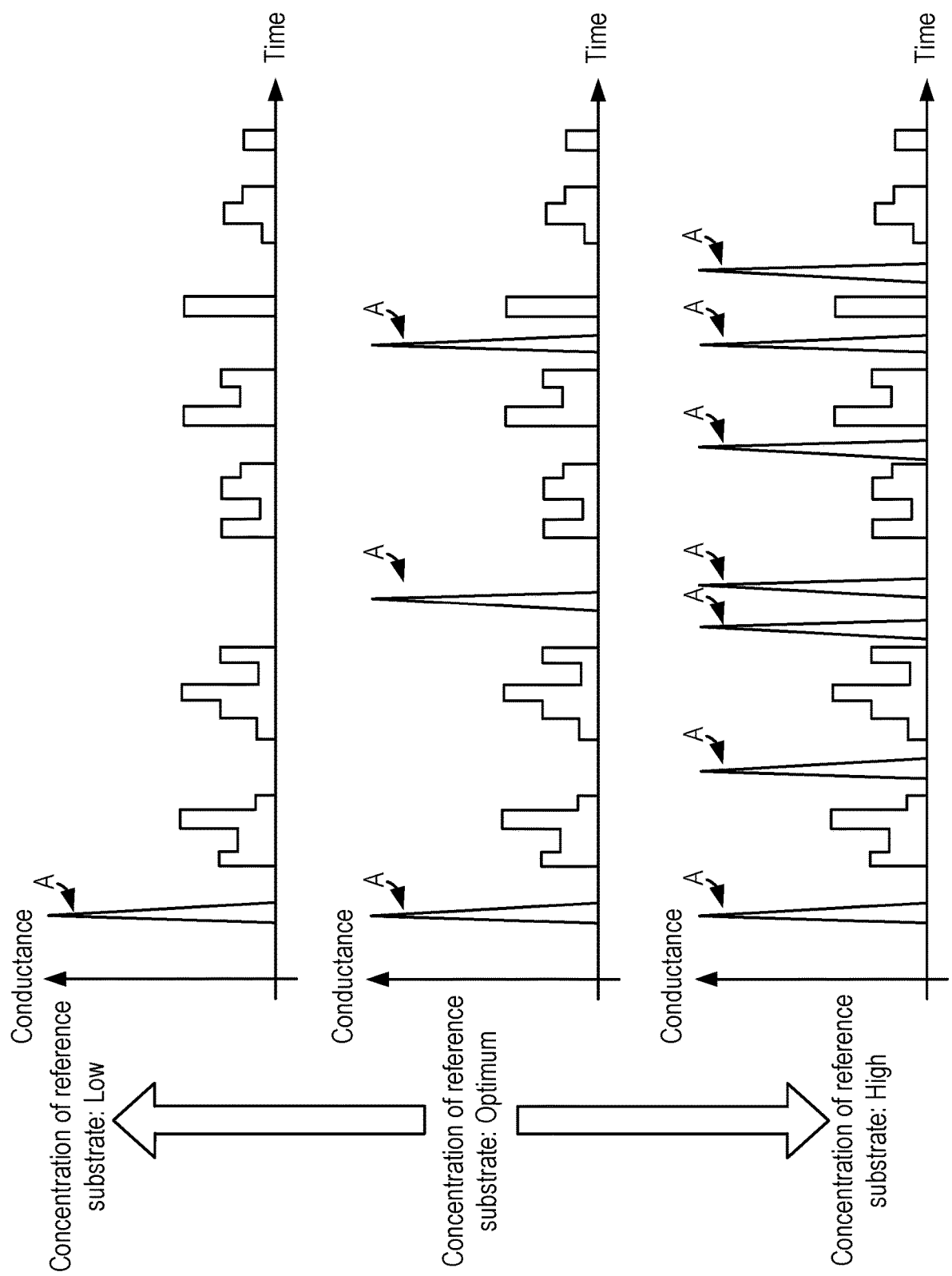
FIG. 8 is a view showing optimization of concentration of a reference substance (or reference sample)

Then, aforementioned reference substances 54 may be added to a solution in which monomer 52 may be dissolved. A concentration of reference substances 54 in the solution may be optimized such that a rate of the signal indicating reference substance 54 with respect to a plurality of signals seen in a conductance-time profile falls within a predetermined rate range. As shown in FIG. 8, when a concentration of reference substances 54 is low, as the number of signals (indicated by "A" in FIG. 8) indicating reference substance 54 in the conductance-time profile is small, the signal indicating reference substance 54 cannot be frequently detected, potentially preventing effective compensation for monomer 52 signal variations. Meanwhile, when the concentration of reference substances 54 is potentially too high, as the number of signals indicating reference substance 54 in the conductance-time profile is large, the reference substance 54 signals may give rise to noise, and may interfere with passage of monomers 52. Thus, a predetermined range may be defined so as to provide an optimum number of signals in consideration of balance between stability in identification and reduction in noise. The number of reference substance signals needed within a period of time may be a function of the stability of a biomolecule sequencing apparatus, wherein if a biomolecule sequencing apparatus is highly stable, with little in the way of temperature dependence and stable nanogap electrode pair electrode tips, considerable periods of time may be permissible without needing a signal from a reference substance. If a biomolecule sequencing apparatus is, for example, temperature dependent, it may be desirable to have more frequent signals from a reference substance. It may, for example, be desirable to have a signal from a reference substance whenever a conductance may change as a result of systematic changes such as, for example temperature, by greater than 2%, greater than 5%, greater than 10%, greater than 20%, or greater than 30% relative to conductances as measured under previous systematic conditions. It may be necessary to utilize multiple signals from reference substances to determine systematic changes; reference signals will not be uniformly distributed, but will likely follow a Poisson distribution; so a frequency of signals from reference substances may need to occur more frequently, such that a predetermined statistical confidence may be achieved with respect to the likelihood of a biomolecular sequencing system systematically changing by more than a desired amount, and a number of reference substance signals needed to determined and or compensate for such a change, and a distribution of reference substance signals.

Then, the electrodes of a nanogap electrode pair 12 may have sample 50 caused to be positioned thereupon, and a voltage may be applied by measurement power source 18 to the electrodes of nanogap electrode pair 12, and voltage may be applied by electrophoresis power source 22 to electrophoresis electrode pair 20. Thereafter, a CPU of a computer which may comprise control unit 26 may retrieve biomolecule sequencing program which may be stored in ROM so as to execute it, so that a biomolecule sequencing process as shown in FIG. 9 may be carried out by biomolecule sequencing apparatus 10.

Figure 9:
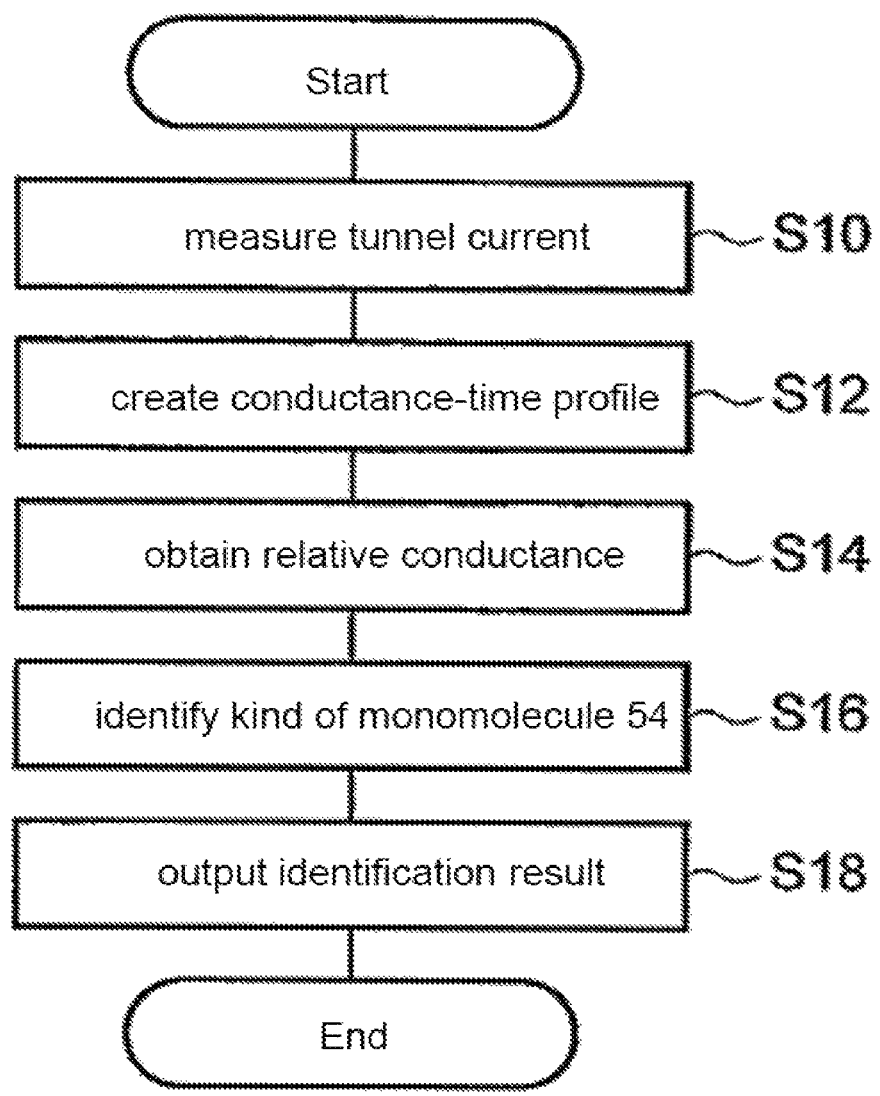
FIG. 9 is a flowchart showing a biomolecule sequencing process.

In step S10 of a biomolecule sequencing process as shown in FIG. 9, measurement control unit 32 may control the ammeter 24, such that a tunneling current, which may be generated when monomer 52 and reference substance 54 may be passed through between the electrodes of nanogap electrode pair 12, and may be measured for a predetermined period of time.

Then, in a step S12, measurement control unit 32 may obtain current values of measured tunneling current, and may calculate a conductance for measurement points so as to create a conductance-time profile as shown in FIG. 3, for example. Then, in a step S14, identification unit 34 may obtain relative conductances of monomer 52 to be identified from relative conductance table 36.

Then, in step S16, identification unit 34 may compare the conductance-time profile created in step S12 and relative conductances obtained in step S14, to identify the kind of monomer indicated by each signal. Then, in step S18, identification unit 34 outputs an identification result, and a biomolecule sequencing process may be finished.

As described herein, an identification apparatus may utilize as a reference substance, a substance having a small variation in conductance in a conductance-time profile created based on tunneling currents that flow between the electrodes of a nanogap electrode pair. By using as a reference a conductance of a signal indicating a reference substance in a conductance-time profile, a kind of the monomer indicated by an additional signal may be identified. Thus, a reference substance may be utilized as a standard such that, for a sample containing an unknown molecule, biomolecule sequencing utilizing nano current measurement using nanogap electrode pair(s) may be carried out without needing an additional step such as a separation step, a refinement step or the like.

In describing FIG. 10 hereinafter, those reference numbers which are similarly used in FIG. 1 refer to parts identical to those of FIG. 1 and detailed description thereof is omitted.

A biomolecule sequencing apparatus can include a plurality of sets of nanogap electrodes, each set comprising at least two electrodes. In FIG. 10, biomolecule sequencing apparatus 210 may include multiple nanogap electrode pairs 12A, 12B and 12C, a measurement power source 18, a pair of electrophoresis electrodes 20, an electrophoresis power source 22, an ammeter 24 and a control unit 226. Each of the nanogap electrode pairs 12A, 12B and 12C is a set of nanogap electrodes. The control unit 226 may be similar or identical to control unit 26 describe elsewhere herein.

A structure for nanogap electrode pairs 12A, 12B and 12C may be the same as that for nanogap electrode pair 12 described in association with FIG. 1. Nanogap electrode pairs 12A, 12B and 12C may be formed on dielectric(s) 14 such that centers between the electrodes may be aligned on the same axis. A path through which a monomer 52 and reference substance 54 may pass may be defined between each of the electrodes of nanogap electrode pairs 12A, 12B and 12C. A distance between the electrodes of nanogap electrode pairs 12A may be depicted as d1, a gap between the electrodes of nanogap electrode pair 12B may be depicted as d2, and a gap between the pair electrodes of nanogap electrode pair 12C may be depicted as d3. Distances d1, d2 and d3 may differ from one another. In the example shown in FIG. 10, d1>d2>d3. For example, distance d1 may be 1.0 nm, distance d2 may be 0.7 nm and distance d3 may be 0.5 nm.

Figure 11:
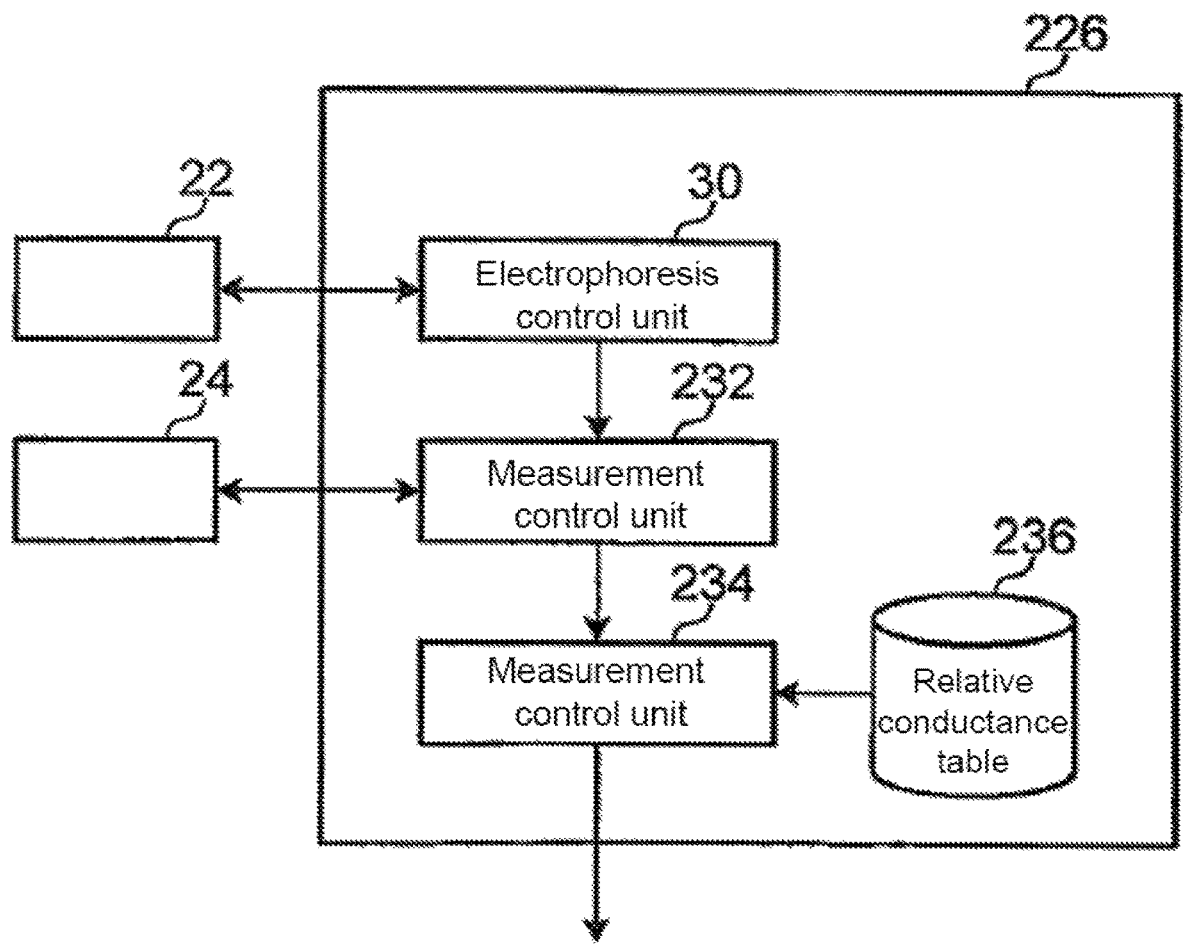
FIG. 11 is a block diagram showing a functional structure for a control unit.

As shown in FIG. 11, control unit 226 may include an electrophoresis control unit 30, a measurement control unit 232 and an identification unit 234.

The measurement control unit 232 may be configured to control ammeter 24 such that tunneling currents generated between the electrodes of nanogap electrode pairs 12A, 12B and 12C may be separately measured. In addition, measurement control unit 232 may be configured to obtain current values of tunneling currents for each distance between the electrodes of nanogap electrode pairs measured by ammeter 24 and to calculate conductances so as to create a conductance-time profile for each distance between the electrodes of nanogap electrode pairs.

Identification unit 234 may be configured to identify signal(s) indicating reference substance 54 corresponding to a distance(s) between the electrodes of nanogap electrode pairs included in a plurality of signals seen in a conductance-time profile for each distance between electrodes, and to normalize additional signals based on identified reference substance 54 signal(s). Then, based on a comparison performed for each distance associated with different distances between the electrodes of nanogap electrode pairs, identification unit 234 may be configured to identify a kind of the monomer indicated by a normalized additional signal.

Figure 12:
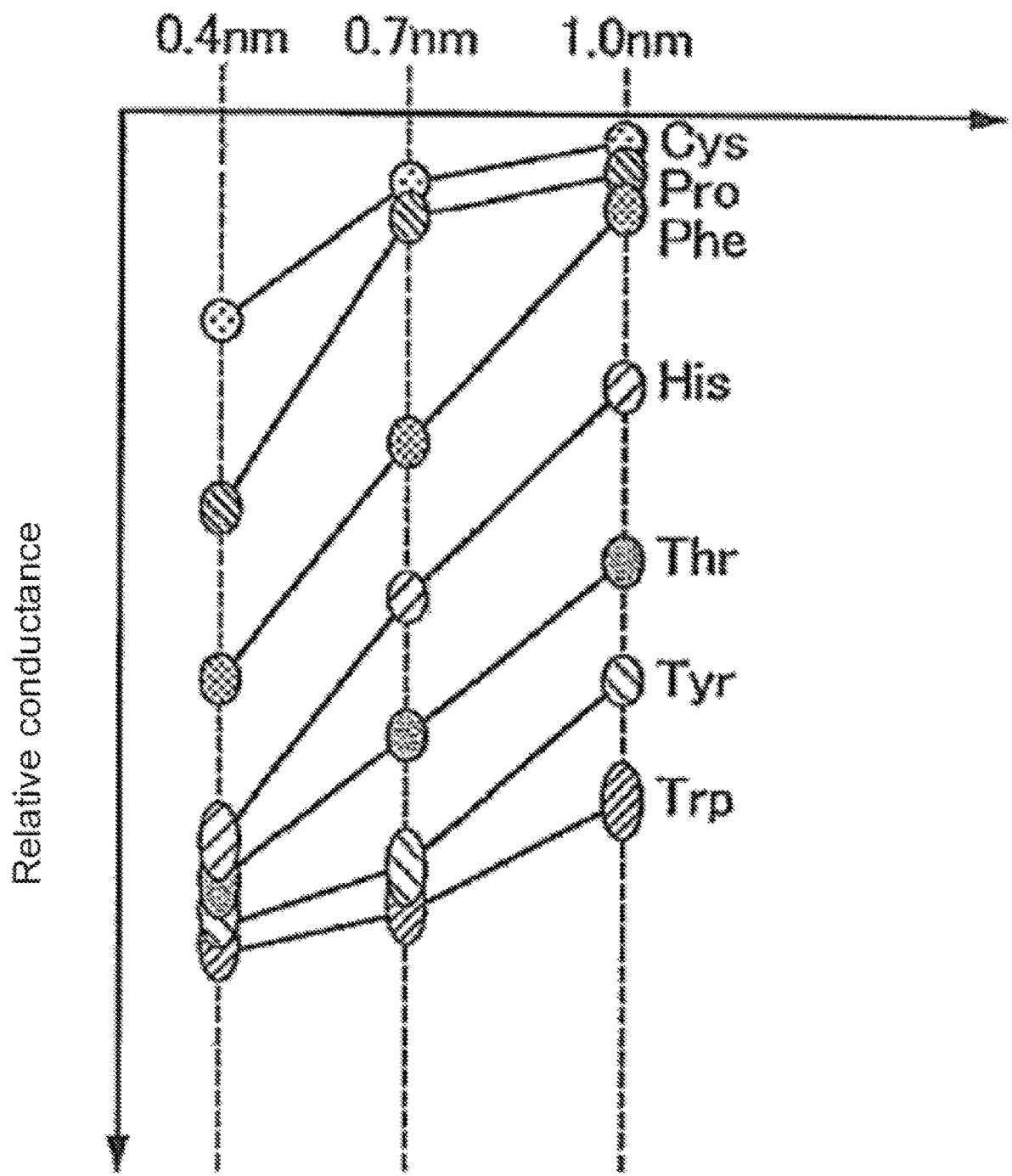
FIG. 12 is a view showing conductances of amino acid for different distances between electrodes.

FIG. 12 shows relative conductances for different distances d between electrodes or nanogap electrode pairs, for multiple kinds of monomers (amino acids in the example shown in FIG. 12). Relative conductance herein may mean a conductance for each monomer (amino acid) when a largest conductance associated with a monomer (amino acid) among monomer kinds (amino acid kinds in FIG. 12 may be normalized to 1. In the example shown in FIG. 12, the distance between electrodes d1 is 1.0 nm, the distance between electrodes d2 is 0.7 nm, and the distance between electrodes d3 is 0.4 nm. As shown in FIG. 12, when the distance between electrodes d is 0.4 nm, relative conductances of His, Thr Tyr and Trp are approximately equal to each other. When a distance between electrodes d is 0.7 nm, relative conductances of Cys and Pro are shown to be approximately equal to each other and relative conductances of Tyr and Trp are shown to be approximately equal to each other. When a distance between electrodes d is 1.0 nm, relative conductances of Cys, Pro and Phe are shown to be approximately equal to each other. When the relative conductances are approximately equal to each other, identification precision of a kind of monomer (amino acid) identified may be low.

A histogram associated with a monomer may be different from histograms associated with other monomers, or may be similar or the same as histogram(s) utilized for one or more other monomers. Further, histograms associated with monomers may also be different for different inter-electrode distances d. A function derived from histograms may generate a curve, which may be a continuous curve or a discontinuous curve, wherein the curve may be used to determine a kind of monomer utilizing deconvolution. In some embodiments a deconvolution matrix may be generated from a standard for a monomer type and inter-electrode distance d. In some embodiments deconvolution may be used to determine a likely monomer king. Math for deconvolution is well known to algorithm developers. In some embodiments matrix math or linear algebra may be used for deconvolution.

For a given monomer determination there may be many different measurements. Some of these measurements may be made with different inter-electrode distances d. In some embodiments, because some of the inter-electrode distances are more suited to determining a monomer kind for a monomer of interest, the quality of the data may be better for some inter-electrode distances than for other inter-electrode distances. In other embodiments it may be desirable to use all the available data when determining a monomer. In some embodiments a quality metric may be used to weight each measurement when making a consensus monomer determination. This may be more useful for samples wherein a number of possible monomers may be large such as for protein sequencing, but may also be used for samples with fewer monomers such as for DNA sequencing.

Electrophoretic speed (velocity and direction) of a protein or sugar may depend upon monomer composition. Charge of a protein may be positive, negative or neutral. Charge level and sign may depend on pH and or ionic concentration. In some embodiments electrophoretic speed may be determined from a current vs. time profile for a polymer sequence as charge to mass ratio may be different for many monomers. In some embodiments electrophoretic speed may be used to generate a monomer composition value and may be utilized to check or weight a sequence consensus determination, or may be utilized in monomer determination wherein pulse durations associated with monomer kinds which may originate from a table or calculation may be modified based on polymer speed through a nanogap electrode pair(s).

In some embodiments a quality metric may be generated from a residual remaining after deconvolution. In some embodiments a quality metric may be generated from physical measurements such as tunneling current level, noise level, event duration time or a mode of tunneling current.

As charge may vary at different monomer positions within a polymer at for some biopolymers, associated electrophoretic speed may vary concordantly. For neutral molecules no motion may be expected unless as a result of electroosmotic flow. Flow velocity may depend upon a temperature of a solution, and may thus vary in different regions of a system which may have different solution temperatures. In some embodiments a biopolymer may be moved past the electrodes of a nanogap electrode pair(s) using one of electrophoresis, electroosmosis, pressure driven flow or combinations of the above. In some embodiments, temperature, pH or ionic concentration of a sample may be varied to change flow characteristics.

Thus, which monomer(s) may be able to be determined may be set in advance for each distance between electrodes of nanogap electrode pairs. Simultaneously, for each distance between electrodes of nanogap electrode pairs, a reference substance 54 which may be readily identified corresponding to different distances between electrodes may be selected in advance, which may result in the use of multiple reference substances, wherein different reference substances may be utilized as a standard for different inter-electrode distances associated with the electrodes of different nanogap electrode pairs. In addition, a relative conductance of a monomer 52 to be identified, which may be identifiable utilizing one or more distances between electrodes, with respect to a particular conductance of reference substance 54 corresponding to the distance between electrodes, may be stored in a relative conductance table 236 in advance. FIG. 13 shows an example of a relative conductance table 236.

Figure 14:
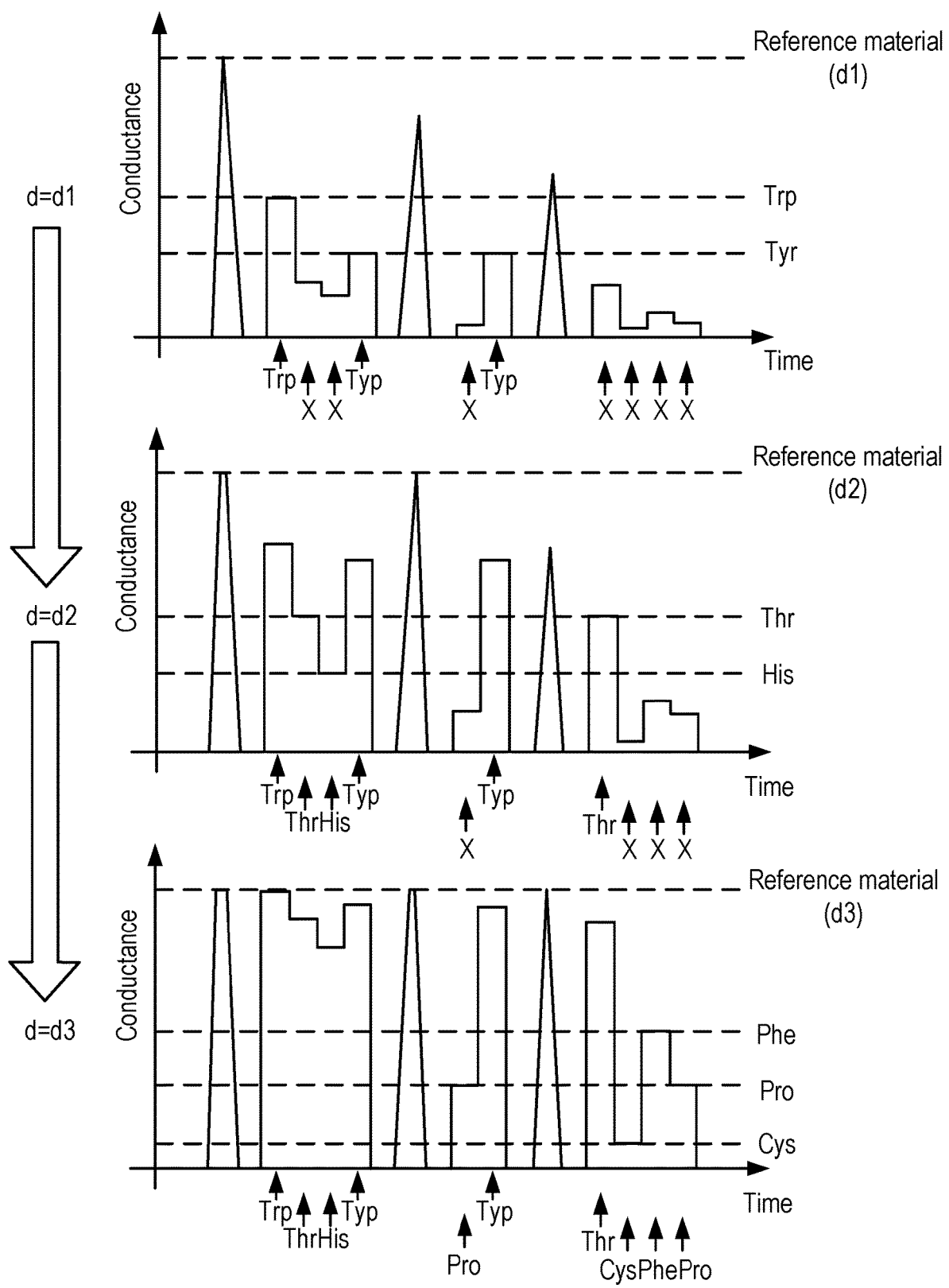
FIG. 14 is a view for explaining a biomolecule sequencing method.

FIG. 14 schematically shows an identification process which may effectuated by identification unit 234. As shown in FIG. 14, identification unit 234 may compares conductances of signals other than a signal indicating reference substance 54 corresponding to the distance between electrodes of a nanogap electrode pair, which may be seen in conductance-time profile(s) for each distance between electrodes of nanogap electrode pairs, and relative conductances of monomer 52 to be identified that may be identifiable for distance(s) between electrodes of nanogap electrode pair(s), which may be stored in relative conductance table 236, so as to identify a kind of monomer indicated by each signal. Signal(s) (signal depicted by "X" in FIG. 14) which cannot be identified based on conductance-time profile for a distance between electrodes of nanogap electrode pair(s), identification unit 234 may identify a kind of monomer based on another conductance-time profile for another distance(s) between electrodes of a nanogap electrode pair(s).

Figure 10:
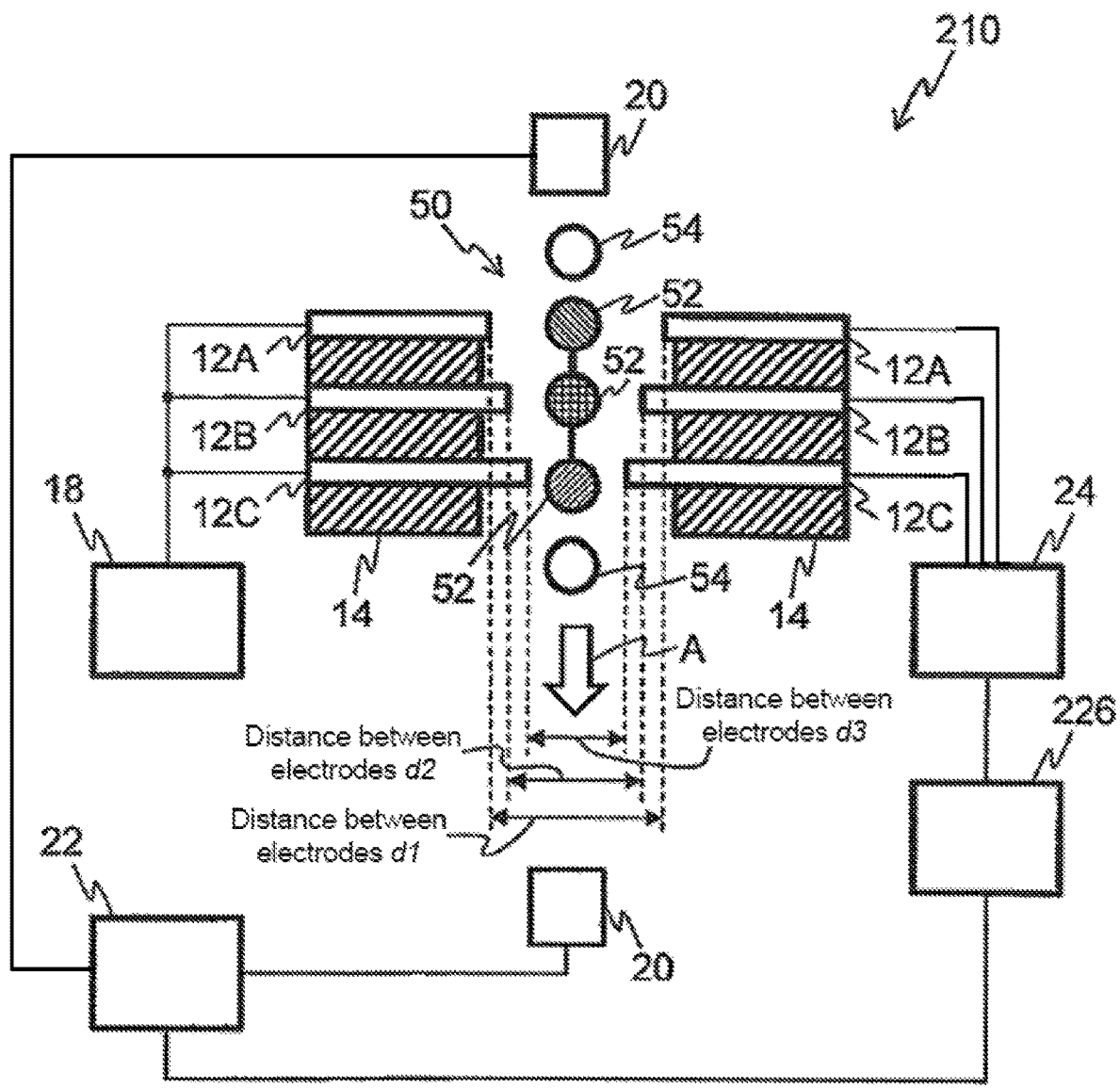
FIG. 10 is a schematic view showing a structure of a biomolecule sequencing apparatus.

In some embodiments, a biomolecule sequencing method carried out using biomolecule sequencing apparatus 210, an embodiment may, in a manner similar to that described in association with FIG. 10, at least one or more kinds of monomer 52 may be dissolved in a solution. Then, previously described reference substance(s) 54 may be added to a solution in which monomer(s) 52 may be dissolved. In some embodiments, reference substance(s) 54 may be added which may provide signals useful as a reference substance corresponding to distances between electrodes (d1, d2 and d3) of nanogap electrode pairs 12A, 12B and 12C.

Then, nanogap electrode pairs 12A, 12B and 12C may have sample 50 introduced thereto. Voltage may be applied by measurement power source 18 to respective nanogap electrode pairs 12A, 12B and 12C, and voltage may be applied by electrophoresis power source 22 to electrophoresis electrode pair 20. Thereafter, a CPU of a computer comprising control unit 226 may retrieve biomolecule sequencing program which may be stored in ROM, RAM, FLASH or other storage media so as to execute it, so that biomolecule sequencing process shown in FIG. 15 may be carried out by biomolecule sequencing apparatus 210.

Figure 15:
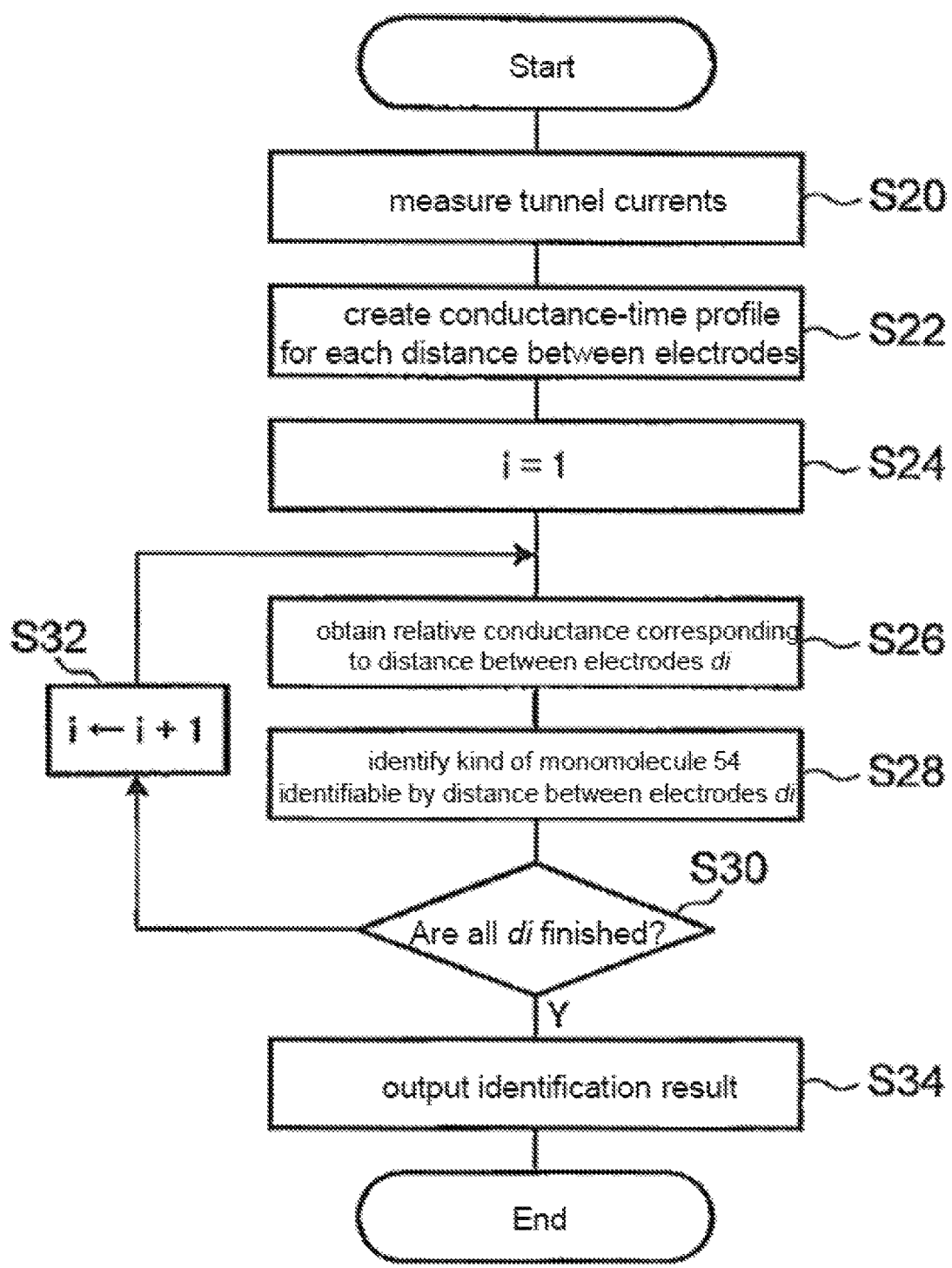
FIG. 15 is a flowchart showing a monomer identification process.

In step S20 of biomolecule sequencing process as shown in FIG. 15, measurement control unit 232 may control ammeter 24, such that tunneling (or tunnel) currents, which may be generated when monomer(s) 52 and reference substance(s) 54 may be passed through a path formed by the electrodes of nanogap electrode pairs 12A, 12B and 12C, wherein measurement may occur for a predetermined period of time.

Then, in step S22, measurement control unit 232 may obtain current values of measured tunneling currents, and may calculate a conductance for each measurement point so as to create, for each distance between electrodes of nanogap electrode pair(s), a conductance-time profile as shown in FIG. 3, for example. Then, in step S24, identifying unit 234 may set variable i to a value of 1.

Then, in step S26, identification unit 234 may obtain, from relative conductance table 236, a relative conductance for monomer(s) 52 corresponding to a distance between electrodes di, i.e., a relative conductance of monomer(s) 52 to be identified which may be identifiable for a distance di between electrodes of nanogap electrode pair.

Then, in step S28, identification unit 234 may compare conductance-time profile for a distance di between electrodes of nanogap electrode pair(s), which may be created in step S22, and a relative conductance which may be obtained in step S26 so as to identify a kind of monomer indicated by each signal.

Then, in step S30, it may be determined whether identification unit 234 has finished a process for all distances di between electrodes of nanogap electrode pair(s) or not. When there is an unprocessed distance di between electrodes of nanogap electrode pair(s), the program may proceed to step S32 in which i is incremented by one, and the program returns to step S26. When a process may be finished for all distances di between electrodes of nanogap electrode pair(s), the program may proceed to step S34 where identification unit 234 may output an identification result, and a monomer identifying process may be finished.

As described herein, a biomolecule sequencing apparatus and method may utilize conductances obtained from tunneling currents generated between the electrodes of nanogap electrode pairs with different distances between electrodes of nanogap electrode pairs may be used, allowing a more precise and or speedy identification may be carried out in comparison a biomolecule sequencing system and method which may utilize a single nanogap electrode pair.

In some embodiments, nanogap electrode pairs may be vertically stacked to provide alignment between the electrodes of several nanogap electrode pairs such that respective pairs of nanogap electrode pairs 12A, 12B and 12C may be stacked on one another such that centers between the electrodes may be aligned on a single axis; in other embodiments, nanogap electrode pairs may be horizontally aligned on a planar surface so as to allow alignment between electrodes of several nanogap electrode pairs such that respective nanogap electrodes 12A, 12B and 12C may be arranged on the same plane. In further embodiments, nanogap electrode pairs may be arranged with multiple common axes, permitting parallel measurements to be conducted. In some embodiments, by providing respective nanogap electrode pairs 12A, 12B and 12C with electrophoresis electrodes, for example, monomer(s) 52 and reference substance(s) 54 may be controlled so as to pass sequentially through between the respective electrodes of nanogap electrode pairs 12A, 12B and 12C.

In some embodiments, in addition to embodiments described herein whereby multiple inter-electrode distances of electrodes of nanogap electrode pairs may have different distances between electrodes, in other embodiments there may be provided a mechanism for changing a distance between electrodes of nanogap electrode pair(s). For example, a principle of leverage may be utilized. In some embodiments, by adjusting a geometric arrangement of a power point, a support point and an action point, a distance between electrodes of a nanogap electrode pair may be changed. More specifically, by pushing upward upon a part of nanogap electrode pair(s) utilizing a piezoelectric element, an end of an electrode of a nanogap electrode pair(s) serving as an action point may be moved so that a distance between electrodes of nanogap electrode pair(s) may be changed. In some embodiments, based on a corresponding relationship between a piezoelectric element movement distance and a distance between electrodes of a nanogap electrode pair(s), a desired distance between electrodes of a nanogap electrode pair(s) may be set.

In some embodiments, tunneling current may be measured and identification of monomers may be effectuated using any biomolecule sequencing method described herein, which may use nano current measurement using nanogap electrodes. In some embodiments, a processing step such as a separation process or a purification process may not be required prior to measurement, and a highly precise biomolecule sequencing may be performed which may be highly selective for wide experimental conditions.

Figure 16:
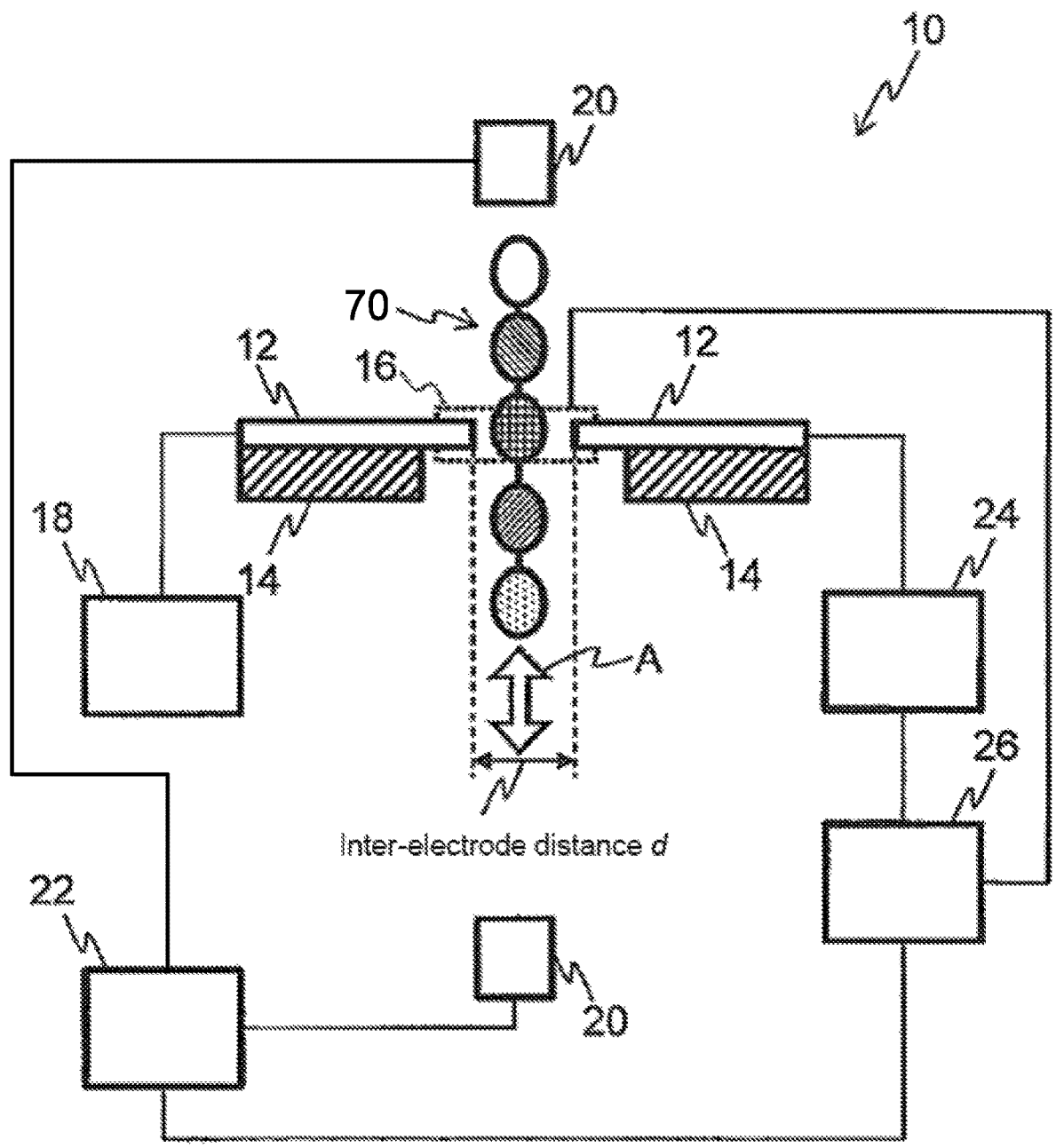
FIG. 16 is a schematic view showing a configuration of a biomolecule sequencing apparatus

For example, when a biomolecule sequencing system and or method as described herein may be used for measuring a typical biopolymer nucleic acid base chains, gene sequence and a gene expression analysis can be made more precise and with improved selectivity. Moreover, a biomolecule sequencing system and or method as described herein may be applied to a rapid, highly sensitive allergen inspection and disease diagnosis with lower cost which may be utilized in the fields of public health, safety and environment. In some embodiments as shown in FIG. 16, a biomolecule sequencing apparatus 10 may include a nanogap electrode pair 12, an inter-electrode distance changing unit 16, a measurement power source 18, an electrophoresis electrode pair 20, an electrophoresis power source 22, an ammeter 24, and a control unit 26. Hereinafter, the respective structures will be explained.

A nanogap electrode pair 12 has two electrodes provided on a dielectric(s) 14 and disposed to face with each other at an inter-electrode distance d at which a tunneling current may flow when a peptide 50 passes through between the nanogap electrode pair 12. If an inter-electrode distance d is substantially longer than molecular diameters of amino acids (they are shown by ellipses in FIG. 16) comprising peptide 50, very little tunneling current may flow between the electrodes of nanogap electrode pair 12, and two or more amino acids may enter between the electrodes of the nanogap electrode pair 12 at the same time. On the contrary, if the inter-electrode distance d is too short as compared with the molecular diameters of amino acids, peptide 50 may not enter between the electrodes of nanogap electrode pair 12.

If the inter-electrode distance d is too long or too short as compared with the molecular diameters of the amino acids comprising peptide 50, it may difficult to detect tunneling current for each amino acid of the amino acids comprising peptide 50. Therefore, inter-electrode distance d may be longer than, shorter than, or equal to the molecular diameters of amino acids comprising peptide 50. For example, an inter-electrode distance may be 0.5 to 2 times the molecular diameters of amino acids comprising a peptide, 1 to 1.5 times the molecular diameters of amino acids comprising a peptide, or 0.8 to 1.0 times the molecular diameters of amino acids comprising a peptide, or 1 to 1.2 times the molecular diameters of amino acids comprising a peptide, or a respective ratio between a molecular diameter of a monomer and an inter-electrode distance.

Herein, molecular diameters of amino acids may differ depending on the kinds of the amino acids. A tunneling current may be affected by the distance between electrodes and a molecule to be measured. Thus, in the case wherein an inter-electrode distance is fixed, a tunneling current derived from each of multiple kinds of amino acids may not allow determination of individual amino acids to be measured with high accuracy. In some embodiments, an inter-electrode distance d may be changed by inter-electrode distance changing unit 16 such that nanogap electrode pair 12 may be adjusted so as to have several different inter-electrode distances at different times.

Inter-electrode distance changing unit 16 may be controlled by control unit 26, which will be discussed later, to change an inter-electrode distance d of nanogap electrode pair 12. For example, inter-electrode distance changing unit 16 may have a configuration whereby an inter-electrode distance d may be changed by adjusting using the lever principle. For example, a nanofabricated mechanically-controllable break junction (MCBJ) may be used to control the inter-electrode distance with suitable mechanical stability, and with sub-picometer resolution. A method to fabricate an electrode pair by using a nanofabricated mechanically-controllable break junctions method may be found in, for example, J. M. van Ruitenbeek, A. Alvarez, I. Pineyro, C. Grahmann, P. Joyez, M. H. Devoret, D. Esteve, and C. Urbina, Rev. Sci. Instrum., 67, 108 (1996), which is entirely incorporated herein by reference. In some cases, a part of nanogap electrode pair 12 may be pushed up by a piezoelectric element to move the electrode edge part, so as to achieve a configuration whereby inter-electrode distance d may be changed. In this case, based on the relationship between the pushing-up distance of the piezoelectric element and the inter-electrode distance, an intended inter-electrode distance may be set. For example, using the MCBJ setup in a configuration wherein inter-electrode distance d may be moved apart by 0.1 nm by pushing up the piezoelectric element by 1 μm, in order to widen the inter-electrode distance by 0.1 nm, control unit 26 may control inter-electrode distance changing unit 16 such that a piezoelectric element may be pushed up by 1 μm. This MCBJ setup example has a mechanical conversion ratio of 1/10000. As discussed above, in a configuration using a piezoelectric element, a distance can be controlled, for example, to within about 0.1 picometers (pm), 0.5 pm, 1 pm, 10 pm, 100 pm, or 1000 pm, in accordance with the lower limit of an action of the piezoelectric element.

The diameters of amino acids may be from about 0.5 nm to 2 nm, or 0.7 nm to 1 nm (e.g., 0.8 nm). In some cases, the diameters of amino acids may be at least about 0.5 nm, 0.6 nm, 0.7 nm, 0.8 nm, 0.9 nm, 1 nm, or 2 nm. Alternatively, the diameters of the amino acids may be less than or equal to about 2 nm, 1 nm, 0.9 nm, 0.8 nm, 0.7 nm, 0.6 nm, or 0.5 nm. Because diameters of amino acids are known to those skilled in the art, multiple inter-electrode distances may be selected in accordance with the molecular diameters of the amino acids using inter-electrode distance changing unit 16.

Specific methods for fabricating nanogap electrode pair 12 are not restricted. Hereinafter, one example of the fabrication method thereof will be shown.

Nanogap electrode pair 12 may be fabricated using a known nanofabricated mechanically-controllable break junction method. A nanofabricated mechanically-controllable break junction method is an excellent method to control the inter-electrode distance with excellent mechanical stability, and with sub-picometer resolution. A method to fabricate an electrode pair by using a nanofabricated mechanically-controllable break junctions method may be found in articles, for example, "J. M. van Ruitenbeek, A. Alvarez, I. Pineyro, C. Grahmann, P. Joyez, M. H. Devoret, D. Esteve, and C. Urbina, Rev. Sci. Instrum., 67, 108 (1996)", or "M. Tsutsui, K. Shoji, M. Taniguchi, and T. Kawai, Nano Lett., 8, 345 (2008)". As to the material of the electrode, various metals such as gold may be used.

In some embodiments a nanogap electrode pair 12 may be fabricated by the procedure described hereinafter Firstly, a nanometer scale junction of gold may be patterned on a polyimide-coated flexible metal substrate using an electron beam drawing apparatus JSM 6500F (catalogue number; manufactured by JEOL Ltd.) which may utilize known electron beam lithography and lift-off technology. Then, polyimide under this junction may be removed by etching based on a known etching method (such as a reactive ion etching method) using a reactive ion etching apparatus 10NR (catalogue number; manufactured by SAMCO Inc.).

Next, by bending the substrate, a nanometer scale bridge, which may comprise gold, having a three-point bent structure may be obtained. In some embodiments, by precisely controlling bending of a substrate utilizing a piezo actuator APA 150M (catalogue number; manufactured by CEDRAT Technologies), an inter-electrode distance associated with an electrode pair can be controlled with sub-picometer resolution.

Next, ends of a fabricated bridge may be pulled so as to partially break the bridge. The ends of a fabricated bridge may be pulled further so as to set a gap length (inter-electrode distance) to a length associated with a diameter of a target amino acid, which may be about 1 nm. In some embodiments, pulling of a bridge apart forming an electrode pair may be adjusted utilizing a self-breaking technology, so that an inter-electrode distance of an electrode pair can be controlled precisely (see, "M. Tsutsui, K. Shoji, M. Taniguchi, and T. Kawai, Nano Lett., 8, 345 (2008)" and "M. Tsutsui, M. Taniguchi, and T. Kawai, Appl. Phys. Lett., 93, 163115 (2008)").

Specifically, by using a data collection board NIPCIe-6321 (catalogue number; manufactured by National Instruments Corp.) with a resistance feedback method (see, "M. Tsutsui, K. Shoji, M. Taniguchi, and T. Kawai, Nano Lett., 8, 345 (2008)" and "M. Tsutsui, M. Taniguchi, and T. Kawai, Appl. Phys. Lett., 93, 163115 (2008)"), a gold nanojunction may be pulled using a programmed junction pulling velocity by using a 10 kΩ resistance connected in series while applying 0.1 V DC bias voltage (Vb) to a bridge, to break the bridge, and to measure the position wherein a break in a bridge has occurred. Then, a bridge may be further pulled so that a gap length (inter-electrode distance) formed by breakage of a bridge may be set at an intended length. Thus, a nanogap electrode pair 12 may be formed.

Measurement power source 18 may apply a voltage to nanogap electrode pair 12. A voltage applied by measurement power source 18 to nanogap electrode pair 12 is not particularly restricted; for example, a voltage in the range of 0.25 to 0.75 V may be applied. Specific configuration of measurement power source 18 is not particularly restricted, and any known power source apparatus may be suitably used.

An electrophoresis electrode pair 20 may be disposed so as to form an electric field aligned with a moving direction of peptide 50 (arrow "A" in FIG. 16). When an electric field is formed between electrodes of electrophoresis electrode pair 20, peptide 50 may move in the direction of the electric field by electrophoresis, or may move in direction opposite to a direction of the electric field depending on the net charge of the peptide 50, wherein the net charge of the peptide may be positive or negative. That is, peptide 50 may move so as to pass thorough between electrodes of nanogap electrode pair 12.

Electrophoresis power source 22 may apply voltage to electrophoresis electrode pair 20. A voltage applied to electrophoresis electrode pair 20 using electrophoresis power source 22 may not be particularly restricted, and thus, a voltage which may control the passing velocity of peptide 50 through between electrodes of the nanogap electrode pair 12 may be suitably set. A voltage applied by electrophoresis power supply 22 to electrophoresis electrode pair 22 may be varied depending upon the anticipated charge to mass ratio of a peptide 50, and the net charge of a peptide 50. Electrophoresis power source 22 may apply voltage to electrophoresis electrode pair 20 such that the direction of the electric field formed between electrodes of electrophoresis electrode pair 20 may be reversed, such that the direction of movement of peptide 50 may be reversed directly in association with the reversal of the electric field applied by electrophoresis power supply 20, permitting one or more peptide(s) 50 to be measured multiple times wherein different gaps spacings may be utilized for different measurements. Thus, a direction of movement of peptide 50, which may be moving between electrodes of electrophoresis electrode pair 20, may be reversed to permit multiple measurements of a particular peptide. Specific configurations of electrophoresis power source 22 are not particularly restricted, and any suitable power source apparatus may be used.

In some embodiments, a fluidic pressure may be utilized to move a peptide 50 of other polymer to and through between electrodes of a nanogap electrode pair(s), wherein the nanogap electrode pair may be situated in a sealed channel. A differential pressure may be applied such that a peptide or polymer is induced to move in one direction relative to a nanogap electrode pair(s), and the differential pressure may be reversed so as to induce an opposite flow of a peptide 50 or other polymer relative to the nanogap electrode pair(s).

Ammeter 24 may measure a current (e.g., tunneling current) that may be generated when peptide 50 passes through between electrodes of nanogap electrode pair 12 to which a voltage is applied using measurement power source 18. As discussed above, inter-electrode distance d of nanogap electrode pair 12 may be changed by inter-electrode distance changing unit 16. Ammeter 24 may measure tunneling current utilizing different inter-electrode distances. Specific configuration of ammeter 24 is not particularly restricted, and thus, any known current measurement apparatus may be suitably used.

Control unit 26 may control each of the components that constitute biomolecule sequencing apparatus 10, and may also identify amino acids comprising peptide 50 based on the measured tunneling current.

Figure 17:
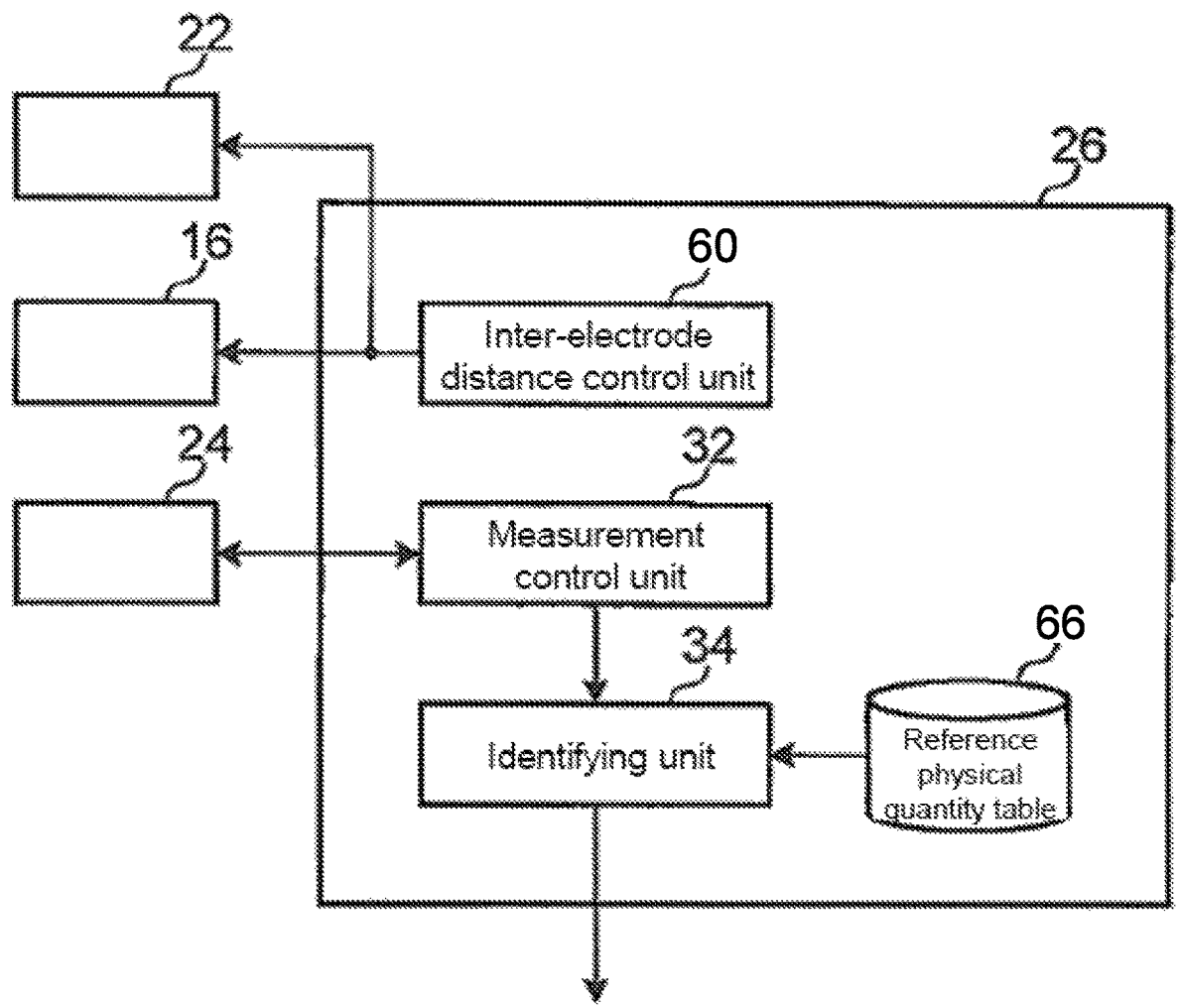
FIG. 17 is a block diagram showing a functional configuration of a control unit.

In some embodiments as shown in FIG. 17, control unit 26 may be constructed with a computer equipped with CPU (Central Processing Unit), RAM (Random Access Memory), ROM (Read Only Memory), GPU (Graphical Processing Unit) which may accommodate a biomolecule sequencing program that will be discussed later, and so forth. In some embodiments, control unit 26 associated with a computer may be functionally represented by a configuration including an inter-electrode distance control unit 30, a measurement control unit 32, and an identification unit 34. Hereinafter, each unit will be explained in detail.

In order to let peptide 50 pass through between electrodes of nanogap electrode pair 12 multiple times wherein an inter-electrode distance d of nanogap electrode pair 12 may be changed such that different measurements of peptide 50 may be effectuated with various different inter-electrode gap spacings d, wherein inter-electrode distance d of the nanogap electrode pair 12 is d1, inter-electrode distance control unit 30 may control voltage applied using electrophoresis power source 22 such that a direction of the electric field between electrodes of electrophoresis electrode pair 20 may be reversed such that the movement of peptide 50 may be reversed, allowing additional measurements to be made. After peptide 50 completes passing between the electrodes in different directions for a predetermined number of times, inter-electrode distance control unit 30 may activate inter-electrode distance changing unit 16 so as to let inter-electrode distance d of nanogap electrode pair 12 become d2 (d2≠d1) and may control a voltage applied using electrophoresis power source 22 so as to cause peptide 50 to pass again through between electrodes of nanogap electrode pair 12 between the electrodes in different directions for a predetermined number of times. Inter-electrode distance control unit 30 may cause various different inter-electrode distances to be utilized, allowing measurements to be made by nanogap electrode pair 12 with multiple inter-electrode distances d (d=d1, d2, d3 . . . ). Distances may be set to d1=1.0 nm, d2=0.7 nm, and d3=0.5 nm, for example.

As shown in FIG. 17 a measurement control unit 32 may control ammeter 24 so as to measure tunneling current for various different inter-electrode distances. Measurement time of tunneling current is not particularly restricted, and times of 10 minutes, 20 minutes, 30 minutes, 40 minutes, 50 minutes, and one hour may be used, for example. A measurement time may be suitably set in accordance with length of a peptide 50. Measurement control unit 32 may determine current values of the tunneling current measured by the ammeter 24, whereby conductances may be calculated from the current values thus determined, such that a conductance-time profile may be made. Conductance may be calculated by dividing current values of tunneling current by a voltage V applied to nanogap electrode pair 12 at the time when a tunneling current is measured. By utilizing calculated conductance values, even if a voltage applied to nanogap electrode pair 12 may be different for different measurements, a profile based on a unified standard can be obtained. In some embodiments wherein values of voltage applied to nanogap electrode pair 12 may be made constant for each measurement, a current value and a conductance associated with a tunneling current may be treated equally.

Alternatively, measurement control unit 32 may determine a tunneling current measured by ammeter 24 after tunneling current is amplified once by a current amplifier. By using a current amplifier, the value of a very weak tunneling current may be amplified, such that tunneling current may be measured with high sensitivity. As to the current amplifier, a commercially available high-speed variable current amplifier DHPCA-100 (catalogue number; manufactured by FEMTO messtechnik GmbH) may be used, for example.

Identification unit 34 may identify amino acids comprising peptide 50 by comparing detected physical quantities obtained from a conductance-time profile made by measurement control unit 32 with reference physical quantities of known kinds of amino acids which may be stored in a reference physical quantity table 36. In some embodiments, a detected physical quantity may be conductance at each measurement point of a conductance-time profile made by measurement control unit 32.

Hereinafter, a reference physical quantity stored in reference physical quantity table 36 will be explained. In some embodiments, a relative conductance for each kind of amino acids and for each inter-electrode distance d, measured with regard to known kinds amino acids, may be used as a reference physical quantity. Relative conductance may be calculated in advance by the following procedure.

Firstly, in biomolecule sequencing apparatus 10, inter-electrode distance changing unit 16 may be controlled by inter-electrode distance control unit 30 such that inter-electrode distanced may be set at d1 (for example, d1=1.0 nm). Then, after nanogap electrode pair 12 is disposed in a solution in which, from the 20 or more known kinds of amino acids, one kind of amino acids may be dissolved, voltage may be applied to electrophoresis electrode pair 20 using electrophoresis power source 22, and voltage is applied to nanogap electrode pair 12 using measurement power source 18, such that amino acids pass through between electrodes of nanogap electrode pair 12. Then, a current value of the tunneling currents generated when amino acids pass through between electrodes of nanogap electrode pair 12 may be measured by ammeter 24 for a predetermined period (for example for 50 minutes). This measured current value may be determined by measurement control unit 32 to generate a conductance-time profile. A voltage applied between electrodes of nanogap electrode pair 12 is not particularly restricted, and may be made in the range of 0.25 to 0.75 V, for example.

Figure 18:
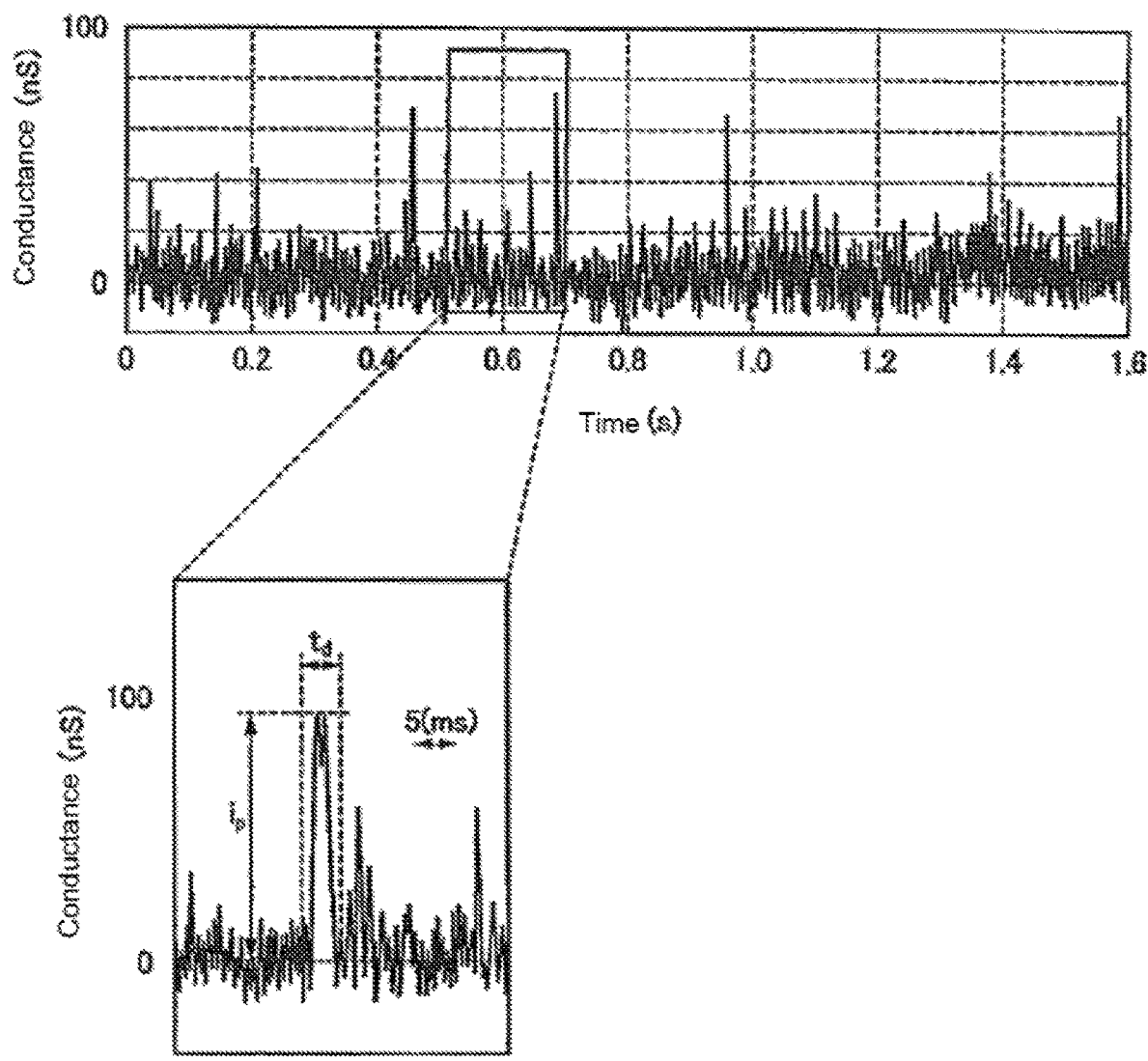
FIG. 18 is a view showing conductance and pulse duration time for a pulse.

Next, identification unit 34 may detect multiple pulses from a conductance-time profile made by measurement control unit 32, and at the same time may detect a maximum conductance $i_p$ and a pulse duration time $t_d$ for each of detected multiple pulses (See FIG. 18). The number of the detected pluses is not restricted. The more pulses are used to characterize an amino acid, the more accurately a reference physical quantity may be calculated. In addition, the number of the pulses may be increased by, for example, increasing a measurement time of tunneling current and by increasing the number of times an amino acid may be brought back and forth through electrodes of a nanogap electrode pair 12 utilizing a single nanogap distance.

Methods for detection of maximum conductance $i_p$ and pulse duration time $t_d$ will be explained more specifically. Firstly, in order to explain a method to detect multiple pulses from a conductance-pulse profile, the mechanism in which tunneling current is generated will be explained.

When peptide 50 enters between electrodes of nanogap electrode pair 12, at first, any of amino acids comprising peptide 50 may be trapped between electrodes of nanogap electrode pair 12 (hereinafter, this is referred to as a first amino acid). At a time when a first amino acid is trapped between electrodes, a tunneling current derived from a first amino acid may be generated between electrodes of electrode pair 12.

Then, after a first amino acid has passed between electrodes completely, another amino acid may be trapped between electrodes of electrode pair 12 (hereinafter, this is referred to as a second amino acid). At the time when a second amino acid may be trapped between electrodes, a tunneling current derived from a second amino acid may be generated between electrodes of electrode pair 12. Herein, a second amino acid may be an amino acid which is located next to a first amino acid, or may be an amino acid which is not next to a first amino acid.

As mentioned above, tunneling currents derived from amino acids comprising peptide 50 may be generated between electrodes of nanogap electrode pair 12. When amino acids have passed through between electrodes (when a last amino acid comprising a peptide 50 is released from between electrodes), tunneling currents generated between the electrodes may disappear or may be reduced to a background level.

In addition, identification unit 34 can detect a pulse from a conductance-time profile by identifying a conductance-rising time and a conductance-descending time in a region in which conductance corresponding to current value of a tunneling current in a conductance-time profile is above a base level. A base level may be set in advance, or may be set by confirming a conductance-time profile by an oscilloscope, or by fitting a base level to a conductance-time profile to best fit a particular conductance-time profile or the like.

In some embodiments, a base level for determination of conductance-rising and conductance-descending events may be adjusted throughout a run, potentially compensating for variations in nanogap electrode pair electrode tip variation or compensating for temperature variation induced gap spacing changes with concordant changes in expected current levels, base levels, and trapping timer intervals.

In addition, for each of detected pulses, identification unit 34 detects, a pulse duration time $t_d$, a time between a conductance-rising time and a conductance-descending time which may be identified to detect a pulse, and may also detect, a maximum conductance $i_p$, a maximum value of conductance associated with each pulse.

In some embodiments and depicted in FIG. 18 a conductance-time profile that is made by measurement control unit 32 and also in the enlarged view of the conductance-time profile shown in FIG. 3, wherein one example of a pulses, maximum conductance $i_p$, and pulse duration time $t_d$ detected by identification unit 34 is shown.

Herein, pulses derived from one kind of amino acids may be detected. However, there may be variances in maximum conductance $i_p$ and pulse duration time $t_d$, which may be detected for each pulse. A pulse in tunneling current may be generated from a change of a distance between an electrode(s) and an amino acid caused by movement of an amino acid between electrodes. That is, if a distance between an electrode(s) and an amino acid becomes shorter, a tunneling current may be generated more easily, and as a result, current values of tunneling current may increase (conductance may increase). If a distance between an electrode and an amino acid becomes larger, generation of tunneling may decrease (conductance may decrease). Because a conductance may increase and decrease in the manner described herein, variations in maximum conductance $i_p$ and pulse duration time $t_d$ of pulses may occur.

Figure 19:
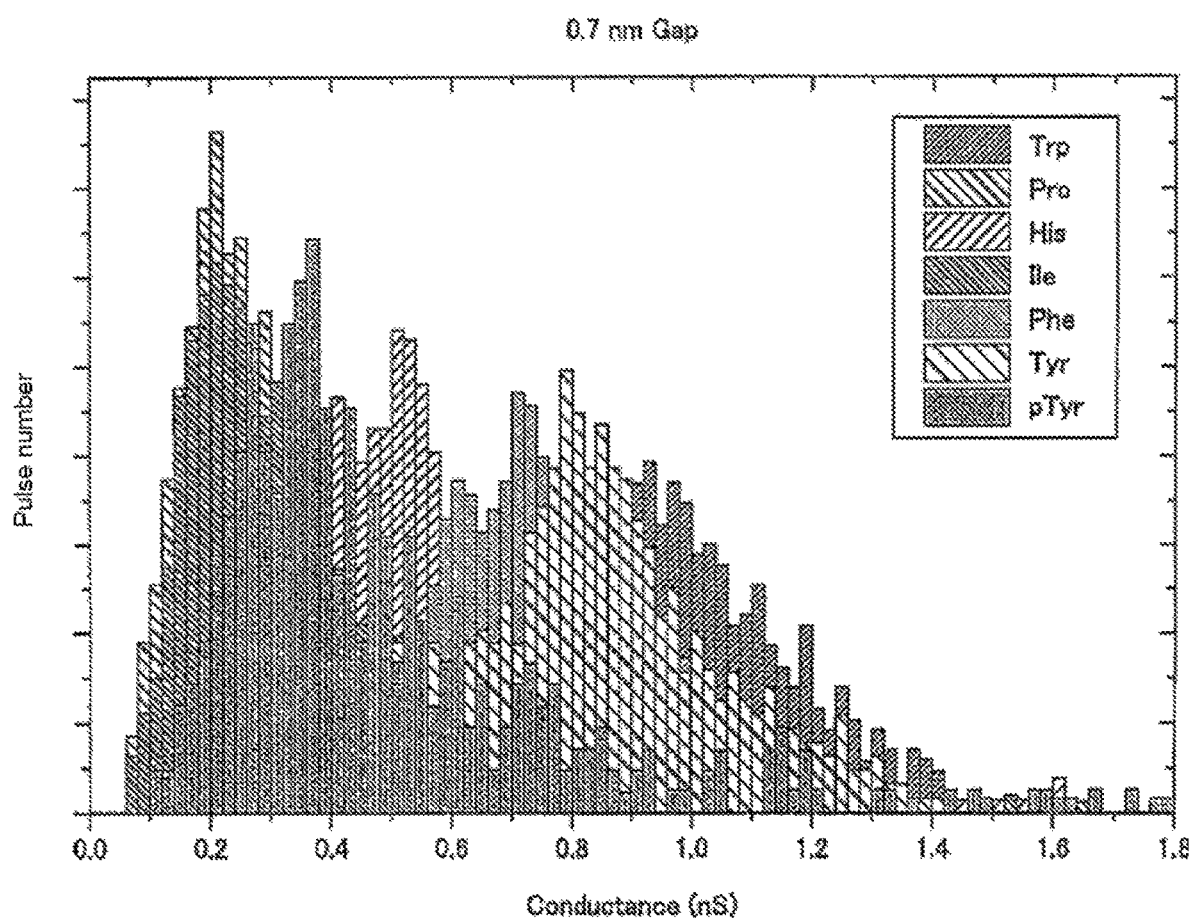
FIG. 19 is a view showing one example of a histogram of the maximum conductance.

Accordingly, mode values of maximum conductance $i_p$ and pulse duration time $t_d$ for each pulse may be calculated using statistical analysis. For example, a histogram which shows the relationship between values of maximum conductance $i_p$ and the number of pulses having this value may be formed. For example, a histogram as shown in FIG. 19 may be formed. In FIG. 19, histograms of multiple kinds of amino acids are superimposed. A predetermined function may be fitted to a formed histogram, and a mode value can be calculated from a peak value of a fitted function. A mode value of maximum conductance $i_p$ may be taken as a peak conductance Ip.

Figure 20:
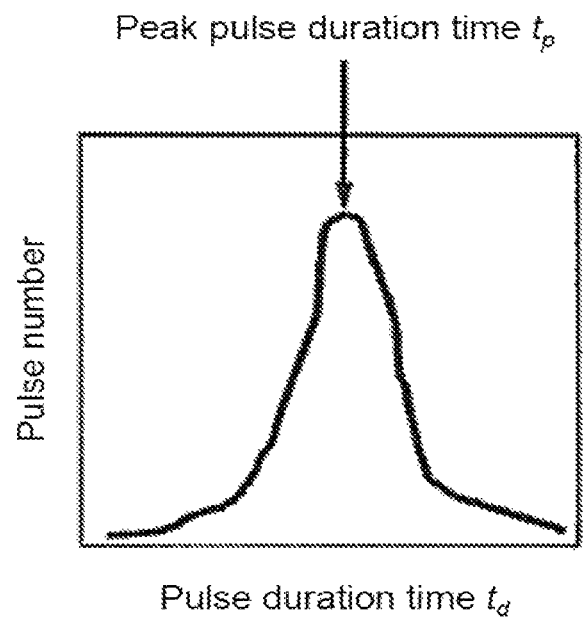
FIG. 20 is a view showing one example of a histogram of the pulse duration time.

Similarly, with regard to pulse duration time $t_d$, a histogram which shows a relationship between a value of pulse duration time $t_d$ and a number of pulses having this value may be formed. For examples, a histogram as shown in FIG. 20 can be formed. A predetermined function may be fitted to a formed histogram, and a mode value may be calculated from a peak value of this fitted function. A mode value of this pulse duration time $t_d$ may be taken as a peak pulse duration time tp.

As to a function to be used for fitting, Gaussian functions and Poisson functions and/or combinations thereof may be used, but a Gaussian function may be preferable, as when using a Gaussian function, there is an advantage resulting from increased a data processing speed.

The number of pulses to be used for the statistical analysis to calculate a mode value is not particularly restricted, and for example, a number may be in the range of 500 to 1000, or from 100 to 1000, or from 10 to 10,000. In some cases, the number of pulses used is at least about 10, 20, 30, 40, 50, 60, 70, 80, 90, 100, 200, 300, 400, 500, 1000, 5000, or 10000. Alternatively, the number of pulses used is less than or equal to about 10000, 5000, 1000, 500, 400, 300, 200, 100, 90, 80, 70, 60, 50, 40, 30, 20, or 10. If a specific number of pulses are used in statistical analysis, the statistical significance of a mode value may be calculated. A mode value is inherent to each amino acid, so that this mode value may be used as an indicator to identify a kind of amino acid.

Next, by using a calculated peak conductance Ip and a base line conductance Ib, conductance of a single amino acid molecule may be calculated by the following equation $$\text{Conductance of a single amino acid molecule} = (Ip - Ib). \quad (1):$$

Figure 21:
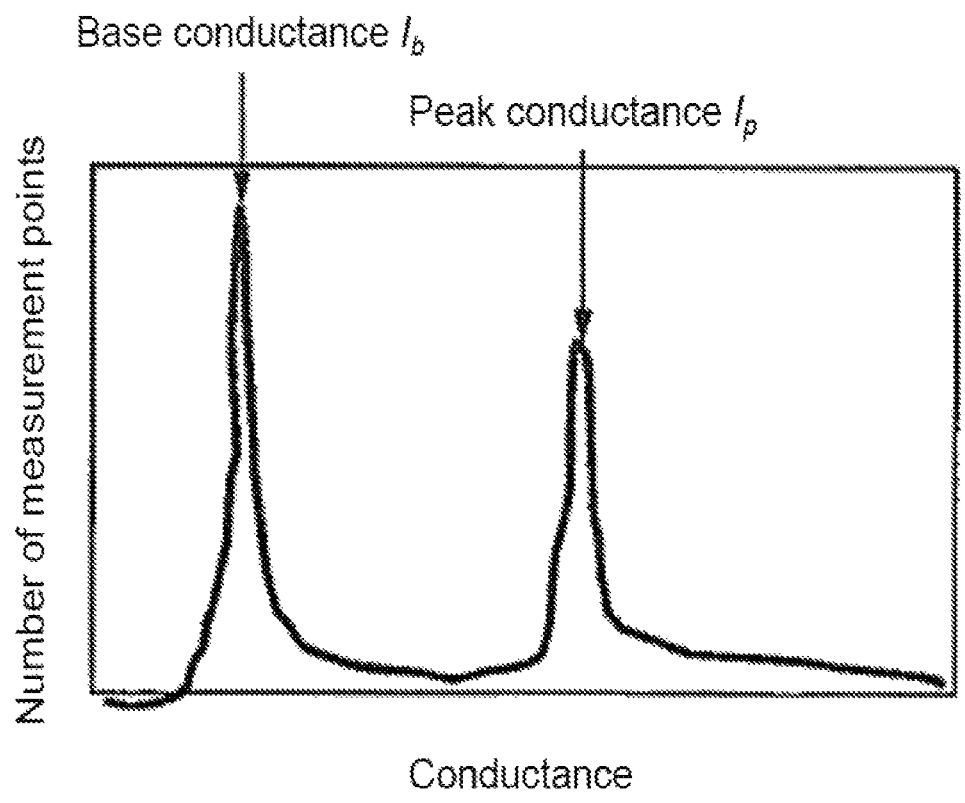
FIG. 21 is a view showing one example of a histogram of conductance.

A base line conductance Ib, which may be a value of conductance corresponding to a peak whose conductance is the lowest among peaks appearing in a histogram formed with respect to conductance of measurement points, for example, as shown in FIG. 21, may be used to determine a base line conductance Ib. In some embodiments, wherein a base line conductance may be different than a predetermine base line conductance, potentially due to the use of a different buffer, different temperature or other possible differences from the conditions utilized to generate predetermined a base line conductance, a base line conductance may be generated before sequence measurement is begun by introducing a buffer consistent with the buffer with which a set of peptides or other polymers to be measured may be in solution, and creating a new predetermined base line conductance. In other embodiments, a base line conductance may be determined from data acquired while obtaining monomer identification data, which may utilize data from between peptide(s) 50 or other polymers to set the base line conductance level. In further embodiments, wherein a baseline conductance may not be stable, for example where an operating temperature for a nanogap electrode pair may not be stable or an ionic concentration of a buffer may not be stable due to evaporation, base line conductances may be determined at several times during a peptide(s) or other polymer sequencing process. In additional embodiments, a base line conductance may be fit to data produced such that a continuous curve may be utilized wherein the continuous curve may vary with time over a peptide or other sequencing process.

As mentioned herein, a process to calculate a conductance of a single amino acid molecule may be performed with regard to different inter-electrode distances d by changing the inter-electrode distance d to d1, d2, d3, and so forth. Further, a conductance of a single amino acid molecule may be calculated for all of 20 or more kinds of amino acids for each inter-electrode distance d.

For each inter-electrode distance d, by dividing a conductance associated with each single amino acid molecule by a maximum value of conductance of a single amino acid molecule of all 20 or more kinds of amino acids, a relative conductance G associated with each single amino acid molecule may be calculated.

In FIG. 12, the relative conductances G of some amino acids for different inter-electrode distances d are shown. In non-limiting examples as shown in FIG. 12, the inter-electrode distance d may be d1=1.0 nm, d2=0.7 nm, and d3=0.4 nm. As shown in FIG. 12, when an inter-electrode d may be 0.4 nm, relative conductances G of His, Thr, Tyr, and Trp may be close to each other. Similarly, when an inter-electrode distance d may be 0.7 nm, relative conductances G of Cys and Pro, and those of Tyr and Trp may be close to each other. Similarly, when an inter-electrode distance d may be 1.0 nm, the relative conductances G of Cys, Pro, and Phe may be close to each other. If these close relative conductances G are used as indicators to identify a kind of amino acids, there is a risk that an identifying accuracy may be low.

Therefore, among relative conductances G that may be calculated from tunneling currents measured for different nanogap electrode pairs, each nanogap electrode pair may have a different inter-electrode distance, and may have a different relative conductance G associated with each different inter-electrode distance, whereby different kinds of amino acids may be identifiable with different predetermined accuracies associated with each inter-electrode distance.

Whether or not the kind of amino acids is identifiable with predetermined accuracy by a particular relative conductance may be judged, for example, by the following procedure.

Figure 22:
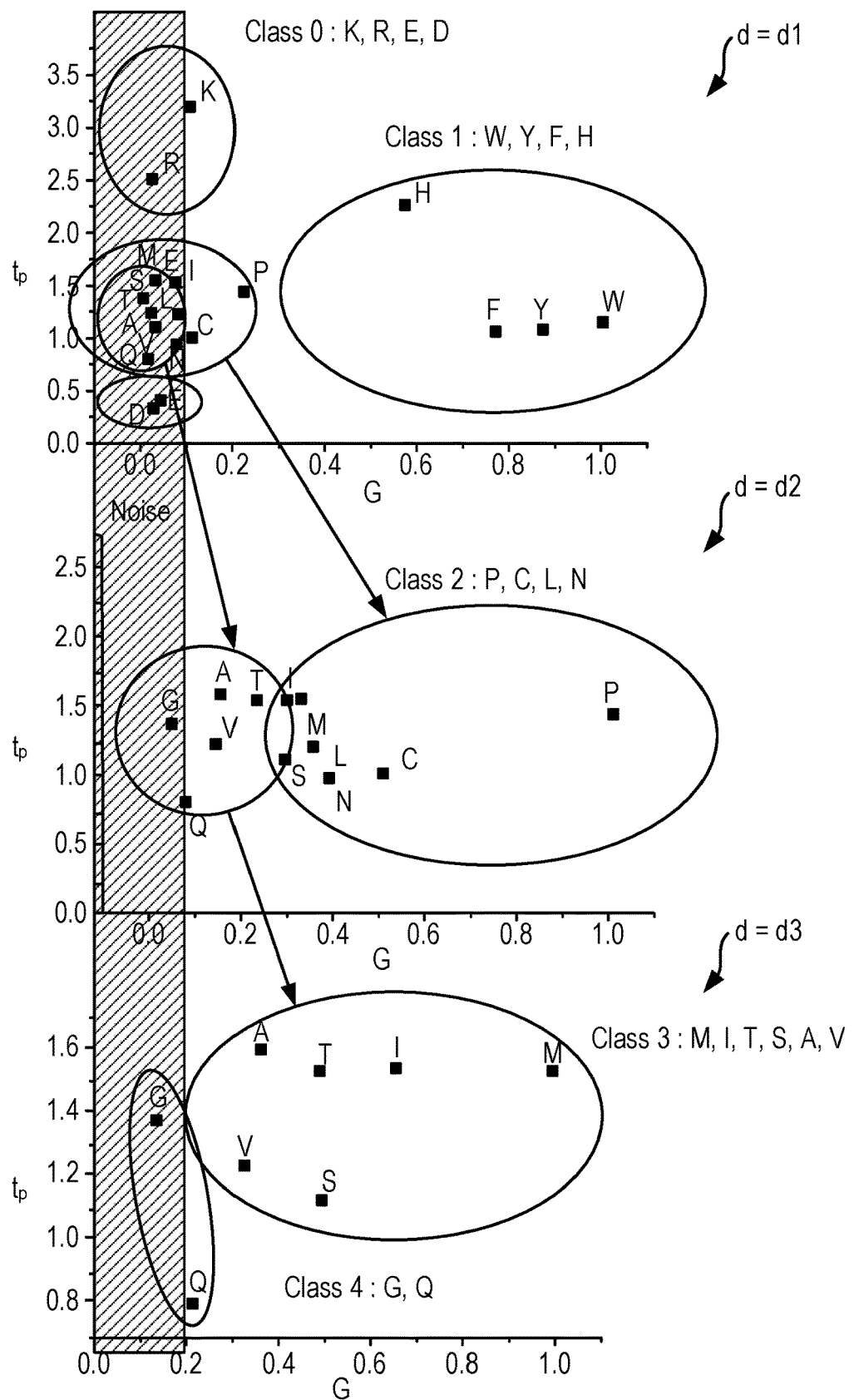
FIG. 22 is a view for showing reference physical quantities for different inter-electrode distances.

As shown in the view in the upper part of FIG. 22, values of relative conductances G, which may be calculated from tunneling current measured with an inter-electrode distance d being d1, and values of peak pulse duration times $t_p$ may be mapped in a $t_p$-G space. Mapped points may be classified into different classes by using cluster analysis. For cluster analysis, known methods may be used, wherein if each point contained in each class can be all separated from other points, and at the same time, at least one point among all points contained in each class is present outside a noise region (the shaded region in FIG. 22), then a relative conductance G shown by a point that belongs to the class is judged to be a relative conductance with which the kind of amino acid can be identified with a predetermined accuracy. The case for which each point contained in each class can be all separated from other points describes a case wherein, for example, all the distances among points are more than a previously determined threshold value.

In the view of the upper part of FIG. 22, it is shown that all points corresponding to amino acids K, R, E, and D which are classified into class 0 as well as all the points corresponding to amino acids W, Y, F, and H which are classified into class 1 may be separated. In addition, all points contained in class 0 and all points contained in class 1 may be present outside a noise region. Accordingly, it may be judged that, using relative conductances G shown by each point contained in class 0 and class 1, the kinds of amino acids corresponding to the respective points can be identified with a predetermined accuracy. Therefore, the kinds of amino acids corresponding to the respective points contained in class 0 and class 1 and relative conductances G shown by respective points may be stored in a reference physical quantity table in relation to an inter-electrode distance d (d=d1 in the example of the view of the upper part of FIG. 22).

The view of the upper part of FIG. 22 shows that all points contained in classes other than class 0 and class 1 are either not fully separable, or points contained in the classes may be present in a noise region. Therefore, as shown in the view in the middle part of FIG. 22, amino acids that are not judged to be identifiable with a predetermined accuracy, values of relative conductances G, which are calculated from tunneling currents measured with an inter-electrode distance d which may be d2, and the values of peak pulse duration times tp may be mapped in a tp-G space. The mapped points may be classified into each class. In the view of the middle part of FIG. 22, it is shown that all the points corresponding to amino acids P, C, L, and N may be classified into class 2, and may be separated. In addition, all points contained in class 2 may be present outside a noise region. Accordingly, it can be judged that, by relative conductances G shown by each point contained in class 2, amino acids corresponding to the respective points can be identified with a predetermined accuracy. Therefore, amino acids corresponding to respective points contained in class 2 and relative conductances G shown by respective points may be stored in a reference physical quantity table in relation to an inter-electrode distance d (d=d2 in the example of the view of the middle part of FIG. 22).

The view in the middle part of FIG. 22 shows that all points contained in classes other than class 2 are either not separable, or points contained in the classes may be present in a noise region. Therefore, as shown in the view of the lower part of FIG. 22, amino acids that are not judged to be identifiable with a predetermined accuracy, values of relative conductances G, which may be calculated from tunneling currents measured when an inter-electrode distance d which may be d3, and values of peak pulse duration times tp may be mapped in a tp-G space; and mapped points may be classified into each class. In the view of the lower part of FIG. 22, it is shown that all the points corresponding amino acids M. I. T, S, A, and V which are classified into class 3, as well as all points corresponding to amino acids G and Q, which are classified into class 4 may be separated. In addition, all each points contained in class 3 and all points contained in class 4 are present outside a noise region. Accordingly, it can be judged that, using relative conductances G shown by points contained in class 3 and class 4, the amino acids corresponding to the respective classes may be identified with a predetermined accuracy. Therefore, amino acids corresponding to the respective points contained in class 3 and class 4 and relative conductances G shown by the respective points may be stored in a reference physical quantity table in relation to an inter-electrode distance d (d=d3 in the example of the diagram of the lower part of FIG. 22).

Accordingly, in the above examples, with regard to the amino acids belonging to class 0 and class 1, relative conductances G, which may be calculated from tunneling currents measured with an inter-electrode distance d which may be d1, may be used as reference physical quantities. With regard to the amino acids belonging to class 2, relative conductances G, which are calculated from tunneling currents measured with an inter-electrode distance d which may be d2, may be used as reference physical quantities. And with regard to amino acids belonging to class 3 and class 4, relative conductances G, which may be calculated from tunneling currents measured with an inter-electrode distance d which may be d3, may be used as reference physical quantities.

As discussed above, among relative conductances G which may be calculated from currents (e.g., tunneling currents) measured using different sets of nanogap electrode pairs, wherein each nanogap electrode pair may have a different inter-electrode distance, the relative conductance G with which the kinds of amino acids may be identified with a predetermined accuracy (e.g., an accuracy that is greater than 80%, 90%, 95%, or 99%) may be selected with regard to each inter-electrode distance and stored in a reference physical quantity table or matrix. This can be calculated (e.g., interpolated) for intermediate distances. Data from distances, which may be in a noise region or not fully determinable, may be used to provide better certainty.

Under interpolation, a given function, which may be a polynomial function, a logarithmic function, an exponential function, or any other function or combination of functions, may be determined to represent a curve based upon a best fit to existing data, and a relationship between a new data point and the curve may be utilized to determine a corresponding value associated with the new data point. In an example, a function may be determined between, for example, a tunneling current of a reference substance and an inter-electrode distance. The function may be based on a combination of measurements and tunneling current theory, and an additional function may be determined between inter-electrode distance and tunneling current of, for example, an amino acid or a nucleic acid molecule (or other biomolecule), in which the function may again be derived from a combination of measurements and tunneling current theory. Based on measured tunneling currents associated with a reference substance, an expected tunneling current may be determined for, for example, an amino acid. Tunneling current theory analysis may include analysis of a highest occupied molecular orbital and a lowest unoccupied molecular orbital or a molecule.

An identification unit may identify amino acids by comparing a conductance at each measurement point (detected physical quantity) of a conductance-time profile, which may be based on current values of tunneling currents measuring a peptide to be identified, and relative conductance G (reference physical quantity) of known kinds of amino acids, which may be calculated as mentioned herein and stored in a reference physical quantity table, so that the sequence of the amino acids comprising a peptide may be determined. Details of an identification procedure(s) will be discussed later.

Figure 23A:
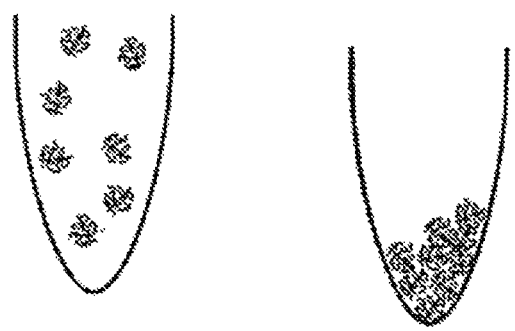
FIGS. 23A-23C are views showing procedures for preliminary preparation.
Figure 23B:
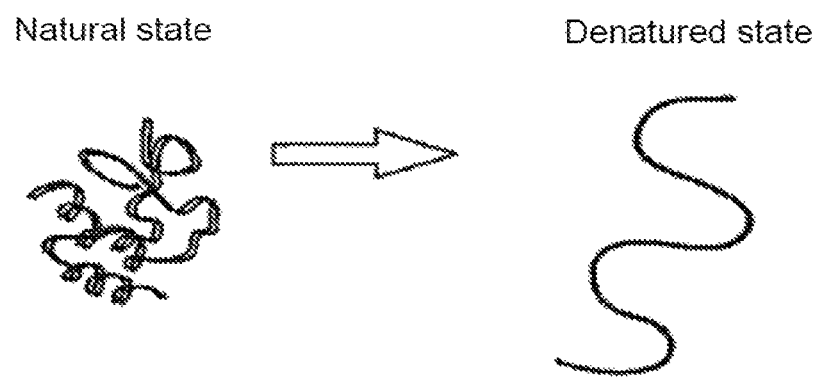
Figure 23C:
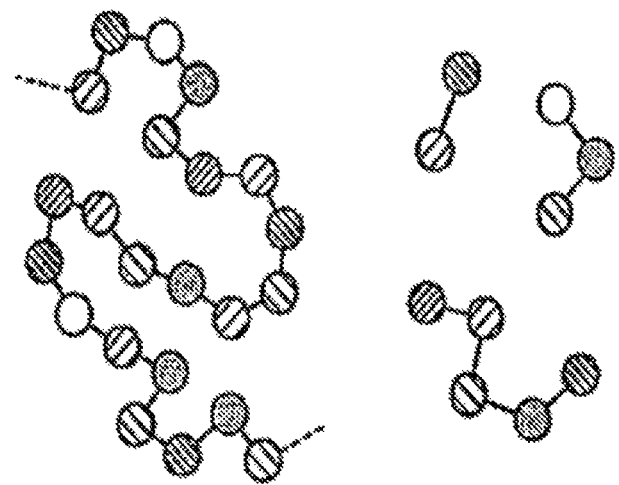

Next, operation of a biomolecule sequencing apparatus will be explained. At the beginning, as shown in FIG. 23A, a sample may be taken from a sample source, and extraction and purification of protein(s) may be performed. Then, as shown in FIG. 23B, a denaturation agent (hydrogen bond inhibitor) may be added to protein thus extracted and purified so as to denature protein from a three-dimensional structure to a linear structure. Thereafter, as shown in FIG. 23C, protein, which may be denatured to a linear structure, may be cleaved into peptides by a selective breakage of the chain using enzymes such as proteases such as trypsin, pepsin, elastase, diacetoxyiodobenzene, or chymotrypsin or by chemical cleavage agents such as iodosobenzoic acid or cyanogen bromide, or may be cleaved using an ultrasonic method, or exposure to UV light; cleavage may be aided by selection of temperature, whereby a selected temperature may typically be above ambient.

Next, peptides thus obtained may be dissolved into a solution. A solution is not particularly restricted, and the same solution as the one in which amino acids are dissolved to measure reference physical quantities may be used. For example, ultrapure water may be used. Ultrapure water may be prepared by using, for example, Milli-Q Integral 3/5/10/15 (catalogue number with the apparatus name of Milli-Q Integral 3; manufactured by Merck KGaA). Concentration of peptide 50 in a solution is not particularly restricted, and a concentration in the range of 0.01 to 1.0 µM may be used, for example. A concentration of peptide 50 in solution may be from about 0.01 µM to 1.0 µM, or 0.01 µM to 0.5 µM. In some cases, the concentration of peptide 50 in solution is less than about 5 µM, 4 µM, 3 µM, 2 µM, 1.5 µM, 1 µM, 0.5 µM, 0.1 µM, or 0.01 µM. As an alternative, the concentration of peptide 50 in solution is more than about 0.01 µM, 0.1 µM, 0.5 µM, 1 µM, 1.5 µM, 2 µM, 3 µM, 4 µM, or 5 µM.

Figure 24:
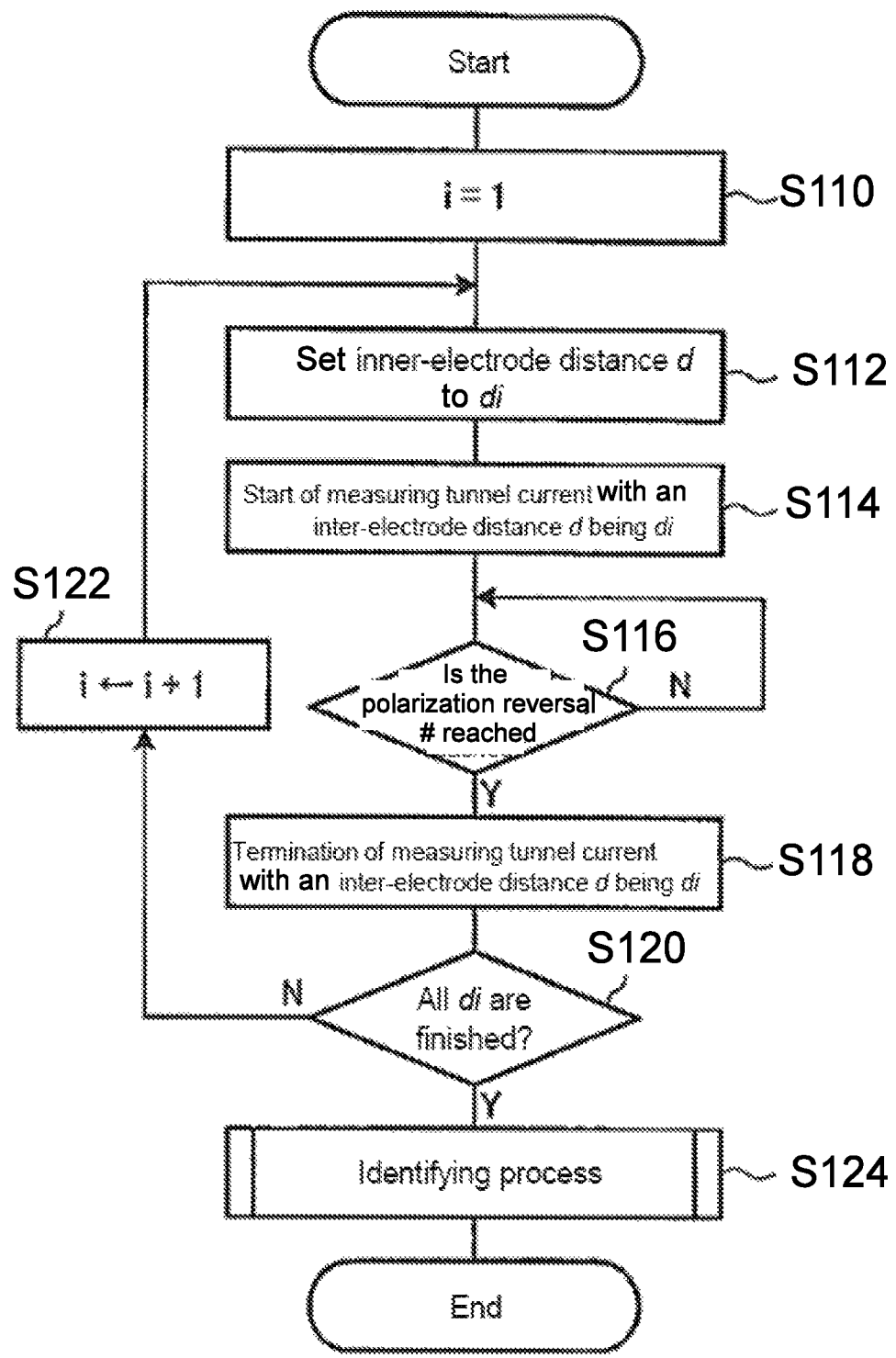
FIG. 24 is a flowchart showing a biomolecule sequencing process.

After a nanogap electrode pair is disposed in a solution in which peptides are dissolved, voltage may be applied to a nanogap electrode pair using a measurement power source, and voltage may be applied to an electrophoresis electrode pair using an electrophoresis power source. Then, a CPU of a computer which may comprise a portion of a control unit may read and execute a biomolecule sequencing program which may be stored in ROM, RAM, FLASH or other appropriate digital storage media, and by this, a processing of biomolecule sequencing as shown in FIG. 24 may be carried out with a biomolecule sequencing apparatus. In some embodiments, processing of biomolecule sequencing may be carried out by a biomolecule sequencing apparatus.

In step of S110 of processing of biomolecule sequencing as shown in FIG. 24, an inter-electrode distance control unit may set a variable i to a value of 1. Then in step S112, an inter-electrode distance control unit may controls an inter-electrode distance changing unit such that an inter-electrode distance d may be adjusted to a distance di. Voltage may be applied between electrodes of an electrophoresis electrode pair 20, so that peptide(s) may pass through between the electrodes of an nanogap electrode pair whose inter-electrode distance d may have been set to a distance di.

Next, in step S114, a measurement control unit may control an ammeter and start measurement of current values of tunneling current that may be generated when peptide(s) may pass through between the electrodes of a nanogap electrode pair with an inter-electrode distance d which may have a distance di. A measurement control unit may take measured current values and store them in a predetermined memory area associated with the measurement time of each measurement point.

Then, in step S116, an inter-electrode distance control unit may determine whether or not peptide(s) have caused to reverse direction for prescribed number of times between the electrodes of a nanogap electrode pair with an inter-electrode distance d which may be a distance di. This determination may be made by a number of electrophoresis voltage polarization reversals made using an electrophoresis power source. When a number of electrophoresis voltage polarization reversals have not reached a predetermined number, electrophoresis voltage polarization reversal step(s) are repeated. When a number of electrophoresis voltage polarization reversals reaches a predetermined number, operation moves to step S118, and a measurement control unit may terminate measurement of tunneling current with an inter-electrode distance d which may be a distance di, and from obtained current values and measurement times, a conductance-time profile, for example, as shown in the upper view of FIG. 18, may be formed, which may then be stored in a predetermined memory area associated with inter-electrode distance di.

Next, in step S120, an inter-electrode distance control unit may determine whether or not a process to measure tunneling current has completed measurements for all of predetermined inter-electrode distances di. If there are any unprocessed inter-electrode distances di, operation moves to step S122, where an inter-electrode distance control unit may increment variable i by 1, and operation may returns to step S112. If a process to measure tunneling current has been performed for all inter-electrode distances di, operation may move to step S124 to carry out an identification process as shown in FIG. 25.

Figure 25:
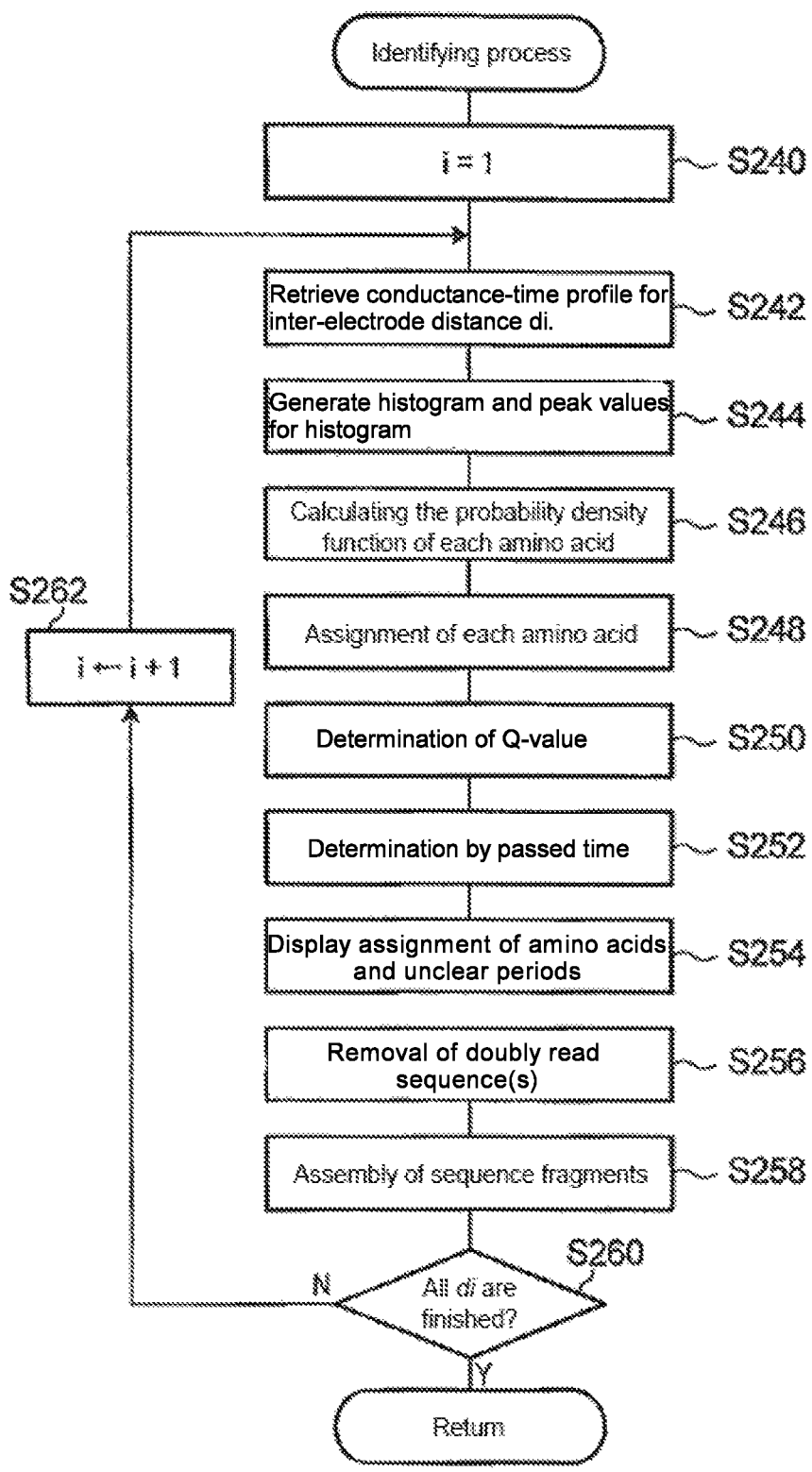
FIG. 25 is a flowchart showing an identification process.

In step S240 of an identification process as shown in FIG. 25, an identification unit may set variable i to a value of 1. Then, in step S242, an identification unit may retrieve a conductance-time profile stored in a predetermined memory area associated with an inter-electrode distance d which may have a distance di.

Figure 26:
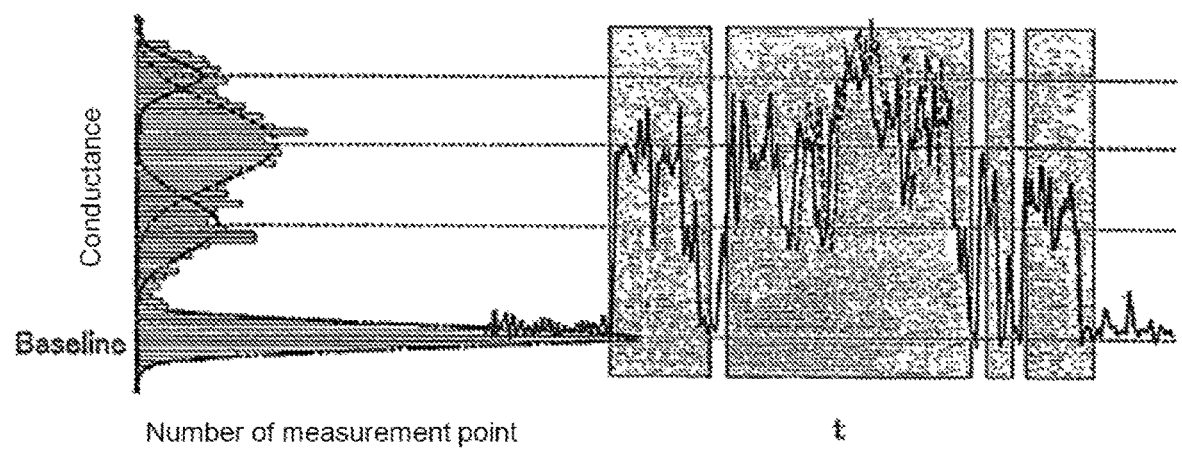
FIG. 26 is a view showing a conductance histogram used to explain calculation of a probability density function for a kind of amino acid.

Next, in step S244, based on a conductance-time profile determined by a measurement control unit, an identification unit may form a histogram showing a relationship between a conductance value for each measurement point and a number of measurement points having this value. Then, an identification unit may detect a histogram peak by fitting a predetermined function to a formed histogram. For example, as shown in FIG. 26, an identification unit may detect multiple peaks appearing in a histogram and may calculate a peak value associated with each peak. Then, an identification unit may identify the order and type of amino acids contained in a peptide by comparing calculated peak values with relative conductances G corresponding to inter-electrode distance di, which may be relative conductances G of respective amino acids that may be stored in a reference physical value table.

In some embodiments, identification performed in step S244 may be performed at a time a data set is generated, or may be performed as a post processing step, or may be performed as a part of data streaming step wherein data processing occurs while more data is being taken. In some embodiments, identification may be performed using data from a single nanogap electrode spacing wherein the single nanogap electrode spacing may have be inter-electrode nanogap electrode pair spacing which may have produced data which may be better at distinguishing an identified monomer than other inter-electrode nanogap electrode pair spacings from other available nanogap electrode pairs or other inter-electrode gap spacings for the same nanogap electrode pair for which data was utilized. In other embodiments identification may utilize a single nanogap electrode pair spacing which provides a highest certainty of identification, even the data used is not from a nanogap electrode pair spacing which should nominally be a preferred inter-electrode nanogap electrode pair spacing.

In other embodiments, data may be utilized from multiple inter-electrode nanogap electrode pair spacings with the same or different inter-electrode gap spacings, and which may be produced by one or several nanogap electrode pairs. In some embodiments, nanogap electrode pair data which may be utilized may include inter-electrode nanogap electrode pair spacings with an inter-electrode nanogap spacing which may be partly or completely within a noise band as described in conjunction with FIG. 22. Any number of different combinations of inter-electrode nanogap electrode pair spacings may be utilized, such that an a highest quality score may be produced; in further embodiments, a limited number of inter-electrode nanogap electrode pair spacings may be utilized so as to reduce a quantity of computer processing required, while still providing an improved quality score relative to utilizing a single inter-electrode nanogap electrode pair spacing. In some embodiments, a fixed number of inter-electrode nanogap electrode spacings may be utilized, while in other embodiments a number of inter-electrode nanogap electrode gap spacings may be variable, and may be varied so as to provide a minimum number of inter-electrode nanogap electrode spacings needed to provide a predetermined quality score.

In some embodiments as described herein nominally fixed inter-electrode nanogap pair spacings may be assumed to be fabricated and used for one or more nanogap electrode pairs, without compensating for possible manufacturing tolerances or tip modifications which may occur during usage. In other embodiments, inter-electrode nanogap electrode pair spacing(s) may be determined as a result of measurements of reference substances and or monomers, wherein a set of data may be acquired prior to determination and assignment of an inter-electrode nanogap electrode pair spacing, wherein the determined inter-electrode nanogap electrode pair spacing may be utilized thereafter. In further embodiments, an inter-electrode nanogap spacing may reevaluated on an ongoing basis, either periodically or continuously throughout a sequencing process, and either discrete values from a table or interpolated or otherwise calculated expected current values may be utilized for assignment associated with different nanogap electrode pairs in concordance with measured values for the nanogap electrode pair in keeping with measured values for references substance(s) and or monomers. In further embodiments, inter-electrode distances may be determined in conjunction with monomer assignment, wherein an inter-electrode distance may be assigned as a part of monomer assignment, whereby a combination of inter-electrode nanogap electrode pair spacing and monomer may be adjusted over a period of time so as to provide a best fit metric with an optimal score.

In some embodiments, a fixed amount of data may be acquired as described herein; in other embodiments, a variable amount of data may be acquired, wherein a number of reversals and concordant traverses may be varied as a function of a quality metric, which may be a quality metric for monomer identification, or may be a simpler metric, such as a signal to noise metric or other metric which may not be directly related to a monomer identification.

In some embodiments, a period of time for a sequencing assay may be predetermined, or fixed number of sequencing cycles wherein single or sets of polymers may be subjected to repeated measurements may constitute a single sequencing cycle, so that a plurality of sequencing cycles may allow for multiple sets of single or sets of polymers to be measured, potentially multiple times with multiple reversing traversals. In other embodiments, a period of time of a number of sequencing cycles may be determined as a function of data measured during a sequencing process, wherein measurement results which may include the quality of data, signal to noise of data, frequency or duty cycle of occupancy of nanogap electrode pairs which may correlate with an number of monomers sequenced may be utilized singly or in combination so as to determine when a sequencing process should cease.

In some embodiments, a sequence assignment and associated quality metric or score may be determined for each polymer, and may be determined separately for each traversal of a nanogap electrode pair(s). In other embodiments, a sequence assignment and associated quality metric or score may be determined for a polymer as a function of several traversals and associated measurements by a nanogap electrode pair(s). In further embodiments, a sequence assignment may be made ore may be re-evaluated as a part of sequence mapping or assembly process, wherein an assignment of a monomer may be re-evaluated, and may be reassigned. Particularly wherein a quality score associated with a monomer assignment for a polymer which is not in concordance with other monomers in a same position in other polymers, a monomer assignment may be changed so as to allow mapping or assembly of different polymers which may be significantly well aligned otherwise.

In some embodiments, equal probability may be given to the likelihood of a particular monomer relative to any other monomer in a polymer when performing an assignment. In other embodiments, particularly when a resequencing a polymer, a probability distribution may be utilized which may be a global probability distribution which is then applied to all monomer assignments, or may be a localized probability distribution wherein a context of local monomer assignments may be a part of the probability distribution.

Next, in step S246, an identification unit may calculate a probability density function corresponding to respective amino acids whose relative conductances G may be stored in a reference physical quantity table. For example, a probability density function may be calculated using a Gaussian function shown by the following equation (2):

$$p(x) = \frac{1}{\sigma\sqrt{2\pi}} \exp\left(-\frac{(x-\mu)^2}{2\sigma^2}\right)$$

Here, $\mu$ represents a relative conductance G for an amino acid, and $\sigma$ represents a standard deviation. Other probability density functions such as Gibbs distribution, a Conway-Maxwell-Poisson distribution, a Zipf distribution, or any other distribution or combination of distributions may be utilized.

Next, in step S248, by using conductance values at each measurement point of a conductance-time profile and a probability density function for each amino acid, which may be a probability density function calculated in step S246, an identification unit may determine a probability that a conductance value at a measurement point is associated with an amino acid, and may assign a kind of amino acid whose probability may be maximized for a particular measurement point.

Next, in step S250, an identification unit may detect a transition point at which a conductance associated with an assigned kind of amino acid changes in a conductance-time profile, and may divide a conductance-time profile into intervals at each detected transition point. That is, for each interval, measurement points are mapped to amino acids with similar data signatures. An identification unit may determine a degree of accuracy for assignment of each amino acid for each interval by utilizing a Q-value. A Q-value or Phred quality score may be expressed, for example, by the following equation (3): $Q = -10 \log_{10} P$. Here, P may be an error probability of an amino acid assigned for a measurement point. A probability value $P^*(=1-P)$ of an assigned amino acid may be expressed as $P^* = S1/(S1+S2)$ by using a time integration value S1 of a probability of an assigned amino acid for each interval and a time integration value S2 of a probability for other amino acids for each interval. In this case, if a Q-value is 6 or more, a probability value $P^*$ of the amino acid which may be assigned to an interval may have an accuracy of 75% or more.

A Q-value or other quality metric may be stored with an assigned monomer (amino acid) sequence, and may be stored using a lossless or lossy storage method, such as a FastQ format, or may be stored using an SCALCE, Fastqz, Qualcomp, or other similar algorithm.

In some embodiments, identifiable kind(s) of amino acid(s) may differ for each inter-electrode distance di, so that kind(s) of amino acids shown by a conductance for each interval may not necessarily correspond to the kind(s) of amino acid(s) identifiable for a specific inter-electrode distance di. Therefore, if assignment of an amino acid may not have a predetermined accuracy (wherein a Q-value may be more than or equal to a previously determined threshold value), an identification unit may determine that assignment of a kind of amino acid may be unclear, and may not specifically assign an amino acid to a particular measurement point.

Next, in step S252, an identification unit may determine whether a kind of amino acid assigned to an interval is correct or not by comparing a passing time (time length of the interval) of an amino acid assigned to an interval with a passing time parameter previously determined for an amino acid.

Herein, a passing time parameter may be previously determined, for example, as following wherein a tunneling current, which may be generated when a single molecule of a known kind of amino acids may be passed through between the electrodes of a nanogap electrode pair, may be measured, and a conductance-time profile may be made. Then, from variation of conductance values, a passing time of the amino acid may be measured. A tunneling current may be measured multiple times by changing the passing direction of an amino acid. Then, passing times for each measurement may be averaged, and a value in a prescribed range including an average value may be taken as a passing time parameter for a particular amino acid.

If a time length for an interval is included in a passing time parameter for a kind of amino acids assigned to an interval, an identification unit may determine whether a kind of amino acids assigned to an interval may be correct. If the time length of an interval is not included in a passing time parameter, an "unclear" determination may be made without assigning any kind of amino acid to all measurement points included in an interval.

Figure 27:
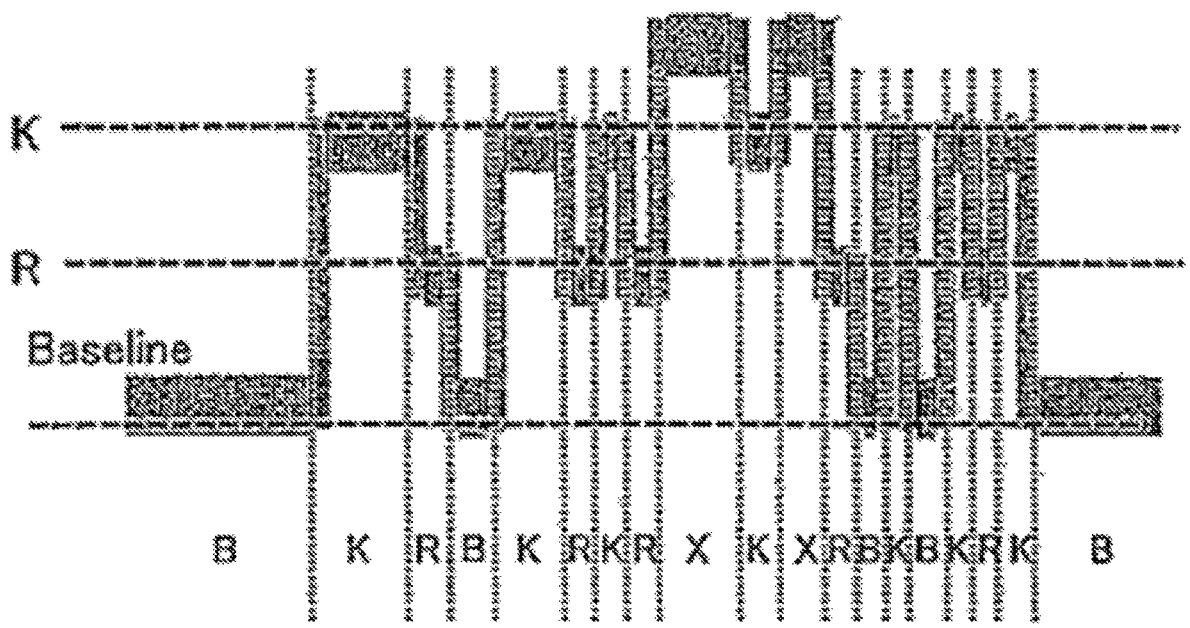
FIG. 27 is a view for explaining assignment of identified kinds of amino acids.

Next, in step S254, based on the assignment and determination results from steps S248 to S252, for example, as shown in FIG. 27, a single-letter expression showing the kind of amino acid assigned to each interval in a conductance-time profile associating an identification result corresponding to an interval. When an amino acid is not identified, a letter showing that the kind of amino acid corresponding to an interval may not be clear may be displayed (for example, a letter "X"; hereinafter referred to as an "unclear letter X". In FIG. 27, "B" shows a base line.

Next, in step S256, an identification unit may remove any doubly read sequence(s). For example, for the case of a peptide having an amino acid sequence of KRED, a correct reading is KRED; however, if movement of a peptide may be reversed at R, there is a possibility that a duplicated sequence such as KRKRFD may be read out. Therefore, an identification result having a duplicated sequence portion may be determined to be misidentified, and thus, an identification result may be changed to "unclear". That is, a letter associated with a conductance time profile, which may have been inappropriately identified in step S254 may be substituted by an unclear letter X.

Specifically, an identification unit may calculate a Q-value, which may utilize a calculation similar to equation (3), wherein each partial sequence with a letter sequence assigned in step S254 may be divided at base line "B". Herein, P may be an error probability for a particular partial sequence. A probability value $P^*(=1-P)$ for a particular partial sequence may be expressed as $P^*=S1/(S1+S2)$ by using a number S1 for a partial sequence having the same identification result as a partial sequence thereof and a number S2 for a partial sequence having another identification result. For example, for all divided partial sequences, if a partial sequence 1 (XXXAXXXX) appears five times and a partial sequence 2 (XXXLXXXX) once, then the Q-value for partial sequence 1 may be 7.78. If this Q-value is not less than a previously determined threshold value, partial sequence 1 may be determined to be correct. On the other hand, partial sequence 2 may be determined to be misled.

Next, in step S258, an identification unit may assemble (or map) sequence fragments. Specifically for a resequencing case (known sequence), sequences which have been identified (read) by steps in the process (as described herein) up to step S254 may be mapped to a reference sequence, and this operation may terminate when a certain coverage depth (number of the overlapped reads per amino acid) is attained. In the case of de novo sequence identification, contigs may be assembled by merging concordant sequences.

Figure 28:
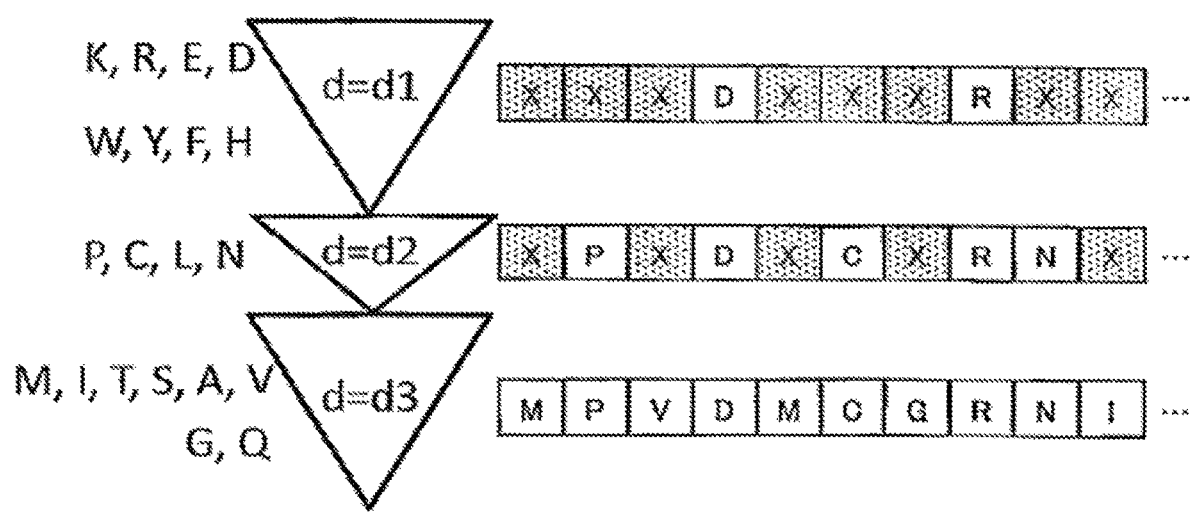
FIG. 28 is a view showing identification of different types of amino acids for different inter-electrode distances.

Next, in step S260, an identification unit may determine whether or not a process to identify amino acids by using relative conductances corresponding to different inter-electrode distances di is complete. In the case that unprocessed inter-electrode distances di are present, an operation may proceed s to step S262 and may increment a variable i by 1, and operation may return to step S242. Thus, as shown in FIG. 28, the kinds of amino acids corresponding to each interval may be identified serially by using relative conductances of amino acids identifiable with different inter-electrode distances di. When the process is over with regard to all inter-electrode distances di, a sequence result for amino acids comprising a peptide may be output, and a biomolecule sequencing process shown in FIG. 24 may terminate a biomolecule sequencing process.

As discussed herein, in some embodiments a biomolecule sequencing apparatus, may generate and measure tunneling current when a biomolecule passes through between a nanogap electrode pair for each distance for which the electrodes of a nanogap electrode pair may be set, wherein each distance for between the electrodes of a nanogap electrode pair may have a different inter-electrode distance, and may use as a reference physical quantity the physical quantities of an amino acid which may be identifiable with a predetermined accuracy in accordance with a inter-electrode distance, monomers comprising a biomolecule may be identified with a simple configuration and with high accuracy.

In some embodiments wherein some parts may be identical to those of the biomolecule sequencing apparatus of FIG. 1 as described herein, a detailed explanation of those parts which are identical will be omitted by using the same numeral references.

Figure 29:
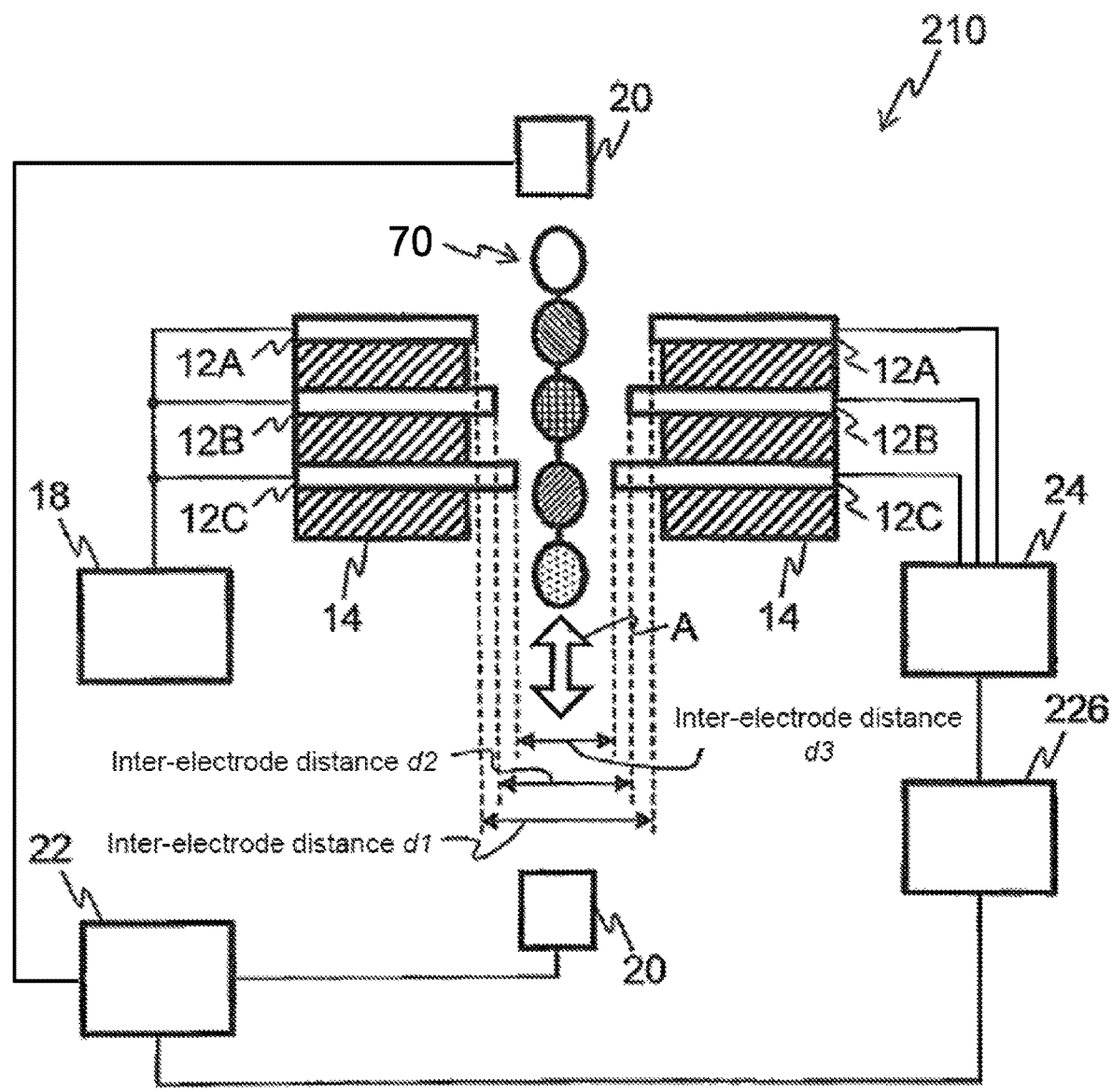
FIG. 29 is a schematic view showing a configuration of a biomolecule sequencing apparatus.

In some embodiments as shown in FIG. 29, a biomolecule sequencing apparatus 210 may include nanogap electrode pairs 12A, 12B, and 12C, measurement power source 18, electrophoresis electrode pair 20, electrophoresis power source 22, ammeter 24, and control unit 226. The electrode pairs 12A, 12B and 12C can have different gap sizes, which may be used to interrogate different substances (see, e.g., FIG. 12).

The configurations of nanogap electrode pairs 12A, 12B, and 12C may be the same as for a nanogap electrode pairs 12 as described elsewhere herein. Nanogap electrode pairs 12A, 12B, and 12C may be laminated via the dielectric(s) 14 such that the inter-electrode centers may be arranged on the same axis. That is, one passage through which a peptide 50 may pass may be formed between the electrodes of nanogap electrode pairs 12A, 12B, and 12C. An inter-electrode distance for nanogap electrode pair 12A may be d1, an inter-electrode distance for nanogap electrode pair 12B may be d2, and an inter-electrode distance for nanogap electrode pair 12C may be d3, and thus, the distances of the inter-electrode gap pairs may be different from each other. In the example of FIG. 29, they may be d1>d2>d3. For example, they may be set to d1=1.0 nm, d2=0.7 nm, and d3=0.5 nm.

In other embodiments, wherein it may be difficult to control with sufficient precision an inter-electrode gap distance, a set of nanogap electrode pairs may be fabricated with a range of inter-electrode distances, which may span a desired or predetermined range, and may have a number of nanogap electrode pairs which is equal to a minimum number corresponding to a number of inter-electrode distances needed to resolve a set of monomers (e.g., amino acids) with a desired Q-score, or may have a number of nanogap electrode pairs which is greater than a minimum number of inter-electrode distances, wherein the inter-electrode distances may provide a sufficient number of different over a sufficient range of inter-electrode distances so as to resolve a set of monomers (amino acids) with a desired Q-score. In use, reference substance(s) may be utilized so as to measure actual inter-electrode distances for different nanogap electrode pairs in a set of nanogap electrode pairs.

In some situations, a nanogap can include at least 1, 2, 3, 4, 5, 6, 7, 8, 9, 10, 11, 12, 13, 14, 15, 16, 17, 18, 19, 20, 30, 40, or 50 electrode pairs. In some cases, at least some of the electrode pairs have different gap sizes than other electrode pairs. In some examples, the electrode pairs have different gap sizes.

Figure 30:
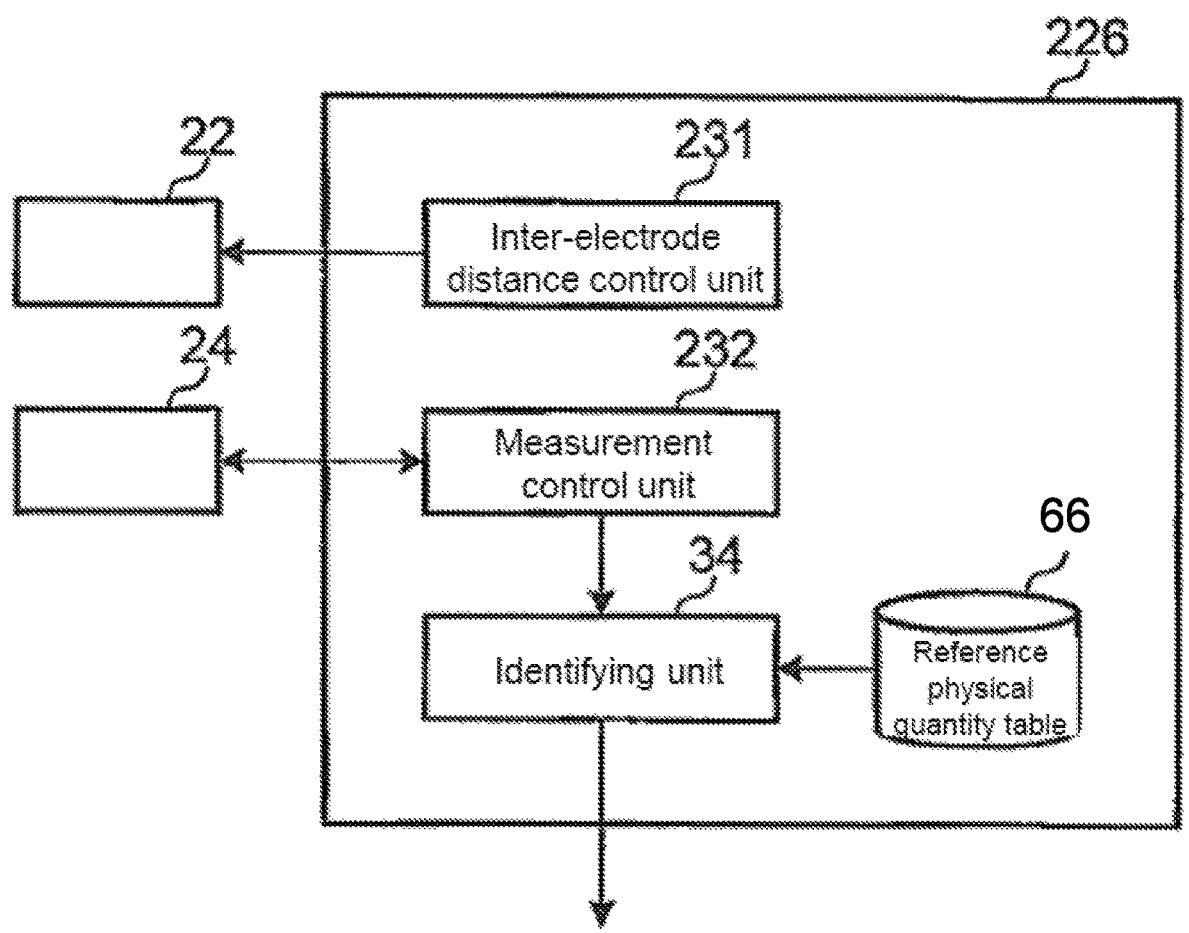
FIG. 30 is a block diagram showing a functional configuration of a control unit.

As shown in FIG. 30 control unit 226 may compose a configuration including an electrophoresis control unit 231, a measurement control unit 232, an identification unit 34, and a reference physical quantity table 36.

In order to let a peptide 50 pass repeatedly with multiple reversals through one passage formed between the electrodes of each of nanogap electrode pairs 12A, 12B, and 12C, electrophoresis control unit 231 may control voltage applied using electrophoresis power source 22 such that a direction of an electric field formed between the electrodes of an electrophoresis electrode pair 20 may be switched so as cause a polarization reversal of the field.

Measurement control unit 232 may control ammeter 24 so that ammeter 24 may measure tunneling current generated between the electrodes of each of nanogap electrode pairs 12A, 12B, and 12C, and may then utilize current values of tunneling current for different inter-electrode distances that may be measured by ammeter 24 so as to calculate conductance(s), and may generate conductance-time profile(s) for each inter-electrode distance.

In some embodiments a biomolecule sequencing apparatus 210 may be utilized wherein a solution in which peptide(s) 50 may be dissolved may be prepared; after nanogap electrode pairs 12A, 12B, and 12C may be disposed in a solution, a voltage(s) may be applied using measurement power source 18 to nanogap electrode pairs 12A, 12B, and 12C, and at the same time a voltage may be applied to electrophoresis electrode pair 20 using electrophoresis power source 22. Thus, a peptide 50 may pass through between a passage formed between electrodes of nanogap electrode pairs 12A, 12B, and 12C.

Figure 31:
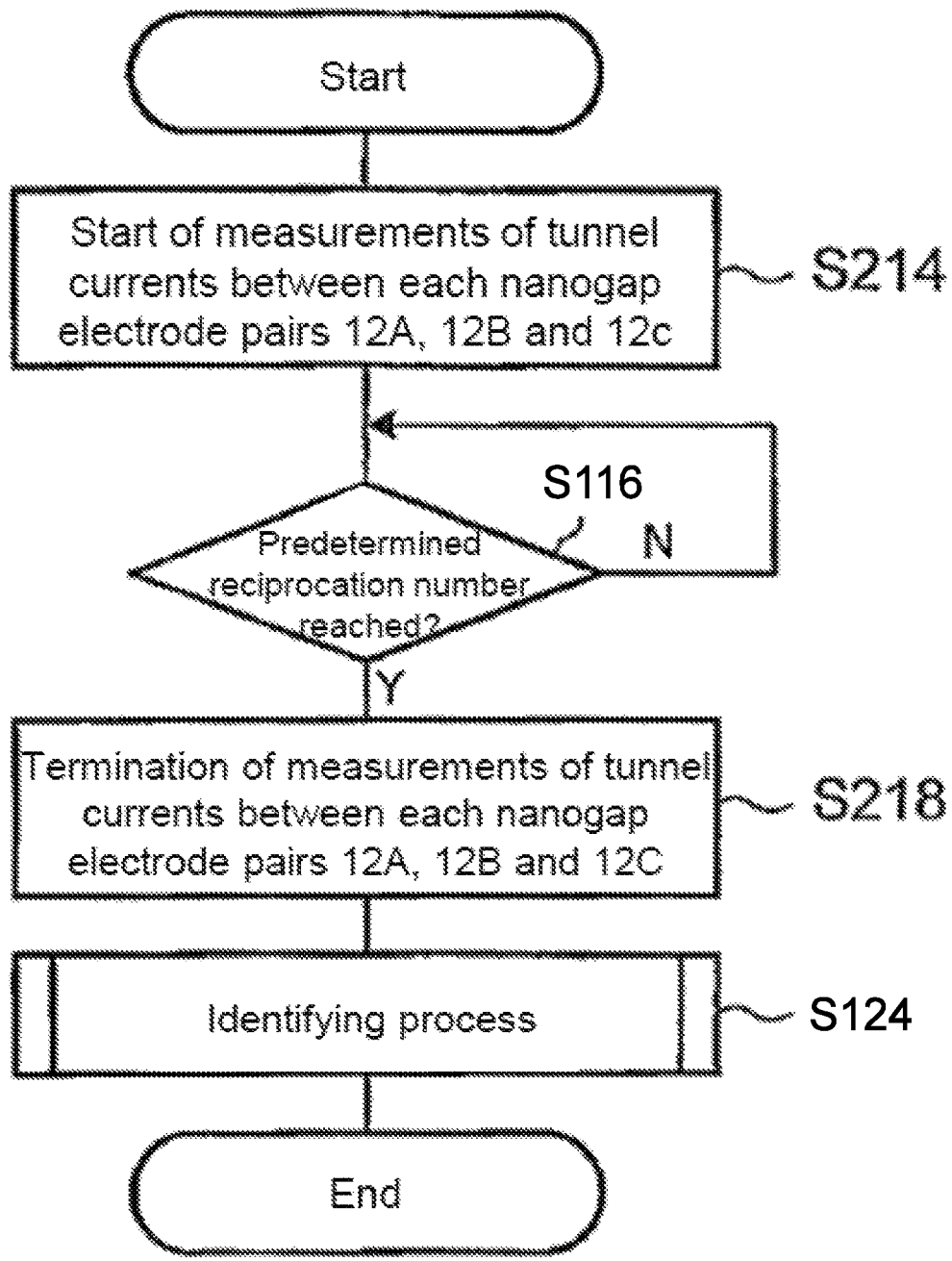
FIG. 31 is a flowchart showing a biomolecule sequencing process.

Then, a computer processor (e.g., CPU) of a computer comprising control unit 226 may retrieve and execute a biomolecule sequencing program that may be stored in ROM, RAM, FLASH or other storage media and may carry out a biomolecule sequencing process as shown in FIG. 31 utilizing biomolecule sequencing apparatus 210. In some embodiments, a biomolecule sequencing process may be carried out by biomolecule sequencing apparatus 210.

In step S214 associated a biomolecule sequencing process as shown in FIG. 31, measurement control unit 232 may control ammeter 24 and start measurement of current values of tunneling currents that may be generated between the electrodes of each of nanogap electrode pairs 12A, 12B, and 12C when peptide 50 passes through between a passage formed between the electrodes of nanogap electrode pairs 12A, 12B, and 12C. Measurement control unit 232 may utilize measured current values and store them in predetermined memory area associated with a measurement time for each measurement point and associated with information indicating which measured current value data results from which nanogap electrode pair 12A, 12B, and 12C, and the distances associated with each nanogap electrode pair (for example, d1, d2, and d3 indicating the inter-electrode distances).

Next, in step S16, electrophoresis control unit 231 may determine whether or not peptide 50 may have traversed for a prescribed number of times in a passage formed between the electrodes of each of nanogap electrode pairs 12A, 12B, and 12C. When a number of traversals may not reach a predetermined number, additional polarization reversals of voltage applied by electrophoresis control unit 231 may be effectuated so as to enable additional traversals. When a number of traversals reaches a predetermined number, operation may move to step S218, and measurement control unit 232 may terminate measurements of tunneling currents, and from obtained current values and measurement times, a conductance-time profile as shown in the upper diagram of FIG. 18 may be formed for different inter-electrode distances, and may be stored in a prescribed memory area.

Next, in step S24, an identification process as shown and described in associate with FIG. 25 may be carried out. Because an identification process may be the same as an identification process as described herein, explanation of this step is omitted.

In some embodiments, rather than using a fixed number of measurement traversals which a peptide 50 or other polymer may be controlled to perform by electrophoresis control unit 231, data may be analyzed during a process of moving of peptide(s) 50 or other polymers until a desired quality metric, which may be a Q-score or other appropriate metric, has been achieved. Thus a variable number of traversals for which a peptide(s) 50 or other polymer may traverse through between electrodes of a nanogap electrode pair(s) may be greater or lesser than a number which may have been selected so as to give a nominally desired quality score.

In some embodiments as explained above, a biomolecule sequencing apparatus with multiple nanogap electrode pairs may be utilized in a manner similar to a biomolecule sequencing apparatus wherein an adjustable nanogap electrode pair may be utilized with various adjusted nanogap electrode pair gap spacings so as to identify monomers comprising a biomolecule with a simple configuration and with high accuracy. In addition, because tunneling currents for different nanogap electrode pair spacings may be measured simultaneously, the measurement time of tunneling currents may be shortened in comparison with a biomolecule sequencing apparatus wherein nanogap distances may need to be adjusted.

As described herein, explanation was made as to a configuration in which nanogap electrode pairs 12A, 12B, and 12C may be laminated such that each inter-electrode centers may be arranged on the same axis, but in other embodiments, different electrode gap spacings may, for example, be associated with different channels. For example, nanogap electrode pairs 12A, 12B, and 12C may be disposed on the same plane. In this case, additional electrophoresis electrodes may be utilized in association with nanogap electrode pairs 12A, 12B, and 12C, for example, so that the system is controlled such that peptide 50 may pass serially through between electrodes of each of the nanogap electrode pairs 12A, 12B, and 12C.

Figure 32:
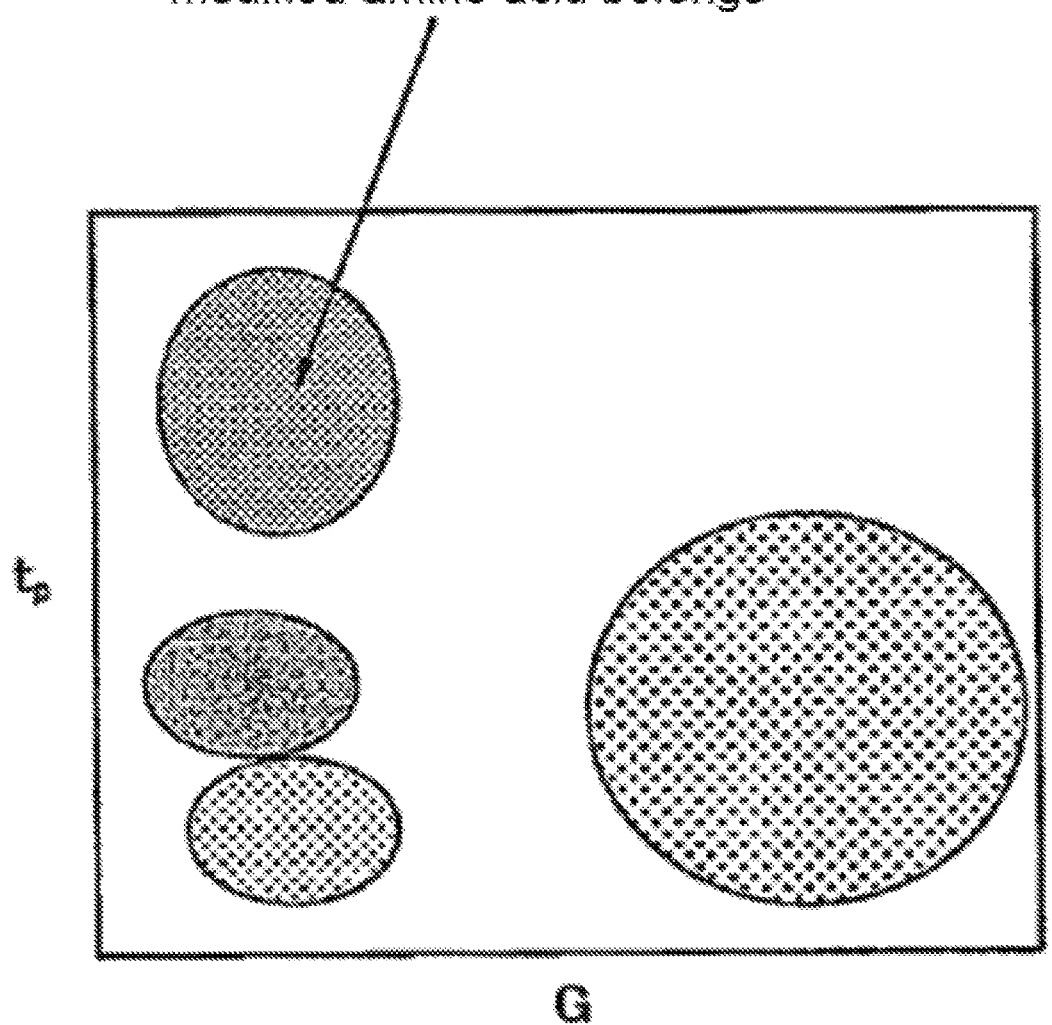
FIG. 32 is a view showing conductance separation of modified amino acids.

As described herein, reference has been made to 20 or more kinds of amino acids which may comprise a peptide that may be identified; however, it may also be possible to identify additional kinds of amino acids including modified amino acids. A modified amino acid may have an enlarged molecular diameter. Therefore, a point in the $t_p$-G space, for which a relative conductance calculated from a tunneling current measured utilizing an inter-electrode distance d set approximately to a molecular diameter and a peak pulse duration time may be mapped, may be readily identified from points of other amino acids; and thus, as roughly shown in FIG. 32, a modified amino acid may be classified clearly so that an indicator with which a kind of amino acids may be identified may be obtained. Accordingly, modified amino acids may also be identified with a simple configuration and with high accuracy, without preliminary treatment such as chemical modification. A modified amino acid like this may control an active or an inactive state of protein, and thus, this may be a very important target of a disease diagnosis, for example, N-terminal acetylation associated with various forms of cancer.

In some embodiments, a single type of reference substance may be utilized, wherein a single type of reference substance may be appropriate for various different inter-electrode nanogap electrode pair spacings, potentially being useful as a reference substance as described herein for all different inter-electrode nanogap electrode pair spacings. In other embodiments, multiple reference substances may be utilized wherein one or more reference substances may be better suited for use with a range of distances of inter-electrode nanogap electrode pair spacings, while a different one or more reference substances may be better suited for a different range of distances of inter-electrode nanogap electrode pair spacings. Reference substances may be selected for different inter-electrode nanogap electrode pair spacings as a function of the size of the reference substance, or as a function of the distance between active electro active sites on a reference substance.

In some embodiments as described herein, a reference substance may be generally spherical, such that the orientation of the reference substance within an inter-electrode nanogap electrode par spacing may not have a substantive effect on the tunneling current generated by a reference substance. In other embodiments, a reference substance may be utilized wherein orientation may have a significant effect on a tunneling current generated thereby, but wherein the reference substance may be sterically hindered from interacting with a nanogap electrode pair in manner that allows significant variation in tunneling current, thereby allow a compound to act as a reference substance. In further embodiments, a reference substance may be utilized wherein orientation may have a significant effect on a tunneling current generated thereby, but wherein the reference substance may be oriented by charge associated with the reference substance so as to prevent a reference substance from interacting with a nanogap electrode pair in manner that allows significant variation in tunneling current, thereby allow a compound to act as a reference substance.

In some embodiments, a reference substance may have a pulse duration which is similar to pulse durations associated with monomers of a polymer which is being sequenced. In other embodiments, a reference substance may have a pulse duration which may significantly longer or shorter than a pulse duration associated with monomers of a polymer being sequenced, allowing the pulse duration of a reference substance to be utilized as an additional factor in determining whether a pulse is associated with a reference substance or a monomer of a polymer being sequenced.

In some cases, reference has been made to a peptide (protein) as an exemplary biopolymer (biomolecule), and of amino acids as monomers comprising the biomolecule, but the present disclosure is not limited to this. For example, in some embodiments a biomolecule sequencing apparatus may be utilized to identify nucleotides comprising nucleic acid(s) and to identify monosaccharides comprising sugar chain(s).

A program may be installed in advance, but it will be appreciated that devices, systems and methods of the present disclosure may be executed in situations in which a program is stored in an external memory device, memory medium, or the like, which may be read-in or down-loaded via the Internet, an intranet, or other network. Alternatively, it is also possible to provide this program after it is stored in a memory medium that is readable by a computer.

In some embodiments wherein a program may be described as being installed in advance, a program may be stored in an external storage device or storage medium and may be read out as needed, or a program may be downloaded through an internet connection. Moreover, a program may be stored in a separately provided computer readable storage medium.

Samples and reagents can be delivered to nanogap electrodes and sets of electrodes using fluid flow units 8 (FIG. 2), which can include one or more pumps. A fluid flow unit can include a single pump or a series of pumps. In some examples, the pumps are micropumps, such as on-chip pumps. A fluid flow unit can include one or more valves for directing fluid flow. The pumps and valves of a fluid flow unit can be controlled by control units 28 (FIG. 2) and computer control systems 26 (FIG. 2) described elsewhere herein.

Computer Control Systems

Figure 33:
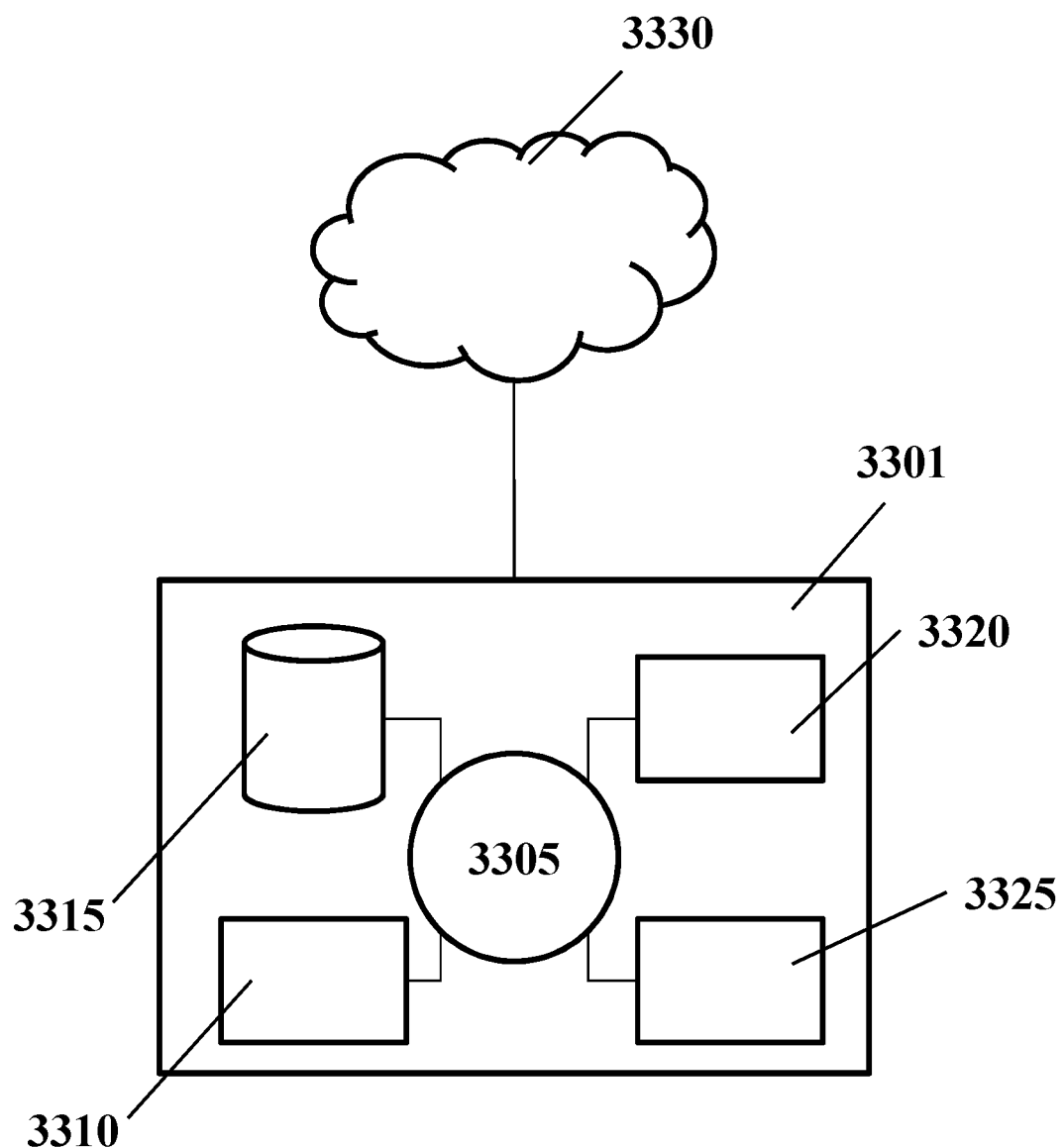
FIG. 33 shows a computer control system that is programmed or otherwise configured to implement devices, systems and methods of the present disclosure.

The present disclosure provides computer control systems that are programmed to implement methods of the disclosure. FIG. 33 shows a computer system 3301 that is programmed or otherwise configured to sequence a biomolecule, such as a protein. The computer system 3301 can be the control units 26 and 226 described elsewhere herein. The computer system 3301 includes a central processing unit (CPU, also "processor" and "computer processor" herein) 3305, which can be a single core or multi core processor, or a plurality of processors for parallel processing. The computer system 3301 also includes memory or memory location 3310 (e.g., random-access memory, read-only memory, flash memory), electronic storage unit 3315 (e.g., hard disk), communication interface 3320 (e.g., network adapter) for communicating with one or more other systems, and peripheral devices 3325, such as cache, other memory, data storage and/or electronic display adapters. The memory 3310, storage unit 3315, interface 3320 and peripheral devices 3325 are in communication with the CPU 3305 through a communication bus (solid lines), such as a motherboard. The storage unit 3315 can be a data storage unit (or data repository) for storing data. The computer system 3301 can be operatively coupled to a computer network ("network") 3330 with the aid of the communication interface 3320. The network 3330 can be the Internet, an internet and/or extranet, or an intranet and/or extranet that is in communication with the Internet. The network 3330 in some cases is a telecommunication and/or data network. The network 3330 can include one or more computer servers, which can enable distributed computing, such as cloud computing. The network 3330, in some cases with the aid of the computer system 3301, can implement a peer-to-peer network, which may enable devices coupled to the computer system 3301 to behave as a client or a server.

The CPU 3305 can execute a sequence of machine-readable instructions, which can be embodied in a program or software. The instructions may be stored in a memory location, such as the memory 3310. The instructions can be directed to the CPU 3305, which can subsequently program or otherwise configure the CPU 3305 to implement methods of the present disclosure. Examples of operations performed by the CPU 3305 can include fetch, decode, execute, and writeback.

The CPU 3305 can be part of a circuit, such as an integrated circuit. One or more other components of the system 3301 can be included in the circuit. In some cases, the circuit is an application specific integrated circuit (ASIC).

The storage unit 3315 can store files, such as drivers, libraries and saved programs. The storage unit 3315 can store user data, e.g., user preferences and user programs. The computer system 3301 in some cases can include one or more additional data storage units that are external to the computer system 3301, such as located on a remote server that is in communication with the computer system 3301 through an intranet or the Internet.

The computer system 3301 can communicate with one or more remote computer systems through the network 3330. For instance, the computer system 3301 can communicate with a remote computer system of a user. The user can access the computer system 3301 via the network 3330.

Methods as described herein can be implemented by way of machine (e.g., computer processor) executable code stored on an electronic storage location of the computer system 3301, such as, for example, on the memory 3310 or electronic storage unit 3315. The machine executable or machine readable code can be provided in the form of software. During use, the code can be executed by the processor 3305. In some cases, the code can be retrieved from the storage unit 3315 and stored on the memory 3310 for ready access by the processor 3305. In some situations, the electronic storage unit 3315 can be precluded, and machine-executable instructions are stored on memory 3310.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 3301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine (or computer) readable medium, such as computer-executable code (or computer program), may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Devices, systems and methods of the present disclosure may be combined with and/or modified by other devices, systems, or methods, such as those described in, for example, JP 2013-36865A, US 2012/0322055A, US 2013/0001082A, US 2012/0193237A, US 2010/0025249A, JP 2011-163934A, JP 2005-257687A, JP 2011-163934A and JP 2008-32529A, each of which is entirely incorporated herein by reference.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for detecting a biomolecule using at least one pair of nanogap electrodes, comprising:
   a fluid flow unit comprising at least one pump for directing a plurality of monomers with reference substances bound thereto to the at least one pair of nanogap electrodes, wherein the reference substances comprise a first reference substance bound to a first monomer and a second reference substance bound to a second monomer, wherein the first reference substance is different than the second reference substance; and
   a computer processor coupled to the at least one pair of nanogap electrodes and programmed to:
   (a) measure tunneling nanocurrent signals resulting from the plurality of monomers with reference substances bound thereto using the at least one pair of nanogap electrodes, wherein the tunneling nanocurrent signals correspond to the reference substances, wherein the first reference substance and the second reference substance correspond to different tunneling nanocurrent signals; and
   (b) identify a monomer of the plurality of monomers with reference substances bound thereto based on the tunneling nanocurrent signals measured in (a).

2. The system of claim 1, wherein the monomer of the plurality of monomers with reference substances bound thereto is identified based upon a reference physical quantity of the monomer.

3. The system of claim 1, wherein the reference substances are electrically conductive.

4. The system of claim 1, wherein the tunneling nanocurrent signals of the reference substances are measured for at least about one second.

5. The system of claim 1, wherein the at least one pair of nanogap electrodes is normalized using the reference substances.

6. The system of claim 1, wherein the biomolecule is between electrodes of the at least one pair of nanogap electrodes.

7. The system of claim 1, wherein the monomer of the plurality of monomers with reference substances bound thereto is bound to the biomolecule, and wherein the computer processor is further programmed to detect the reference substances using the tunneling nanocurrent signals measured in (a).

8. The system of claim 1, wherein the reference substances comprise subunits.

9. The system of claim 1, wherein the plurality of monomers with reference substances bound thereto comprises native nucleotide bases and/or modified nucleotide bases.

10. The system of claim 1, wherein the plurality of monomers with reference substances bound thereto is incorporatable.

11. The system of claim 10, wherein the monomer of the plurality of monomers with reference substances bound thereto comprises a portion of a double stranded nucleic acid.

12. The system of claim 11, wherein the portion of the double stranded nucleic acid is sequenced.

13. A method of detecting a biomolecule, comprising:
   (a) providing a plurality of monomers with reference substances bound thereto, wherein the reference substances comprise a first reference substance bound to a first monomer and a second reference substance bound to a second monomer, wherein the first reference substance is different than the second reference substance;
   (b) using at least one pair of nanogap electrodes to measure tunneling nanocurrent signals resulting from the plurality of monomers with reference substances bound thereto, the tunneling nanocurrent signals corresponding to the reference substances, wherein the the first reference substance and the second reference substance correspond with different tunneling nanocurrent signals; and
   (c) identifying a monomer of the plurality of monomers with reference substances bound thereto based on the tunneling nanocurrent signals measured in (b).

14. The method of claim 13, wherein the identifying of the monomer of the plurality of monomers with reference substances bound thereto is based upon a reference physical quantity of the monomer.

15. The method of claim 13, wherein the reference substances are electrically conductive.

16. The method of claim 13, wherein the tunneling nanocurrent signals of the reference substances are measured for at least about one second.

17. The method of claim 13, further comprising normalizing the at least one pair of nanogap electrodes using the reference substances.

18. The method of claim 13, wherein the biomolecule is between electrodes of the at least one pair of nanogap electrodes.

19. The method of claim 13, wherein the monomer of the plurality of monomers with reference substances bound thereto is bound to the biomolecule, and wherein the method further comprises detecting the reference substances using the tunneling nanocurrent signals measured in (b).

20. The method of claim 13, wherein the reference substances comprise subunits.

21. The method of claim 13, wherein the plurality of monomers with reference substances bound thereto comprises native nucleotide bases and/or modified nucleotide bases.

22. The method of claim 13, wherein the plurality of monomers with reference substances bound thereto is incorporatable.

23. The method of claim 22, wherein the monomer of the plurality of monomers with reference substances bound thereto comprises a portion of a double stranded nucleic acid.

24. The method of claim 23, wherein the portion of the double stranded nucleic acid is sequenced.

* * * * *